United States Patent
Chamberlain et al.

(10) Patent No.: US 9,200,079 B2
(45) Date of Patent: *Dec. 1, 2015

(54) FC VARIANTS WITH ALTERED BINDING TO FCRN

(75) Inventors: Aaron Keith Chamberlain, Pasadena, CA (US); John R. Desjarlais, Pasadena, CA (US); Sher Bahadur Karki, Pomona, CA (US); Gregory Alan Lazar, Los Angeles, CA (US); Jost Vielmetter, Altadena, CA (US); Sean Christopher Yoder, Simi Valley, CA (US)

(73) Assignee: Xencor, Inc., Monrovia, CA (US)

( * ) Notice: Subject to any disclaimer, the term of this patent is extended or adjusted under 35 U.S.C. 154(b) by 591 days.

This patent is subject to a terminal disclaimer.

(21) Appl. No.: 11/274,065

(22) Filed: Nov. 14, 2005

(65) Prior Publication Data

US 2006/0173170 A1 Aug. 3, 2006

Related U.S. Application Data

(60) Provisional application No. 60/627,763, filed on Nov. 12, 2004, provisional application No. 60/642,886, filed on Jan. 11, 2005, provisional application No. 60/649,508, filed on Feb. 2, 2005, provisional application No. 60/662,468, filed on Mar. 15, 2005, provisional application No. 60/669,311, filed on Apr. 6, 2005, provisional application No. 60/681,607, filed on May 16, 2005, provisional application No. 60/690,200, filed on Jun. 13, 2005, provisional application No. 60/696,609, filed on Jul. 5, 2005, provisional application No. 60/703,018, filed on Jul. 27, 2005, provisional application No. 60/726,453, filed on Oct. 12, 2005.

(51) Int. Cl.
| | |
|---|---|
| *C07K 16/00* | (2006.01) |
| *C12P 21/08* | (2006.01) |
| *A61K 39/395* | (2006.01) |
| *C07K 16/32* | (2006.01) |
| *C07K 16/28* | (2006.01) |
| *C07K 1/00* | (2006.01) |

(52) U.S. Cl.
CPC .............. *C07K 16/32* (2013.01); *C07K 16/2893* (2013.01); *C07K 2317/24* (2013.01); *C07K 2317/52* (2013.01); *C07K 2317/526* (2013.01); *C07K 2317/71* (2013.01); *C07K 2317/72* (2013.01); *C07K 2317/92* (2013.01)

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| 4,485,045 A | 11/1984 | Regen et al. |
| 4,544,545 A | 10/1985 | Ryan et al. |
| 4,753,894 A | 6/1988 | Frankel et al. |
| 4,816,397 A | 3/1989 | Boss et al. |
| 4,816,567 A | 3/1989 | Cabilly et al. |
| 4,943,533 A | 7/1990 | Mendelsohn et al. |
| 4,975,278 A | 12/1990 | Senter et al. |
| 5,208,020 A | 5/1993 | Chari et al. |
| 5,225,348 A | 7/1993 | Nagata et al. |
| 5,225,539 A | 7/1993 | Winter et al. |
| 5,264,586 A | 11/1993 | Nicolaou et al. |
| 5,266,491 A | 11/1993 | Nagata et al. |
| 5,328,987 A | 7/1994 | Maliszewski |
| 5,500,362 A | 3/1996 | Robinson et al. |
| 5,530,101 A | 6/1996 | Queen et al. |
| 5,541,087 A | 7/1996 | Lo et al. |
| 5,558,864 A | 9/1996 | Bendig et al. |
| 5,576,184 A | 11/1996 | Better et al. |
| 5,585,089 A | 12/1996 | Queen et al. |
| 5,623,053 A | 4/1997 | Gastinel et al. |
| 5,624,821 A | 4/1997 | Winter et al. |
| 5,633,162 A | 5/1997 | Keen et al. |
| 5,648,237 A | 7/1997 | Carter |
| 5,648,260 A | 7/1997 | Winter et al. |
| 5,658,570 A | 8/1997 | Newman et al. |
| 5,677,171 A | 10/1997 | Hudziak et al. |
| 5,681,566 A | 10/1997 | Stevenson et al. |
| 5,693,761 A | 12/1997 | Queen et al. |
| 5,693,762 A | 12/1997 | Queen et al. |
| 5,712,374 A | 1/1998 | Kuntsmann et al. |
| 5,714,586 A | 2/1998 | Kunstmann et al. |
| 5,736,137 A | 4/1998 | Anderson et al. |
| 5,750,105 A | 5/1998 | Newman et al. |
| 5,773,001 A | 6/1998 | Hamann et al. |
| 5,804,396 A | 9/1998 | Plowman et al. |
| 5,821,337 A | 10/1998 | Carter et al. |
| 5,834,597 A | 11/1998 | Tso et al. |

(Continued)

FOREIGN PATENT DOCUMENTS

| | | |
|---|---|---|
| CN | 1163506 | 8/2004 |
| EP | 640094 | 11/1993 |

(Continued)

OTHER PUBLICATIONS

Bjorkman's declaration, Jan. 17, 2011, pp. 1-14.*

(Continued)

*Primary Examiner* — Chun Dahle
(74) *Attorney, Agent, or Firm* — Gargi Talukder; Robin M. Silva; Morgan, Lewis & Bockius, LLP

(57) ABSTRACT

The present application relates to optimized IgG immunoglobulin engineering methods for their generation, and their application, particularly for therapeutic purposes.

5 Claims, 38 Drawing Sheets

(56) References Cited

U.S. PATENT DOCUMENTS

| | | |
|---|---|---|
| 5,859,205 A | 1/1999 | Adair et al. |
| 5,885,573 A | 3/1999 | Bluestone et al. |
| 5,891,996 A | 4/1999 | Mateo De Acosta Del Rio et al. |
| 6,030,613 A | 2/2000 | Blumberg et al. |
| 6,054,297 A | 4/2000 | Carter et al. |
| 6,086,875 A | 7/2000 | Blumberg et al. |
| 6,121,022 A | 9/2000 | Presta et al. |
| 6,165,745 A | 12/2000 | Ward et al. |
| 6,180,370 B1 | 1/2001 | Queen et al. |
| 6,188,965 B1 | 2/2001 | Mayo et al. |
| 6,194,551 B1 | 2/2001 | Idusogie et al. |
| 6,235,883 B1 | 5/2001 | Jakobovits et al. |
| 6,242,195 B1 | 6/2001 | Idusogie et al. |
| 6,269,312 B1 | 7/2001 | Mayo et al. |
| 6,277,375 B1 | 8/2001 | Ward |
| 6,284,536 B1 | 9/2001 | Morrison et al. |
| 6,331,415 B1 | 12/2001 | Cabilly et al. |
| 6,358,733 B1 | 3/2002 | Motwani et al. |
| 6,365,161 B1 | 4/2002 | Deo et al. |
| 6,403,312 B1 | 6/2002 | Dahiyat et al. |
| 6,407,213 B1 | 6/2002 | Carter et al. |
| 6,444,789 B1 | 9/2002 | Luo |
| 6,485,726 B1 | 11/2002 | Blumberg et al. |
| 6,506,883 B2 | 1/2003 | Meteo de Acosta del Rio |
| 6,528,624 B1 | 3/2003 | Idusogie et al. |
| 6,538,124 B1 | 3/2003 | Idusogie et al. |
| 6,602,684 B1 | 8/2003 | Umana et al. |
| 6,632,927 B2 | 10/2003 | Adair et al. |
| 6,649,165 B2 | 11/2003 | Schubert |
| 6,708,120 B1 | 3/2004 | Mayo et al. |
| 6,719,971 B1 | 4/2004 | Carter et al. |
| 6,737,056 B1 | 5/2004 | Presta |
| 6,792,356 B2 | 9/2004 | Mayo et al. |
| 6,797,492 B2 | 9/2004 | Daugherty et al. |
| 6,801,861 B2 | 10/2004 | Mayo et al. |
| 6,804,611 B2 | 10/2004 | Mayo et al. |
| 6,821,505 B2 | 11/2004 | Ward |
| 6,875,846 B2 | 4/2005 | Rennert et al. |
| 6,933,368 B2 | 8/2005 | Co et al. |
| 6,946,292 B2 | 9/2005 | Kanda et al. |
| 6,950,754 B2 | 9/2005 | Mayo et al. |
| 6,982,321 B2 | 1/2006 | Winter |
| 6,992,234 B2 | 1/2006 | Roopenian |
| 7,008,784 B1 | 3/2006 | Haynes et al. |
| 7,056,695 B2 | 6/2006 | Dahiyat et al. |
| 7,083,784 B2 | 8/2006 | Dall'Acqua et al. |
| 7,101,974 B2 | 9/2006 | Dahiyat et al. |
| 7,117,096 B2 | 10/2006 | Luo et al. |
| 7,217,797 B2 | 5/2007 | Hinton et al. |
| 7,244,823 B2 | 7/2007 | Dahiyat et al. |
| 7,247,301 B2 | 7/2007 | van de Winkel et al. |
| 7,276,585 B2 | 10/2007 | Lazar et al. |
| 7,315,786 B2 | 1/2008 | Dahiyat et al. |
| 7,317,091 B2 | 1/2008 | Lazar et al. |
| 7,355,008 B2 | 4/2008 | Stavenhagen et al. |
| 7,361,740 B2 | 4/2008 | Hinton et al. |
| 7,371,826 B2 | 5/2008 | Presta et al. |
| 7,662,925 B2 | 2/2010 | Lazar et al. |
| 7,670,600 B2 | 3/2010 | Dall'Acqua et al. |
| 7,790,655 B2 | 9/2010 | Gao et al. |
| 7,863,419 B2 | 1/2011 | Taylor |
| 8,338,574 B2 * | 12/2012 | Chamberlain et al. ..... 530/387.1 |
| 8,883,973 B2 * | 11/2014 | Chamberlain et al. ..... 530/387.1 |
| 2001/0036459 A1 | 11/2001 | Ravetch |
| 2001/0044003 A1 | 11/2001 | Gallucci et al. |
| 2002/0004587 A1 | 1/2002 | Miller et al. |
| 2002/0048772 A1 | 4/2002 | Dahiyat et al. |
| 2002/0062010 A1 | 5/2002 | Arathoon et al. |
| 2002/0090648 A1 | 7/2002 | Dahiyat et al. |
| 2002/0098193 A1 | 7/2002 | Ward et al. |
| 2002/0119492 A1 | 8/2002 | Chirino et al. |
| 2002/0142374 A1 | 10/2002 | Gallo et al. |
| 2002/0155537 A1 | 10/2002 | Carter et al. |
| 2002/0164328 A1 | 11/2002 | Shinkawa et al. |
| 2002/0168640 A1 | 11/2002 | Li et al. |
| 2002/0172968 A1 | 11/2002 | Liu et al. |
| 2002/0192222 A1 | 12/2002 | Blumberg et al. |
| 2003/0003097 A1 | 1/2003 | Reff et al. |
| 2003/0012789 A1 | 1/2003 | Blumberg et al. |
| 2003/0044858 A1 | 3/2003 | Jardieu et al. |
| 2003/0049654 A1 | 3/2003 | Dahiyat et al. |
| 2003/0068649 A1 | 4/2003 | Doberstein et al. |
| 2003/0073164 A1 | 4/2003 | Simmons et al. |
| 2003/0078385 A1 | 4/2003 | Arathoon et al. |
| 2003/0105294 A1 | 6/2003 | Gillies et al. |
| 2003/0108548 A1 | 6/2003 | Bluestone et al. |
| 2003/0118592 A1 | 6/2003 | Ledbetter et al. |
| 2003/0124537 A1 | 7/2003 | Liu et al. |
| 2003/0130827 A1 | 7/2003 | Bentzien et al. |
| 2003/0133939 A1 | 7/2003 | Ledbetter et al. |
| 2003/0143682 A1 | 7/2003 | Nicolaides et al. |
| 2003/0157108 A1 | 8/2003 | Presta |
| 2003/0158289 A1 | 8/2003 | Rusin et al. |
| 2003/0158389 A1 | 8/2003 | Idusogie et al. |
| 2003/0166868 A1 | 9/2003 | Presta et al. |
| 2003/0175884 A1 | 9/2003 | Umana et al. |
| 2003/0190311 A1 | 10/2003 | Dall'Acqua et al. |
| 2003/0208054 A1 | 11/2003 | Olsen et al. |
| 2003/0224397 A1 | 12/2003 | Lowman et al. |
| 2003/0229208 A1 | 12/2003 | Queen et al. |
| 2003/0235536 A1 | 12/2003 | Blumberg et al. |
| 2004/0002587 A1 | 1/2004 | Watkins et al. |
| 2004/0043429 A1 | 3/2004 | Dahiyat et al. |
| 2004/0043430 A1 | 3/2004 | Dahiyat et al. |
| 2004/0062763 A1 | 4/2004 | Mosser et al. |
| 2004/0093621 A1 | 5/2004 | Shitara et al. |
| 2004/0110226 A1 | 6/2004 | Lazar et al. |
| 2004/0132101 A1 | 7/2004 | Lazar et al. |
| 2004/0185045 A1 | 9/2004 | Koenig et al. |
| 2004/0191244 A1 | 9/2004 | Presta |
| 2004/0191256 A1 | 9/2004 | Raju |
| 2004/0192897 A2 | 9/2004 | Winter |
| 2004/0228856 A1 | 11/2004 | Presta |
| 2004/0254108 A1 | 12/2004 | Ma et al. |
| 2004/0258677 A1 | 12/2004 | Waldmann et al. |
| 2004/0258682 A1 | 12/2004 | Leung et al. |
| 2004/0259150 A1 | 12/2004 | Nakamura et al. |
| 2005/0014934 A1 | 1/2005 | Hinton et al. |
| 2005/0020527 A1 | 1/2005 | Peters et al. |
| 2005/0031626 A1 | 2/2005 | Stevenson |
| 2005/0032114 A1 | 2/2005 | Hinton et al. |
| 2005/0033029 A1 | 2/2005 | Lu |
| 2005/0037000 A1 | 2/2005 | Stavenhagen |
| 2005/0037002 A1 | 2/2005 | Velardi et al. |
| 2005/0038610 A1 | 2/2005 | Mayo et al. |
| 2005/0054046 A1 | 3/2005 | Presta et al. |
| 2005/0064514 A1 | 3/2005 | Stavenhagen et al. |
| 2005/0118174 A1 | 6/2005 | Presta |
| 2005/0152894 A1 | 7/2005 | Krummen et al. |
| 2005/0175614 A1 | 8/2005 | Ledbetter et al. |
| 2005/0180948 A1 | 8/2005 | Desjarlais et al. |
| 2005/0202023 A1 | 9/2005 | Ledbetter et al. |
| 2005/0202028 A1 | 9/2005 | Ledbetter et al. |
| 2005/0202534 A1 | 9/2005 | Ledbetter et al. |
| 2005/0215767 A1 | 9/2005 | Koenig et al. |
| 2005/0226864 A1 | 10/2005 | Hinton et al. |
| 2005/0233382 A1 | 10/2005 | Presta |
| 2005/0272128 A1 | 12/2005 | Umana et al. |
| 2005/0276799 A1 | 12/2005 | Hinton et al. |
| 2006/0008883 A1 | 1/2006 | Lazar et al. |
| 2006/0013810 A1 | 1/2006 | Johnson et al. |
| 2006/0019316 A1 | 1/2006 | Mayo et al. |
| 2006/0067930 A1 | 3/2006 | Adams et al. |
| 2006/0134709 A1 | 6/2006 | Stavenhagen et al. |
| 2006/0173170 A1 | 8/2006 | Chamberlain |
| 2006/0235208 A1 | 10/2006 | Lazar et al. |
| 2006/0275283 A1 | 12/2006 | van Vlijmen et al. |
| 2007/0036799 A1 | 2/2007 | Stavenhagen et al. |
| 2007/0041907 A1 | 2/2007 | Ober |
| 2007/0087005 A1 | 4/2007 | Lazar et al. |
| 2007/0122406 A1 | 5/2007 | Chamberlain et al. |
| 2007/0148164 A1 * | 6/2007 | Farrington et al. ........ 424/133.1 |
| 2007/0224188 A1 | 9/2007 | Allan et al. |
| 2007/0224192 A1 | 9/2007 | Lazar et al. |

(56) References Cited

U.S. PATENT DOCUMENTS

| | | |
|---|---|---|
| 2007/0238665 A1 | 10/2007 | Lazar et al. |
| 2008/0071063 A1 | 3/2008 | Allan et al. |
| 2008/0112961 A1 | 5/2008 | Stavenhagen et al. |
| 2008/0138349 A1 | 6/2008 | Stavenhagen et al. |
| 2008/0206867 A1 | 8/2008 | Desjarlais et al. |
| 2009/0068110 A1 | 3/2009 | Shang et al. |
| 2009/0163699 A1 | 6/2009 | Chamberlain et al. |
| 2010/0098711 A1 | 4/2010 | Masat et al. |
| 2010/0166741 A1 | 7/2010 | Kelley |

FOREIGN PATENT DOCUMENTS

| | | |
|---|---|---|
| EP | 0 268 636 B1 | 1/1997 |
| EP | 1 176 195 A1 | 1/2002 |
| EP | 1 229 125 A1 | 8/2002 |
| EP | 1 255 209 A2 | 11/2002 |
| EP | 1 255 826 B1 | 11/2002 |
| EP | 0 753 065 B1 | 5/2003 |
| EP | 0 805 628 B1 | 5/2003 |
| EP | 1355919 | 10/2003 |
| EP | 1 323 346 A2 | 11/2003 |
| EP | 1 323 346 A3 | 11/2003 |
| EP | 0 888 125 B1 | 5/2004 |
| EP | 0 904 107 B1 | 10/2004 |
| EP | 0 383 799 B2 | 2/2005 |
| WO | WO 81/01145 | 4/1981 |
| WO | WO 88/07089 A1 | 9/1988 |
| WO | WO 88/07378 | 10/1988 |
| WO | WO 91/06305 A1 | 5/1991 |
| WO | WO 91/19515 A1 | 12/1991 |
| WO | WO 92/04053 A1 | 3/1992 |
| WO | WO 92/16562 A1 | 10/1992 |
| WO | WO 92/22324 A1 | 12/1992 |
| WO | WO 93/21232 | 10/1993 |
| WO | WO 93/22332 | 11/1993 |
| WO | WO 94/11026 | 5/1994 |
| WO | WO 94/29351 A2 | 12/1994 |
| WO | WO 94/29351 A3 | 12/1994 |
| WO | WO 95/05468 A1 | 2/1995 |
| WO | WO 95/20045 | 7/1995 |
| WO | WO 96/22024 A1 | 7/1996 |
| WO | WO 96/30347 | 10/1996 |
| WO | WO 96/33978 | 10/1996 |
| WO | WO 96/40210 | 12/1996 |
| WO | WO 97/28267 A1 | 8/1997 |
| WO | WO 97/34631 A1 | 9/1997 |
| WO | WO 97/38731 | 10/1997 |
| WO | WO 97/38983 | 10/1997 |
| WO | WO 97/43316 | 11/1997 |
| WO | WO 98/02462 A1 | 1/1998 |
| WO | WO 98/05787 A1 | 2/1998 |
| WO | WO 98/23289 A1 | 6/1998 |
| WO | WO 98/43960 | 10/1998 |
| WO | WO 98/47089 A1 | 11/1998 |
| WO | WO 98/52976 | 11/1998 |
| WO | WO 98/59244 | 12/1998 |
| WO | WO 99/04813 A1 | 2/1999 |
| WO | WO 99/06378 | 2/1999 |
| WO | WO 99/06396 | 2/1999 |
| WO | WO 99/09016 | 2/1999 |
| WO | WO 99/51642 A1 | 10/1999 |
| WO | WO 99/54342 A1 | 10/1999 |
| WO | WO99/54484 A1 | 10/1999 |
| WO | WO 99/58572 A1 | 11/1999 |
| WO | WO 00/09560 A2 | 2/2000 |
| WO | WO 00/09560 A3 | 2/2000 |
| WO | WO 00/23564 A2 | 4/2000 |
| WO | WO 00/23564 A3 | 4/2000 |
| WO | WO 00/24782 A2 | 5/2000 |
| WO | WO 00/24782 A3 | 5/2000 |
| WO | WO 00/42072 A2 | 7/2000 |
| WO | WO 00/42072 A3 | 7/2000 |
| WO | WO 00/61739 A1 | 10/2000 |
| WO | WO 00/74728 | 12/2000 |
| WO | WO 01/14539 | 1/2001 |
| WO | WO 01/29246 A1 | 4/2001 |
| WO | WO 01/38490 A2 | 5/2001 |
| WO | WO 01/55322 | 8/2001 |
| WO | WO 01/57088 A1 | 8/2001 |
| WO | WO 01/59066 A2 | 8/2001 |
| WO | WO 01/59066 A3 | 8/2001 |
| WO | WO 01/62931 | 8/2001 |
| WO | WO 01/88138 | 11/2001 |
| WO | WO 02/05146 | 1/2002 |
| WO | WO 02/22826 | 3/2002 |
| WO | WO 02/30954 A1 | 4/2002 |
| WO | WO 02/31140 A1 | 4/2002 |
| WO | WO 02/44215 A2 | 6/2002 |
| WO | WO 02/060919 | 8/2002 |
| WO | WO 02/060919 A2 | 8/2002 |
| WO | WO 02/060919 A3 | 8/2002 |
| WO | WO 02/061090 A3 | 8/2002 |
| WO | WO 02/061093 A1 | 8/2002 |
| WO | WO02/066514 A | 8/2002 |
| WO | WO 02/066653 | 8/2002 |
| WO | WO 02/068453 | 9/2002 |
| WO | WO 02/068698 | 9/2002 |
| WO | WO 02/069232 | 9/2002 |
| WO | WO 02/077187 | 10/2002 |
| WO | WO02/079232 A2 | 10/2002 |
| WO | WO 03/000405 | 1/2003 |
| WO | WO 03/006154 | 1/2003 |
| WO | WO 03/014325 A2 | 2/2003 |
| WO | WO 03/014325 A3 | 2/2003 |
| WO | WO 03/016470 A2 | 2/2003 |
| WO | WO 03/035835 A2 | 5/2003 |
| WO | WO 03/035835 A3 | 5/2003 |
| WO | WO 03/054213 A2 | 7/2003 |
| WO | WO 03/059282 A | 7/2003 |
| WO | WO 03/074679 | * 9/2003 |
| WO | WO 03/089624 A2 | 10/2003 |
| WO | WO 2004/004662 A2 | 1/2004 |
| WO | WO 2004/004798 A2 | 1/2004 |
| WO | WO 2004/004798 A3 | 1/2004 |
| WO | WO 2004/016750 A3 | 2/2004 |
| WO | WO 2004/022717 A2 | 3/2004 |
| WO | WO 2004/022717 A3 | 3/2004 |
| WO | WO 2004/024871 A2 | 3/2004 |
| WO | WO 2004/024889 A2 | 3/2004 |
| WO | WO 2004/029207 A | 4/2004 |
| WO | WO 2004/035752 A2 | 4/2004 |
| WO | WO 2004/056312 A2 | 7/2004 |
| WO | WO 2004/063351 | 7/2004 |
| WO | WO 2004/063351 A2 | 7/2004 |
| WO | WO 2004/063351 A3 | 7/2004 |
| WO | WO2004/063963 A | 7/2004 |
| WO | WO 2004/074455 A2 | 9/2004 |
| WO | WO 2004/074455 A3 | 9/2004 |
| WO | WO 2004/091658 | 10/2004 |
| WO | WO 2004/092219 A2 | 10/2004 |
| WO | WO 2004/099249 | 11/2004 |
| WO | WO2004/099249 A | 11/2004 |
| WO | WO 2004/103404 A1 | 12/2004 |
| WO | WO 2004/110472 A2 | 12/2004 |
| WO | WO 2005/000899 A2 | 1/2005 |
| WO | WO 2005/001025 A2 | 1/2005 |
| WO | WO 2005/007809 A2 | 1/2005 |
| WO | WO 2005/011376 A2 | 2/2005 |
| WO | WO 2005/012877 A2 | 2/2005 |
| WO | WO 2005/013090 A2 | 2/2005 |
| WO | WO 2005/018572 A2 | 3/2005 |
| WO | WO 2005/023866 A2 | 3/2005 |
| WO | WO 2005/027966 A2 | 3/2005 |
| WO | WO 2005/037867 A1 | 4/2005 |
| WO | WO 2005/040217 A2 | 5/2005 |
| WO | WO 2005/047327 A2 | 5/2005 |
| WO | WO 2005047327 | 5/2005 |
| WO | WO 2005/056606 | 6/2005 |
| WO | WO 2005/056606 A | 6/2005 |
| WO | WO 2005/056759 A | 6/2005 |
| WO | WO 2005/060642 A2 | 7/2005 |
| WO | WO 2005/063815 A2 | 7/2005 |
| WO | WO 2005/070963 A1 | 8/2005 |

(56) References Cited

FOREIGN PATENT DOCUMENTS

| WO | WO 2005/115452 | 12/2005 |
|----|----------------|---------|
| WO | WO 2005/116078 A1 | 12/2005 |
| WO | WO 2005/123780 A2 | 12/2005 |
| WO | WO 2006/012500 A2 | 2/2006 |
| WO | WO 2006/019447 | 2/2006 |
| WO | WO 2006/020114 | 2/2006 |
| WO | WO 2006/031370 | 3/2006 |
| WO | WO 2006/034488 | 3/2006 |
| WO | WO 2006053301 | 5/2006 |
| WO | WO 2006/076594 | 7/2006 |
| WO | WO 2006/085967 | 8/2006 |
| WO | WO 2006/104989 | 10/2006 |
| WO | WO 2006/105338 | 10/2006 |
| WO | WO 2007/008943 | 1/2007 |
| WO | WO 2007/044616 | 4/2007 |
| WO | WO 2008/019199 | 2/2008 |
| WO | WO 2008/134046 | 11/2008 |
| WO | WO 2009/003019 | 12/2008 |
| WO | WO 2009/086320 | 7/2009 |

OTHER PUBLICATIONS

Ravetch's declaration, May 5, 2011, pp. 1-14.*
Email. May 21, 2015. pp. 1-3.*
Algre, et al., "A non-activating "humanized" anti-CD3 monoclonal antibody retains immunosuppressive properties in vivo," *Transplantation*, 57:1537-1543 (1994).
Armour, et al., "Recombinant human IgG molecules lacking Fcgamma receptor I binding and monocyte triggering activities," *Eur J Immunol*, 29:2613-2624 (1999).
Ashkenazi, et al., "Immunoadhesins as research tools and therapeutic agents," *Curr Opin Immunol*, 9:195-200 (1997).
Chamow, et al., "Immunoadhesins: principles and applications," *Trends Biotechnol*, 14:52-60 (1996).
Davies, et al. "Expression of GnTIII in a recombinant anti-CD20 CHO production cell line: Expression of antibodies with altered glycoforms leads to an increase in ADCC through higher affinity for FC gamma RIII," *Biotechnol Bioeng*, 74:288-294 (2001).
Hutchins, et al., "Improved biodistribution, tumor targeting, and reduced immunogenicity in mice with a gamma 4 variant of Campath-1H," *PNAS USA*, 92:11980-11984 (1995).
Jefferies, et al., *Immunol Lett*, 54:101-104 (1996).
Krapp, et al., "Structural analysis of human IgG-Fc glycoforms reveals a correlation between glycosylation and structural integrity," *J Mol Biol*, 325:979-989 (2003).
Lehrnbecher, et al., "Variant Genotypes of the Low-Affinity Fcγ Receptors in Two Control Populations and a Review of Low-Affinity Fcγ Receptor Polymorphisms in Control and Disease Populations," *Blood*, 94:4220-4232 (1999).
Lund, et al., "Human Fc gamma RI and Fc gamma RII interact with distinct but overlapping sites on human IgG," *J Immunol*, 147:2657-2662 (1991).
Lund, et al., "Multiple binding sites on the CH2 domain of IgG for mouse Fc gamma R11," *Mol Immunol*, 29:53-59 (1992).
Lund, et al., "Multiple interactions of IgG with its core oligosaccharide can modulate recognition by complement and human Fc gamma receptor I and influence the synthesis of its oligosaccharide chains," *J Immunol*, 154:4963-4969 (1996).
Lund, et al., "Oligosaccharide-protein interactions in IgG can modulate recognition by Fc gamma receptors," *Faseb J*, 9:115-119 (1995).
White, et al., "Antibody-targeted immunotherapy for treatment of malignancy," *Annu Rev Med*, 52:125-145 (2001).
Aase, A. et al. "The extended hinge region of IgG3 is not required for high phogocytic capacity mediated by Fc gamma receptors, but the heavy chains must be disulfide bonded," *Eur J Immunol.*, 23(7):1546-1551 (Jul. 1993).
Abadeh, S., et al., "Remodelling the oligosaccharide of human IgG antibodies: effects on biological activities," *Biochem Soc Trans.*, 25(4):S661 (Nov. 1997).

Akewanlop, C., et al., "Phagocytosis of Breast Cancer Cells Mediated by Anti-*MUC*-1 Monoclonal antibody, DF3, and Its Bispecific Antibody" *Cancer Research*, 61:4061-4065 (May 15, 2001).
Alegre, M., et al., "Effect of a Single Amino Acid Mutation on the Activating and Immunosuppressive Properties of a "Humanised" OKT3 Monoclonal Antibody," *J. Immunology*, 148:3461-3468 (Jun. 1992).
Amigorena, S., et al., "Fc receptors for IgG and antigen presentation on MHC class I and class II molecules" *Immunology*, 11:385-390 (1999).
Armour, K. L., et al., "Differential binding to human FcγRIIa and FcγRIIb receptors by human IgG wildtype and mutant antibodies," *Molecular Immunology*, 40:585-593 (2003).
Ashkenazi, A., et al., "Mapping the CD4 binding site for human immunodeficiency virus by alanine-scanning mutagenesis," *PNAS, USA*, 87:7150-7154 (Sep. 1990).
Bolland, S. "A Newly Discovered Fc Receptor tha Explains IgG-Isotype Disparities in Effector Responses," *J. Immunity*, 23:2-4 (Jul. 2005).
Boruchov, A. M., et al., "Activating and inhibitory IgG Fc receptors on human DCs mediate opposing functions" *J. Clin. Invest.* doi:10.1172/JCI24772 (Sep. 16, 2005).
Bowles, J. A., et al., "CD16 polymorphisms and NK activation induced by monoclonal antibody-coated target cells," *Journal of Immunological Methods*, pp. 1-12 (2005).
Brekke, O. H., et al., "Human IgG isotype-specific amino acid residues affecting complement-mediated cell lysis and phogocytosis," *Eur J. Immunl.*, 24(10):2542-5247 (Oct. 1994).
Brekke, O. H., et al., "Human IgG3 can adopt the disulfide bond pattern characteristic for IgG1 without resembling it in complement mediated cell lysis," *Mol. Immunol.* 30(16):1419-1425 (Nov. 1993).
Bruggeman, M., et al., "Comparison of the Effector Functions of Human Immunoglobulins Using a Matched Set of Chimeric Antibodies," *J. Exp. Med.*, 166:1351-1361 (Nov. 1987).
Bruggemann, M., et al., "A matched set of rat/mouse chimeric antibodies. Identification and biological properties of rat H chain constant regions mu, gamma 1, gamma 2a, gamma 2b, gamma 2c, epsilon, and alpha," *J. Immunol.*, 142(9):3145-3150 (May 1989).
Burmeister, W. P., et al., "Crystal structure of the complex of rat neonatal Fc receptor with Fc" *Nature*, 372:379-383 (Nov. 24, 1994).
Canfield, S. M., et al., "The Binding Affinity of Human IgG for its High Affinity Fc Receptor is Determined by Multiple Amino Acids in the $C_H2$ Domain and Is Modulated by the Hinge Region," *J. Exp. Med.*, 173:1483-1491 (Jun. 1991).
Caron, P. C., et al., "Engineered Humanized Dimeric Forms of IgG Are More Effective Antibodies," *J. Exp. Med.*, 176:1191-1195 (Oct. 1992).
Caron, P. C., et al., "Murine and humanized constructs of monoclonal antibody M19 (anti-CD33) for the therapy of acute myelogenous leukemia," *Cancer*, 73(3 Supp):1049-1056 (Feb. 1994).
Carpenter, P.A., et al., "Non-Fc Receptor-Binding Humanized Anti-CD3 Antibodies Induce Apoptosis of Activated Human T Cells," *Journal of Immunology*, 165:6205-6213 (2000).
Carter, P., et al., "Humanization of an anti-p185$^{HER2}$ antibody for human cancer therapy" *PNAS*, 89:4285-4289 (May 1992).
Cartron, G., et al., "Therapeutic activity of humanized anit-Cd20 monoclonal antibody and polymorphism in IgG Fc receptor FcγRIIIa gene," *Blood*, 99(3):754-758 (Feb. 1, 2002).
Chapman, P. B., "T-Cell Chauvinists Versus Antibody Advocates—Can't We All Just Get Along?" *J. Clin. Oncology*, 22(22):4446-4448 (Nov. 15, 2004).
Chappel, M. S., et al., "Identification of a Secondary Fcγ RI Binding Site within a Genetically Engineered Human IgG Actibody," *J. Biol. Chem.*, 268(33):25124-25131 (Nov. 1993).
Chappel, M. S., et al., "Identification of the Fcγ receptor class I binding site in human IgG through the use of recombinant IgG1/IgG2 hybrid and point-mutated antibodies," *PNAS, USA*, 88:9036-9040 (Oct. 1991).
Chintalacharuvu, K. R., et al., "Hybrid IgA2/IgG1 Antibodies with Tailor-Made Effector Functions," *Clinical Immunology*, 101(1):21-31—(Oct. 2001).

(56) References Cited

OTHER PUBLICATIONS

Clark, M. R., "Chemical Immunology Antibody Engineering IgG Effector Mechanisms," Dissertation submitted to Immunology Division of Department of Pathology at Cambridge University, UK (No Date).

Clynes, R. A., et al., "Inhibitory Fc receptors modulate in vivo cytotoxicity against tumor targets," *Nature Medicine*, 6(4):443-446 (Apr. 2000).

Clynes, R. et al., "Modulation of Immune complex-induced Inflammation In Vivo by the Coordinate Expression of Activation and Inhibitory Fc Receptors," *J. Exp. Med.*, 189(1):179-185 (Jan. 4, 1999).

Clynes, R., "Immune complexes as therapy for autoimmunity" *J. Clin. Invest.*, 115:25-27 (2005).

Clynes, R., et al., "Fc receptors are required in passive and active immunity to melanoma," *PNAS USA*, 95:652-656 (Jan. 1998).

Cohen-Sodal, J. FG., et al., "Review: Fc γ receptors" *Immunology Letts*, 92:199-205 (2004).

Cole, M. S., et al., "Human IgG2 variants of chimeric anti-CD3 are nonmitogenic to T cells," *J. Immunol.*, 159(7):3613-3621 (Oct. 1, 1997).

Coloma, M. J., et al., "The hinge as a spacer contributes to convalent assembly and is required for function of IgG," *J. Immunol.*, 158(2):733-740 (Jan. 15, 1997).

D'Uscio, C. H., et al., "Cellular cytotoxicity mediated by isotype-switch variants of a monoclonal antibody to human neuroblastoma," *Br. J. Cancer*, 64(3):445-450 (Sep. 1991).

Da Silveira, S. A., et al., "Complement Activation Selectively Potentiates the Pathogenicity of the IgG2 b and IgG3 Isotypes of a High Affinity Anti-Erythrocyte Autoantibody," *J. Exp. Med.*, 195(6):665-672 (Mar. 18, 2002).

Davis, R. S., et al., "Fc receptor homologs: newest members of a remarkably diverse Fc receptor gene family," *Imm. Revs*, 190:123-136 (2002).

Davis, R. S., et al., "Identification of a family of Fc receptor homologs with preferential B cell expression," *PNAS, USA*, 98(17):9772-9777 (Aug. 2001).

Delano, W. L., et al., "Convergent Solutions to Binding at a Protein-Protein Interface" *Science*, 287:1279-1283 (Feb. 18, 2000).

Dhodapkar, K.M., et al., "Antitumor Monoclonal Antibodies Enhance Cross-Presentation of Cellular Antigens and the Generation of Myeloma-specific Killer T-Cells by Dendritic Cells" *J. Exp Med.*, 195(1):125-133 (Jan. 7, 2002).

Dhodapkar, K.M., et al., "Recruiting dendritic cells to improve antibody therapy of cancer" *PNAS*, 102(18):6243-6244 (May 3, 2005).

Dhodapkar, K.M., et al., "Selective blockade of inhibitory Fcγ receptor enables human dendritic cell maturation with IL-12p70 production and immunity to antibody-coated tumor cells" *PNAS*, 102(8):2910-2915 (Feb. 22, 2005).

Dhodapkar, M. V., et al., "T cells from the tumor microenvironment of patients with progressive myeloma can generate strong, tumor-specific cytolytic responses to autologous, tumor-loaded dendritic cells" *PNAS*, 99(20):13009-13013 (Oct. 1, 2002).

Duncan, A. R., et al., "Localization of the binding site for the human high-affinity Fc receptor on IgG," *Nature*, 332:563-564 (Apr. 7, 1988).

Duncan, A. R., et al., "The binding site for C1q on IgG," *Nature* 332:738-740 (Apr. 21, 1988).

Edelman, G. M., et al., "The Covalent Structure of an Entire γG Immunoglobulin Molecule," *PNAS*, 63:78-85 (1969).

Ehrhardt, G. R. A., et al., "Th inhibitory potential of Fc receptor homolog 4 on memory B cells," *PNAS, USA*, 100(23):13489-13494 (Nov. 2003).

Ellison, J. W., et al. "The nucleotide sequence of a human immunoglobulin $C\gamma_1$ gene" *Nucleic Acids Research*, 10(13):4071-4079(1982).

Ernst, L. K., et al., "Molecular characterization of six variant Fcγ receptor class I (CD64) transcripts," *Molecular Immunology*, 35:943-954 (1998).

Facchetti, F., et al., "An unusual Fc receptor-related protein expressed in human centroblasts," *PNAS, USA*, 99(6):3776-3781 (Mar. 19, 2002).

Gaboriaud, C., et al., "The Crystal Structure of the Globular Head of Complement Protein C1q Provides a Basis for Its Versatile Recognition Properties," *J. Biol. Chem.*, 278(47):46974-46982 (2003).

Garman, S. C., et al., "Structure of the Fc fragment of human IgG bound to its high-affinity receptor FcεRIa," *Nature*, 406:259-266 (2000).

Getahun, A., et al., "IgG2a-Mediated Enhancement of Antibody and T Cell Responses and Its Relation to Inhibitory and Activating Fcγ Receptors," *J. of Immunology*, 172:5269-5276 (2004).

Ghazizadeh, S., et al., "Physical and Functional Association of Src-related Protein Tyrosine Kinases with FcRII in Monocytic THP-1 Cells," *J. Biol. Chem.*, 269(12):8878-B884 (Mar. 25, 1994).

Ghetie, V. et al., "FcRn: the MHC class I-related receptor that is more than an IgG transporter" *Immunology Today*, 18(12):592-598 (Dec. 1997).

Ghetie, V., et al., "Multiple Roles for the Major Histocompatibility Complex Class I-Related Receptor FcRn," *Annu. Rev. Immunol.* 18:739-766 (2000).

Gonzales, N. R., et al., "SDR grafting of a murine antibody using multiple human germline templates to minimize its immunogenicity," *Molecular Immunology*, 41:863-872 (2004).

Greenwood, J. "Molecular Recognition in the Structure and Assembly of Filamentous Bacteriphages," Dissertation submitted to the University of Cambridge (Oct. 1989).

Greenwood, J., et al., "Structural motifs involved in human IgG antibody effector functions," *Eur. J. Immunol.*, 23(5):1098-1104 (May 1993).

Greenwood, J., et al., "Dual Importance of Positive Charge in the C-Terminal Region of Filamentous Bacteriophage Coat Protein for Membrane Insertion and DNA-Protein Interaction in Virus Assembly, " *Virology*, 171:444-452 (1989).

Greenwood, J. et al., "Effector functions of matched sets of recombinant human IgG subclass antibodies," Dissertation submitted to Cambridge University, Cambridge, UK (Feb. 1993).

Greenwood, J., et al., "Engineering multiple-domain forms of the therapeutic antibody CAMPATH-1H: effects on complement lysis," *Ther Immunol.*, 1(5):247-255 (Oct. 1994).

Groh, V., et al., "Efficient cross-priming of tumor antigen specific T cells by dendritic cells sensitized with diverse anti-MICA opsonized tumor cells" *PNAS*, 102(18):6461-6466 (May 3, 2005).

Harrison, P. T., et al., "Domain swap chimeras to study the binding of IgG by Fc gamm RI, the high affinity receptor for IgG," *Biochem Soc Trans.*, 24(1):144S (Feb. 1996).

Hazenbos, W.L., et al., "Murine IgG1 complexes Trigger Immune Effector Functions Predominately via FcγRIII (CD16)," *J. of Immunology*, 161:3026-3032 (1998).

Henry, A. J., et al., "Participation of the N-Terminal of Cε3 in the Binding of Human IgE to Its High-Affinity Receptor FcεRI," *Biochemistry*, 36:15568-15578 (1997).

Hezareh, M., et al., "Effector Function Activities of a Panel of Mutants of a Broadly Neutralizing Antibody against Human Immunodeficiency Virus Type I," *Journal of Virology*, 75(24):12161-12168 (2001).

Hinton, P. R., et al., "Engineered human IgG Antibodies with Longer Serum Half-Lives in Primates," *J. Biol Chem.*, 279(8):6213-6216 (Feb. 20, 2004).

Idusogie, E. E., et al., "Engineered Antibodies with Increased Activity to Recruit Complement," *J. of Immunology*, 166:2571-2575 (2001).

Idusogie, E.E., et al., "Mapping of the C1q Binding Site on Rituxan, a Chimeric Antibody with a Human IgG1 Fc," *J. of Immunology*, 164:4178-4184 (2000).

Isaacs, J. D., "Improving Serotherapy with Monoclonal Antibodies" dissertation submitted to the University of Cambridge (Mar. 1991).

Isaacs, J. D., et al., "From bench to bedside: discovering rules for antibody design, and improving serotherapy with monoclonal antibodies," *Rheumatology*, 40:724-738 (2001).

(56) References Cited

OTHER PUBLICATIONS

Issacs, J. D., et al., "Therapy with Monoclonal Antibodies, II. The contribution of Fcγ Receptor binding and the Influenece of $C_H1$ and $C_H3$ Domains on In Vivo Effector Function," *J. of Immunology*, 161:3862-3869 (1998).
Issacs, J. D., et al., "Therapy with Monoclonal Antibodies: an in vivo model for the assessment of therapeutic potential," *J. Immunol.*, 148(10):3062-3071 (May 15, 1992).
Jefferis, R. et al., "Recognition sites on human IgG for Fc gamma receptors: the role of glycosylatin," *Immunol Letters*, 44(2-3):111-117 (Jan. 1995).
Jefferis, R., et al., "Interaction sites on human IgG-Fc for FcγR: current models," *Immunology Letts.*, 82:57-65 (2002).
Jefferis, R., et al., "Modulation of FcγR and human complement activation by IgG3-core oligosaccharide interactions," *Immunology Letters*, 54:101-104 (1996) and errata at *Immunology Letters*, 58:67 (1997).
Jefferis, R., et al. "Molecular definition of interaction sites on human IgG for Fc receptors (huFc gamma R)," *Mol Immunol.*, 27(12):1237-1240 (Dec. 1990).
Jendeberg, L., et al., "Engineering of $Fc_1$ and $Fc_3$ from human immunoglobulin G to analyse subclass specificity for staphylococcal protein A, "*Journal of Immunological Methods*, 201:25-34 (1997).
Junghans, R. P., et al., "The protection receptor for IgG catabolism is the $β_2$-microglobulin-containing neonatal intestinal transport receptor," *PNAS*, 93:5512-5516 (May 1996).
Kalergis, A.M., et al., "Inducing Tumor Immunity through the Selective Engagement of Activating Fcγ Receptors on Dendritic Cells" *J. Exp. Med.* 195(12):1653-1659 (Jun. 17, 2002).
Kan, K. S., et al., "Thioether-Bonded Constructs of Fabγ and Fcγ Modules Utilizing Differential Reduction of Interchain Disulfide Bonds," *Journal of Immunology*, 166:1320-1326 (2001).
Karassa, F. B., et al., "The role of FcγRIIA and IIIA polymorphisms in autoimmune diseases," *Biomedicine & Pharmacotherapy*, 58:286-291 (2004).
Kim, J. et al., "Mapping the site on human IgG for binding of the MHC class I-related receptor, FcRn" *Eur. J. Immunol.*, 29:2819-2825 (1999).
Kim, J. K. et al., "Localization of the site of the murine IgG1 molecule that is involved in binding to the murine intestinal Fc receptor," *Eur J Immunol.*, 24(10):2429-2439 (Oct. 1994).
Kim, J.K., et al., "Identifying amino acid residues that influence plasma clearance of murine IgG1 fragments by site-directed mutagenesis," *Eur J. Immunol.*, 24(3):542-548 (Mar. 1994).
Kim, T. D., et al., "Analysis of FcγRIII and IgG Fc Polymorphism Reveals Functional and Evolutionary Implications of Protein-Protein Interaction," *J. Mol. Evol.*, 53:1-9 (2001).
Kurucz, I., et al., "Bacterially expressed human FcγRIIb is soluble and functionally active after in vitro refolding" *Immunology Letts.*, 75:33-40 (2000).
Lund, J., et al., "A protein structural change in aglycosylated IgG3 correlates with loss of huFc gamma R1 and huFc gamma R111 binding and/or activation," *Mol. Immunol.*, 27(11):1145-1153 (Nov. 1990).
Lund, J., et al., "Control of IgG/Fc glycosylation: a comparision of oligosaccharides from chimeric human/mouse and mouse subclass immunoglobulin Gs," *Mol Immunol.*, 30(8):741-748 (Jun. 1993).
Maenaka, K., et al., "The Human Low Affinity Fcγ Receptors IIa, IIb and III Bind IgG with Fast Kinetics and Distinct Thermodynamic Properties" *J. Biol. Chem.*276(48):44898-44904 (2001).
Martin, W. L., et al., "Characterization of the 2:1 Complex between the Class I MHC-Related Fc Receptor and Its Fc Ligand in Solution," *Biochemistry*, 38:12639-12647 (1999).
Martin, W. L., et al., "Crystal Structure at 2.8 Å of an FcRn/Heterodimeric Fc Complex: Mechanism of pH-Dependent Binding" *Molecular Cell*, 7:867-877, Apr. 2001.
Masztalerz, A., et al., "Mechanisms of macrophage cytotoxicity in IL-2 and IL-12 mediated tumor regression," *Cancer Immunol Immunother*, 52:235-242 (2003).

Maxwell, K.F., et al., "Crystal structure of the human leukocyte Fc receptor, FcRIIa." *Nature Structural Biology*, 6(5):437-442 (May 1999).
Mayfield, S. P., et al., "Expression and assembly of a fully active antibody algae," *PNAS*, 100(2):438-442 (Jan. 21, 2003).
Mechetina, L. V., et al., "Identification of CD16-2, a novel mouse receptor homologous to CD16/FcγRIII," *Immunogenetics*, 4:463-468 (2002).
Merchant, A. M. et al., "An efficient route to human bispecific IgG," *Nat Biotechnol.*, 16(7):677-681 (1998).
Metes. D., et al., "Expression of Functional CD32 Molecules on Human NK Cells Is Determined by and Allelic Polymorphism of the Fcβ RIIC Gene," *Blood*, 91(7):2369-2380 (Apr. 1, 1998).
Michaelson, T. E., et al., "Antibody Dependent Cell-Mediated Cytotoxicity Induced by Chimeric Mouse-Human IgG Subclass and IgG3 Antibodies with Altered Hinge Region," *Molecular Immunology*, 29(3):319-326 (1992).
Michaelson, T. E., et al., "One disulfide bond in front of the second heavy chain constant region is necessary and sufficient for effector functions of human IgG3 without a genetic hinge," *PNAS*, 91:9243-9247 (Sep. 1994).
Michaelson, T. E., et al., "Primary Structure of the 'Hinge' Region of Human IgG3,"*J Biol Chem.*, 252(3):883-889 (Feb. 1977).
Miller, I., et al., "ITRAs: a new family of immunoglobulinlike receptors differentially expressed in B cells," *Blood*, 99(8):2662-2669 (Apr. 15, 2002).
Mimura, Y., et al., "Role of Oligosaccharide Residues of IgG1-Fc in Fcγ RIIb Binding," *J. Biol. Chem.*, 276(49):45539-45547 (Dec. 7, 2001).
Morgan, A., et al., "The N-terminal end of the CH2 domain of chimeric human IgG1 anti-HLA-DR is necessary for C1q, Fc gamma R1 and Fc gamma RIII binding," *Immunology*, 86(2):319-324 (Oct. 1995).
Nakamura, K., et al., "Dissection and optimization of immune effector functions of humanized anti-ganglioside GM2 monoclonal antibody," *Molecular Immunology*, 37:1035-1046 (2000).
Neidhardt-Berard, E., et al., "Dendritic cells loaded with killed breast cells induce differentiation of tumor-specific cytoxic T lymphocytes" *Breast Cancer Res.*, 6R322-R328 (Apr. 30, 2004).
Nimmerjahn, F., et al., "Divergent Immunoglobulin-G Subclass Activity Through Selective Fc Receptor Binding" *Science*, 310:1510 (2005).
Nimmerjahn, F., et al., "Fcγ RIV: A Novel FcR with Distinct IgG Subclass Specificity," *Immunity*, 23:41-51 (Jul. 2005).
Nimmerjahn, F., et al., "Supporting Online Material for: Divergent Immunoglobulin G Subclass Activity Through Selective Fc Receptor Binding" *Science*, 310:1510 (2005).
Niwa, R., et al., "Defucosylated Chimeric Anti-CC Chemokine Receptor 4 IgG1 with Enhanced Antibody-Dependnent Cellular cytotoxicity Shows Potent Therapeutic Activity to T-Cell Leukemia and Lymphoma," *Cancer Research*, 64:2127-2133 (Mar. 15, 2004).
Norderhaug, L., et al., "Chimeric mouse human IgG3 antibodies with an IgG4-like hinge region induce complement-mediated lysis more efficiently than IgG3 with normal hinge," *Eur J immunol.*, 21(10):2379-2384 (Oct. 1991).
O'Connor, S. J., et al., "Humanization of an antibody against human protein C and calcium-dependence involving framework residues," *Protein Engineering*, 11(4):321-328 (1998).
Ober, R. J. , et al., "Differences in promiscuity for antibody-FcRn interactions across species: implications for therapeutic antibodies," *International Immunology*, 13(12):1551-1559(2001).
Ober, R. J., et al., "Exocytosis of IgG as mediated by the receptor, FcRn: An analysis at the single-molecule level" *PNAS*, 101(30):11076-11081 (Jul. 27, 2004).
Okazaki, A., et al., "Fucose Depletion from Human IgG1 Oligosaccharide Enhances Binding Enthalpy and Association Rate Between IgG1 and Fcγ RIIIa," *J. Mol. Biol.*, 336:1239-1249 (2004).
Parren, P. W., et al., "Characterization of IgG FcR-mediated proliferation of human T-cells induced by mouse and human anti-CD3 monoclonal antibodies. Identification of a functional polymorphism to human IgG2 anti-CD3," *J. Immunol.*, 148(3):695-701 (Feb. 1992).
Parren, P.W., et al., "On the interaction of IgG subclasses with the low affinity Fc gamma RIIa (CD32) on human monocytes, neutrophils,

(56) References Cited

OTHER PUBLICATIONS and platelets. Analysis of a functional polymorphism to human IgG2," *J Clin Invest.*, 90(4):1537-1546 (Oct. 1992).
Pearce, K. H., et al., "Mutational Analysis of Thrombopoietin for Identification of Receptor and Neutralizing Antibody Sites," *J. Biol. Chem.*, 272(33):20595-20602 (1997).
Preithner, S., et al., "High concentrations of therapeutic Igg1 antibodies are needed to compensate for inhibition of antibody-dependnent cellular cytotoxicity by excess endogenous immunoglobulin G," *Molecular Immunology*, (2005).
Presta, L.G., et al., "Engineering therapeutic antibodies for improved function," *Biochemical Society Transactions*, 30(part 4):487-490 (2002).
Radaev, S., et al., "Recognition of IgG by Fcγ Receptor," *J. Biol. Chem.*, 276(19):16478-16483 (May 11, 2001).
Radaev, S., et al., "Review: Recognition of immunoglobulins by Fcγ recptors," *Molecular Immunology*, 38:1073-1083 (2001).
Radaev, S., et al., "The Structure of Human Type III Fcγ Receptor in Complex with Fc," *J. Biol. Chem.*, 276(19):16469-16477 (May 11, 2001).
Rafiq, K., et al., "Immune complex-mediated antigen presentation induces tumor immunity" *J. Clin. Invest.* 110:71-79 (2002).
Raghavan, M., et al., "Fc Receptors and Their Interactions with Immunoglobulins" *Annu. Rev. Cell Div. Biol.*, 12:181-220 (1996).
Ravetch, J. V., et al., "IgG Fc Receptors" *Annu. Rev. Immunol.*, 19:275-290 (2001).
Ravetch, J. V., et al., "Immune Inhibitory Receptors," *Science*, 290:84-89 (Oct. 6, 2000).
Ravetch, J.V., et al., "Fc Receptors," *Annu. Rev. Immunol.*, 9:457-492 (1991).
Reddy, P. R., et al., "Elimination of Fc Receptor-Dependent Effector Functions of a Modified IgG4 Monoclonal Antibody to Human CD4" *J. Immunol.*, 164:1925-1933 (2000).
Redpath, S., et al., "The Influence of the Hinge Region Length in Binding of Human IgG to Human Fcγ Receptors," *Human Immunology*, 59:720-727 (1998).
Rozsnyay, Z., et al., "Distinctive role of IgG1 and IgG3 isotypes in FcR-mediated functions," *Immunology*, 66(4):491-498 (Apr. 1989).
Sandlie, A.A., "The extended hinge region of IgG3 is not required for high phogocytic capacity mediated by Fc gamma receptors, but the heavy chains must be disulfide bonded," *Eur J. Immunol.* 23(7):1546-1551 (Jul. 1993).
Sarmay, G., et al., "Mapping and Comparison of the Interaction Sites on the Fc Region of IgG Responsible for Triggering Antibody Dependent Cellular Cytotoxicity (ADCC) Through Different Types of Human Fcγ Receptor," *Molecular Immunology*, 29(5):633-639 (1992).
Sautes-Fridman, C., et al., " Fc Gamma Receptors: A Magic Link with the Outside World," *ASHI Quarterly*, 148-151, (Fourth Quarter 2003).
Sensel, M. G., et al., "Amino Acid Differences in the N-Teminus of $C_H2$ Influence the Relative abilities of IgG2 and IgG3 to Activate Complement" *Mol. Immunol.*, 34(14):1019-1029 (1997).
Shields, R. L., et al., "High Resolution Mapping of the Binding Site on Human IgG1 for Fcγ RI, Fcγ RII, Fcγ RIII, and FcRn and Design of IgG1 Varients with Improved Binding to the Fcγ R" *J. Biol. Chem.*, 276(9):6591-6604 (2001).
Shields, R. L., et al., "Lack of Fucose on human IgG1 N-Linked Oligodaccharide Improves Binding to Human Fcγ RIII and Antibody-dependent Cellular Toxicity" *J. Biol. Chem.*, 277(30)26733-26740 (2002).
Shinkawa, T., et al., "The Absence of Fucose but Not the Presence of Galactose or Bisecting N-Acetylglucosamine of Human IgG1 complex-type Oligosaccharides Shows the Critical Role of Enhancing Antibody-dependent Cellular Cytotoxicity" *J. Biol. Chem.*, 278(5):3466-3473 (2003).
Shopes, B., "A genetically engineered human IgG mutant with enhanced cytolytic activity," *J Immunol.*, 148(9):2918-2922 (May 1992).
Shopes, B., et al., "Recombinant human IgG1-murine IgE chimeric Ig. Construction, expression, and binding to human Fc gamma receptors," *J. Immunol.*, 145(11):3842-3848 (Dec. 1, 1990).
Simmons, L. C., et al., "Expression of full-length immunoglobulins in *Esherichia coli*; rapid and efficient production of a glycosylated antibodies" *J. Immunol. Methods*, 263:133-147 (2002).
Smith, I. F. R., et al., "Addition of a μ-Tailpiece to IgG Results in Polymeric Antibodies with Enhanced Effector Functions Including Complement-Mediated Cytolysis by IgG4," *J. Immunology*, pp. 2226-2236 (1995).
Smith, K.G., et al., "T cell activation by anti-T3 antibodies: comparison of IgG1 and IgG2b switch variants and direct evidence for accessory function of macrophage Fc receptors," *Eur J Immunol.*, 16(5):478-486 (May 1986).
Sonderman, P. et al., "Crystal structure of the soluble form of the human Fcγ-receptor IIb: a new member of the immunoglobulin superfamily at 1.7Å resolution" *EMBO Journal*, 18(5):1095-1103 (1999).
Sonderman, P., et al., "Human Fcγ Receptor IIb Expressed in *Escherichia coli* Reveals IgG Binding Capability" *Biol. Chem.* 380:717-721 (Jun. 1999).
Sonderman, P., et al., "Molecular Basis for Immune Complex Recognition: A comparison of Fc-Receptor Structures" *J. Mol. Biol.*, 309:737-749 (2001).
Sonderman, P., et al., "The 3.2 -Å crystal structure of the human IgG1 Fc fragment—FcγRIII complex" *Nature*, 406:267-273 (Jul. 20, 2000).
Sorenson, V., et al., "Effect of the IgM and IgA secretory tailpieces on polymerization and secretion of IgM and IgG," *J Immunol.*, 156(8):2858-2865 (Apr. 1996).
Steplewski, Z., et al., "Biological activity of human-mouse IgG1, IgG2, IgG3, and IgG4 chimeric monoclonal antibodies with antitumor specificity," *PNAS USA*, 85:4852-4856 (Jul. 1988).
Stevenson, G. T., et al., "Preparation of Fcγ for addition to sulfhydryl-expressing ligands with minimal disturbance of the hinge," *J. of Immunological Methods*; 231:169-175 (1999).
Tao, M., et al., "Structural Features of Human immunoglobulin G that Determine Isotype-specific Differences in Complement Activation," *J. Exp. Med.* 178:661-667 (Aug. 1993).
Tao, M., et al., "The Differential Ability of Human IgG1 and IgG4 to Activate Complement is Determined by the COOH-terminal Sequence of the $C_H2$ domain" *J. Exp. Med*, 173:1025-1028 (Apr. 1991).
Thommesen, J. E., et al., "Lysine 322 in the human IgG3 $C_H2$ domain is crucial for antibody dependent complement activation" *Molecular Immunology*, 37:995-1014 (2000).
Tuijnman W. B., et al., "A flow cytometric rosetting assay for the analysis of IgG-Fc receptor interactions," *J Immunol Methods*, 127(2):207-214 (Mar. 1990).
Uchide, J. et al., "The Innate Mononuclear Phagocyte Network Depletes B Lymphocytes through Fc Receptor-dependent mechanisms during Anti-CD20 Antibody Immunotherapy" *J. Exp. Med.* 199(12):1659-1669 (Jun. 21, 2004).
Umana, P., et al., "Engineered gtycoforms of an antineuroblastoma IgG1 with optimized antibody-dependent cellular cytotoxic activity," *Nature Biotechnology*, 17:176-180 (1999).
Van Royen-Kerkhof, A, et al., "Flow cytometric determination of Fcγ RIIA (CD32) polymorphism," *J. lmmunol. Methods*, 294:135-144 (2004).
Van Schie, R.C.A.A., et al., "Evaluation of Human Fcγ RIIA (CD32) and Fcγ RIIIB (CD16) Polymorphisms in Caucasians and African-Americans Using Salivary DNA," *Clinical and Diagnostic Laboratory Immunology*, 7(4):676-681 (Jul. 2000).
Van Sorge, N. M., et al., "Fcγ R polymorphisms: Implications for function, disease and susceptibility and immunotherapy" *Tissue Antigens*, 63:189-202 (2003).
Vidarte, L., et al., "Serine 132 is the C3 Covalent Attachment Point of the CH1 domain of Human IgG1" *J. Biol. Chem.*, 276(41):38217-38223 (2001).
Ward, E. S., et al., "Evidence to support the cellular mechanism involved in serum IgG homeostatis in humans" *International Immunology*, 15(2):187-195 (2003).

(56) References Cited

OTHER PUBLICATIONS

Warmerdam, P. A., et al., "Interaction of a human Fc gamma RIIb1 (CD32) isoform with murine and human IgG subclasses," *Int Immunol.*, 5(3):239-247 (Mar. 1993).
Wawrzynczak, E. J., et al., "Recombinant mouse monoclonal antibodies with single amino acid substitutions affecting Clq and high affinity Fc receptor binding have identical serum half-lives in the BALB/c mouse," *Mol. Immunol.*, 29(2):221-227 (Feb. 1992).
Weiner, L. M., et al., "Tunable antibodies," *Nature Biotechnology*, 23(5):556-557 (May 2005).
Weng, W., et al., "Clinical Outcome of Lymphoma Patients After Idiotype Vaccination Is Correlated With Humoral Immune Response and Immunoglobulin G Fc Receptor Genotype," *J. Clin Oncol.*, 22(23):1-8 (2004).
Weng, W. et al., "Two Immunoglobulin G Fragment C Receptor Polymorphisms Independently Predict Response to Rituximab in Patients With Follicular Lymphoma," *Journal of Clinical Oncology*, 21(21):3940-3947 (Nov. 1, 2003).
West, A. P., et al., "Crystal Structure and immunoglobulin G Binding Properties of the Human Major Histocompatibility Complex-Related Fc Receptor," *Biochemistry*, 39:9698-9708 (2000).
Wing, M. G., et al., "Mechanism of First-Dose Cytokine-Release Syndrome of CAMPATH 1-H:Involvement of CD16 (FcγRIII) and CD11a/CD18 (LFA-1)on NK Cells," *J. Clin. Invest.*, 98(12):2819-2826 (Dec. 1996).
Wolff, E.A., et al., "Monoclonal antibody homodimers: enhanced antitumor activity in nude mice," *Cancer Res.*, 53(11):2560-2565 (Jun. 1, 1993).
Wright, A., et al., "Effect of C2-Associated carbohydrate Structure on Ig Effector Function: Studies with Chimeric Mouse-Human IgG1 Antibodies in Glycosylation Mutants of Chinese Hamster Ovary Cells" *J. of Immunology*, 160:3393-3402 (1998).
Wright, A., et al., "In vivo trafficking and catabolism of IgG1 antibodies with Fc associated carbohydrates of differing structure," *Glycobiology*, 10(12):1347-1355 (2000).
Xu, D., et al., "In Vitro Characterization of Five Humanized OKT3 Effector Function Varient Antibodies," *Cellular Immunology*, 200:16-26 (2000).
Xu, M., et al., "Molecular Cloning and Characterization of SPAP1, an Inhibitory Receptor," *Biochemical and Biophysical Research Communications*, 280:768-775 (2001).
Xu, Y., et al., "Residue at Position 331 in the IgG1 and IgG4 $C_H2$ Domains Contributes to Their Differential Ability to Bind and Activate Complement" *J. Biol. Chem.* 269(5):3469-3474 (1994).
Zelaschi, D., et al., "Human immunoglobulin allotypes: previously unrecognized determinants and alleles defined with monoclonal antibodies," *PNAS, USA*, 80:3762-3766 (Jun. 1983).
Zhou, H., et al., "DNA-based vaccines activate innate and adaptive antitumor immunity by engaging the NKG2D receptor" *PNAS*, 102(31):10846-10851 (Aug. 2, 2005).
Zhou, J., et al., "Generation of Mutated Variants of the Human Form of the MHC Class I-related Receptor, FcRn, with Increased Affinity for Mouse Immunoglobulin G,"*J. Mol. Biol.*, 332(4):901-13 (Sep. 2003).
Zhu, D., et al., "A novel human immunoglobulin Fc gamma Fc epsilon bifunctional fusion protein inhibits Fc epsilon RI-mediated degranulation," *Nat Med.*, 8(5):518-521 (May 2002).
Andreakos, E., et al., "Monoclonal antibodies in immune and inflammatory diseases," *Curr. Opin. Biotech.*, 13:615-620 (2002).
Carter, P., "Improving the Efficacy of Antibody-Based Cancer Therapies," *Nature Reviews*, 1:118-129 (2001).
Chadd, H., et al., "Therapeutic antibody expression technology," *Curr. Opin. Biotech.*, 12:188-194 (2001).
Clark, M. "Antibody humanization: a case of the Emperor's new clothes?" *Immunol. Today*, 21(8):397-402 (2000).
Cragg, M., et al., "Signaling antibodies in cancer therapy," *Curr. Opin. Immunol.*, 11:541-547 (1999).
Dall'Acqua, W., et al., "Antibody Engineering," *Curr. Opin Structural Biol.*, 8:443-450 (1998).

Glennie, M., et al., "Clinical trials of antibody therapy," *Immun. Today*, 21(8):403-410 (2000).
Glennie, M., et al., "Renaissance of cancer therapeutic antibodies," *Drug Discovery Today*, 8(11):503-510 (2003).
Hayhurst, A., et al., "High-throughput antibody isolation," *Curr. Opin. Chem. Biol.*, 5:683-689 (2001).
Hogarth, P., "Fc receptors are major mediators of antibody based inflammation in autoimmunity," *Curr. Opin. Immun.*, 14:798-802 (2002).
Holliger, P., et al., "Antibodies come back from the brink," *Nature Biotechnology*, 16:1015-1016 (1998).
Hudson, P., "Recombinant antibody constructs in cancer therapy," *Curr. Opin. Immunology*, 11:548-557 (1999).
Hudson, P., "Recombinant antibody fragments," *Curr. Opin in Biotechnology*, 9:395-402 (1998).
Johnson, G., et al., "Kabat Database and its applications: 30 years after the first variability plot," *Nucleic Acids Research*, 28(1):214-218 (2000).
Johnson, G., et al., "Kabat Database and its applications: future directions," *Nucleic Acids Research*, 29(1):205-206 (2001).
Maynard, J., et al., "Antibody Engineering," *Annu. Rev. Biomed. Eng.*, 2:339-376 (2000).
Morea, V., et al., "Antibody Modeling: Implications for Engineering and Design," *Methods*, 20:267-279 (2000).
Penichet, M., et al., "Antibody-cytokine fusion proteins for the therapy of cancer," *Journal of Immunological Methods*, 248:91-1010 (2001).
Reichert, J., "Monoclonal antibodies in the clinic," *Nature Biotechnology*, 19:819-822 (2001).
Thrush, G., et al., "Immunotoxins: An Update," *Ann. Rev. Immunol.*, 14:49-71 (1996).
Torphy, T., et al., "Pharmaceutical biotechnology Monoclonal antibodies: boundless potential, daunting challenges—Editorial Overview," *Curr. Opin. Biotechnol.*, 13:589-591 (2002).
Trail, P. et al., "Monoclonal antibody drug conjugates in the treatment of cancer" *Curr. Opin. Immunol.*, 11:584-588 (1999).
Trikha, M., "Monoclonal antibodies as therapeutics in oncology," *Curr. Opin. Biotech.*, 13:609-614 (2002).
Van Dijk, M., et al., "Human antibodies as next generation therapeutics," *Curr Opin. Chem. Biol.*, 5:368-374 (2001).
Van Sorge, N., et al., "Fcγ R polymorphisms: Implications for function, disease susceptibility and immunotherapy," *Tissue Antigens*, 61:189-202 (2003).
Vasserot, A., et al., "Optimization of protein therapeutics by directed evolution," *Drug Discovery Today*, 8(3):118-126 (2003).
Waldmann, T., et al., "Emerging Therapies: Spectrum of Application of Monoclonal Antibody Therapy," *Hemotology*, 394-408 (2000).
Artandi, et al. "Monoclonal IgM rheumatoid factors bind IgG at a discontinuous epitope comprised of amino acid loops from heavy-chain constant-region domains 2 and 3" Proc. Natl. Acad. Sci., 1992, 94-98, vol. 89.
Issacs, J.D. et al. Therapy with Monoclonal Antibodies, II. The Contribution of Fcγ Receptor Binding and the Influence of $C_H1$ and $C_H3$ Domains on In Vivo Effector Function[1] *Amer. Assn. Immunolgists* 1 (1998) pp. 3862-3869.
U.S. Appl. No. 10/339,788, Chirino et al.
Anderson, et al., "An expanded genetic code with a functional quadruplet codon" Proc. Nat. Acad. Sci., 2004, 7566-7571, vol. 101.
Atwell, et al."Stable Heterodimers from Remodeling the Domain Interface of a Homodimer using a Phage Display Library" J. Mol. Bioi, 1997,26-35, vol. 270.
Baca et al., "Antibody humanization using monovalent phage display," J Biol Chem. Apr. 18, 1997, 272(16):10678-84.
Bayry, et al "Mechanisms of action of intravenous immunoglobulins in autoimmune and inflammatory diseases" Transfusion Clinique et biologique, 2003,165-169, vol. 10, No. 3.
Beigier-Bompadre, et al "The Formyl Peptide N-Fornyl-methionly-leucyl-phenylalanine Downregulates the Expression of FcγRs in Interferon-y-Activated Monocytes/Macrophages In Vitro and In Vivo" Scand. J. Immunol., 2003, 221-228, vol. 57.
Binstadt, et al "IgG Fc receptor polymorphisms in human disease: Implications for C10 intravenous immunoglobulin therapy" J. Allergy and Clinical Immuno., (2003), 697-703, vol. 111, No. 4.

(56) References Cited

OTHER PUBLICATIONS

Bitonti, et al "Pulmonary delivery of an erythropoietin Fc fusion protein in non-human C11 primates through an immunoglobulin transport pathway" Proc. Natl. Acad. Sci., 2004, 9763-9768, vol. 101.
Bogan & Thorn, 1998, "Anatomy of Hot Spots in Protein Interfaces", *J. Mol. Biol.*, vol. 280, pp. 1-9.
Bruggemann, et al "Production of human antibody repertoires in transgenic mice" Current Opinion in Biotech., 1997,455-458, vol. 8.
Carter, et al., "Bispecific human IgG by design" J. Immunol. Methods, 2001, 7-15, vol. 248.
Chari, et al., "Immunoconjugates containing novel maytansinoids: Promising anticancer drugs" Cancer Res., 1992, 127-131, vol. 52.
Chin, et al "An Expanded Eukaryotic Genetic Code" Science, 2003, 964-967, vol. 301.
Clarkson & Wells, 1995, "A Hot Spot of Binding Energy in a Hormone-Receptor Interface", *Science* vol. 267, pp. 383-386.
Cobleigh, et al., "Multinational Study of the Efficacy and Safety of Humanized Anti-HER2 Monoclonal Antibody in Women who have HER2-Overexpressing Metastatic Breast Cancer that has progressed after chemotherapy for metastatic disease" J. Clin. Oncol., 1999, 2639-2648, vol. 17.
Cropp, et al., "An expanding genetic code" Trends in Genetics, 2004, 625-630,vol. 20, No. 12.
Cunningham & Wells, 1989, "High-Resolution Epitope Mapping of hGH-Receptor Interactions by Alanine—Scanning Mutagenesisi", *Dept. of Biomolecular Chemistry, Genentech*—Science vol. 244, pp. 1081-1085.
Dall'Ozzo, et al "Rituximab-Dependent Cytotoxicity by Natural Killer Cells: Influence of FCGR3A Polymorphism on the Concentration-Effect Relationship" Cancer Research, 2004, 4664-4669, vol. 64.
Dall'Acqua et al., "Properties of human IgG1s engineered for enhanced binding to the neonatal Fc receptor (FcRn)," J Biol Chem. Aug. 18, 2006, 281(33):23514-24.
Datta-Mannan et al., "Humanized IgG1 variants with differential binding properties to the neonatal Fc receptor: relationship to pharmacokinetics in mice and primates," Drug Metab Dispos. Jan. 2007, 35(1):86-94.
Datta-Mannan et al., "Monoclonal antibody clearance. Impact of modulating the interaction of IgG with the neonatal Fc receptor," J Biol Chem. Jan. 19, 2007, 282(3):1709-17.
De Pascalis, et al., "Grafting of "Abbreviated" Complementarity-Determining Regions Containing Specificity-Determining Residues Essential for Ligand Contact to Engineer a less Immunogenic Humanized Monoclonal Antibody" J. Immunol., 2002, 3076-3084, vol. 169.
Deisenhofer, et al., "Crystallographic Refinement and Atomic models of a Human Fc Fragment and Its Complex with Fragment B of Protein A from Staphylococcus aureus at 2.9- and 2.8 A resolution" Biochem. 1981, 2361-2370 vol. 20, No. 9.
Dickinson, et al., "Bidirectional FcRn-dependent IgG transport in a polarized human intestinal epithelial cell line" J. Clin. Invest., 1999, 903-911, vol. 104.
Doronina, et al, "Development of potent monoclonal antibody auristatin conjugates for cancer therapy" Nature Biotech., 2003, 778-784, vol. 21, No. 7.
Dove, et al, "Uncorking the biomanufacturing bottleneck" Nature Biotech., 2002, 777-779, vol. 20.
Dyer, et al., "Effects of CAMPATH-1 antibodies in vivo in patients with lymphoid malignancies: influence of antibody isotype" Blood, 1989, 1431-1439, vol. 73.
Eppstein, et al "Biological activity of liposome-encapsulated murine interferon y is mediated by a cell membrane receptor" Proc. Natl. Acad. Sci., 1985, 3688-3692, vol. 82.
Finkle, et al., "HER2-Targeted Therapy Reduces Incidence and Progession of Midlige Mammary Tumors in Female Murine Mammary Tumor Virus huHER2-Transgenic Mice" Clin. Cancer Res., 2004, 2499-2511, vol. 10.
Francisco, et al "cAC10-voMMAE, an anti-CD30-monomethyl auristatin E conjugate with potent and selective antitumor activity" Blood, 2003, 1458-1465, vol. 102, No. 4.
Friend, et al., "Reversal of allograft rejection using the monoclonal antibody, campath-1G" Transplant. Proceedings., 1991, 2253-2254, vol. 23, No. 4.
Gabizon, et al "Pharmacokinetics and Tissue Distribution of Doxorubicin Encapsulated in Stable Liposomes with Long Circulation Time" J. Natl. Cancer Inst., 1989, 1484-1488, vol. 18.
Garber, et al., " Biotech industry faces new bottleneck" Nature Biotech., 2001, 184-185, vol. 10.
Geneseq [Online] XP002407723, "Sequence of a recombinant human (rhu) tumor necrosis factor receptor TNRF/fc fusion protein", Oct. 7, 1994, Accession No. AAR51003.
Gerstner, et al., "Sequence plasticity in the antigen-binding site of a therapeutic anti-HER2 antibody" J. Mol. Biol., 2002, 851-862, vol. 321.
Gorman, et al., "Reshaping a therapeutic CD4 antibody" Proc. Natl. Acad. Sci., 1991, 4181-4185, vol. 88.
Griffiths, et al "Strategies for selection of antibodies by phage display" Current Opinion in Biotech, 1998, 102-108, vol. 9.
Guerois et al., 2002, Predicting Changes in the Stability of Proteins and Protein Complexes: A Study of More than 1000 Mutations, *J. Biol. Mol.* vol. 320, pp. 369-387.
Gurbaxani et al., "Analysis of a family of antibodies with different half-lives in mice fails to find a correlation between affinity for FcRn and serum half-life," Mol Immunol. Mar. 2006, 43(9):1462-73.
Hale, et al., "Improving the outcome of bone marrow transplantation by using CD52 monoclonal antibodies to prevent graft-versus-host disease and graft rejection" Blood, 1998, 4581-4590, vol. 92.
Hale, et al., "Synthetic peptide mimotope of the CAMPATH-1 (CD52) antigen, a small glycosylphospatidylinositol-anchored glycoprotein" Immunotech., 1995, 175-187, vol. 1.
Hale, et al., "The CAMPATH-1antigen (CDw2)" Tissue Antigens, 1990, 118-127, vol. 35, No. 3.
Hammer, et al., "Precise prediction of major histocompatibility complex class II-peptide interaction based on peptide side chain scanning" J. Exp. Med., 1994, 2353-2358, vol. 180.
He, et al., "Humanization and Pharmacokinetics of a Monoclonal antibody with specificity for both E- and P-selectin" J. Immunol., 1998, 1029-1035, vol. 160.
Hinman, et al "Preparation and Characterization of Monoclonal Antibody Conjugates of the Calicheamicins: A Novel and Potent Family of Antitumor Antibiotics" Cancer Research, 1993, 3336-3341, vol. 53.
Horton et al., 2008, "Potent In Vitro and In Vivo Activity of an Fc-Engineered Anti-CD19 Monoclonal Antibody against Lymphoma and Leukemia", Cancer Res., vol. 68 (19), pp. 8049-8057.
Hwang, et al, "Hepatic uptake and degradation of unilamellar sphingomyelin/ cholesterol liposomes: A kinetic study" Proc. Natl. Acad. Sci, 1980, 4030-4034, vol. 77, No. 7.
James, et al.,"1.9 A Structure of the Therapeutic Antibody CAMPATH-1H Fab in Complex with a Synthetic Peptide Antigen" J. Mol. Biol., 1999, 293-301, vol. 289.
Janin & Chothia, 1990, "The Structure of Protein-Protein Recognition Sites", *J. Bio. Chem*, 16207-16030.
Jefferis "Antibody therapeutics: isotype and glycoform selection" Expert Opin. Biol. Ther., 2007, 1401-1413, vol. 7(9).
Jones & Thornton, 1996, "Principles of protein-protein interactions", *PNAS*, vol. 93, pp. 13-20.
Jones, et al "Replacing the complementarity-determining regions in a human antibody with those from a mouse" Nature, 1986, 522-525 , vol. 321.
Jungbluth, et al., "A monoclonal antibody recognizing human cancers with amplification / overexpression of the human epidermal growth factor receptor" Proc. Natl. Acad. Sci., 2003, 639-644, vol. 100, No. 2.
Kenanova et al., "Tailoring the pharmacokinetics and positron emission tomography imaging properties of anti-carcinoembryonic antigen single-chain Fv-Fc antibody fragments," Cancer Res. Jan. 15, 2005, 65(2):622-31.

(56) References Cited

OTHER PUBLICATIONS

Kettleborough, et al. "Humanization of a mouse monoclonal antibody by CDR-grafting: the importance of framework residues on loop conformation" Protein Engin., 1991, 773-783, vol. 4, No. 7.

Kilmartin, et al "Rat Monoclonal Antitubulin Antibodies Derived by Using a New Nonsecreting Rat Cell Line" Mol. Biol., 1982, 576-582, vol. 93.

Kim et al., "Catabolism of the Murine IgG1 Molecule: Evidence that Both CH2-CH3 Domain Interfaces are Required for Persistence of IgG1 in the Circulation of Mice," Scand J. Immunol 1994 40:457-465 ("Kim 3").

Krauss, et al., "Specificity grafting of human antibody frameworks selected from a phage display library: generation of a highly stable humanized anit-CD22 single-chain Fv fragment" Protein Engineering, 2003, 753-759, vol. 16.

Little, et al., "Of mice and men: hybridoma and recombinant antibodies" Immunol. Today, 2000, 364-370, vol. 21.

Lo Conte et al., 1999, "The Atomic Structure of Protein-Protein Recognition Sites", *J. Mol. Biol.*, vol. 285, ps. 2177-2198.

Lode, et al "Targeted therapy with a novel enediyene antibiotic calichemamicin I effectively suppresses growth and dissemination of liver metastases in a syngeneic model of murine neuroblastoma" Cancer Research, 1998, 2925-2928, vol. 58.

Lowman, et al "Selecting high-affinity binding proteins by monovalent phage display" Biochemistry, 1991, 10832-10838, vol. 30, No. 45.

Mallios, et al., "Class II MHC quantitative binding motifs derived from a large molecular database with a versatile iterative stepwise discriminant analysis meta-algorithm" Bioinformatics, 1999, 432-439, vol. 15.

Mallios, et al., "Predicting class II MHC/peptide multi-level binding with an iterative stepwise discriminant analysis meta-algorithm" Bioinformatics, 2001, 942-948, vol. 17.

Marshall, et al., "Prediction of Peptide Affinity to HLA DRB1*0401" J. Immunol., 1995, 5927-5933, vol. 154.

Massey, "Catalytic antibodies catching on" Nature, 1987, 457-458, vol. 320.

Mateo, et al., "Humanization of a mouse monoclonal antibody that blocks the epidermal growth factor receptor: recovery of antagonistic activity" Immunotech., 1997, 71-81, vol. 3.

McLaughlin, et al., "Rituximab Chimeric Anti-CD20 Monoclonal Antibody Therapy for Relapsed Indolent Lymphoma: Half of Patients Respond to a Four-Dose Treatment Program" J. Clin. Oncol., 1998, 2825-2833, vol. 16.

Medesan et al., "Delineation of the Amino Acid Residures Involved in Transcytosis and Catabolism of Mouse IgG1," J Immunol 1997 158:2211-2217.

Modjtahedi, et al., "Antitumor Activity of Combinations of Antibodies Directed Against Different Epitopes on the Extracellular Domain of the Human EGF Receptor" Cell Biophyics, 1993, 129-146, vol. 22.

Modjtahedi, et al., "Phase I trial and tumour localization of the anti-EGFR monoclonal antibody ICR62 in head and neck or lung cancer" Bt. J. Cancer, 1996, 228-235, vol. 73.

Modjtahedi, et al., "Targeting of Cells Expressing Wild-Type EGFR and Type-III Mutant EGFR (EGFRVIII) by Anti-EGFR MAB ICR62: A Two-Pronged Attack for Tumour Therapy" Int. J. Cancer, 2003, 273-280, vol. 105.

Modjtahedi, et al., "The human EGF receptor as a target for cancer therapy: six new rat mAbs against the receptor on the breast carcinoma MDA-MB 468" Bt. J. Cancer, 1993, 247-253, vol. 67.

Morea, et al "Antibody structure, prediction and redesign" Biophysical Chem., 1997, 9-16, vol. 68.

Morrison et al., "Sequences in antibody molecules important for receptor-mediated transport into the chicken egg yolk," Molecular Immunology, vol. 38, Issue 8, Jan. 2002, pp. 619-625.

Murray et al., "The Functional Groups of Amino Acids Dictate their Chemical Reaction", Harper's Biochemistry, Nov. 9, 1993, pp. 24-28.

Murthy, et al., "Binding of an Antagonistic Monoclonal Antibody to an Intact and Fragmented DGFReceptor Polypeptide" Archives of Biochem and Biophys., 1987, 549-560, vol. 252, No. 2.

Newman, et al., "Primatization of recombinant antibodies for immunotherapy of human diseases: A Macaque/Human chimeric antibody against human CD4" Biotech., 1992, 1455-1460, vol. 10.

Otzen & Fersht, 1999, "Anlaysis of protein-protein interactions by mutagenesis: direct versus indirect effects", *Protein Engineering*, vol. 12, pp. 41-45.

Petkova et al., "Enhanced half-life of genetically engineered human IgG1 antibodies in a humanized FcRn mouse model: potential application in humorally mediated autoimmune disease," Int Immunol. Dec. 2006, 18(12):1759-69.

Pop et al., "The generation of immunotoxins using chimeric anti-CD22 antibodies containing mutations which alter their serum half-life," International Immunopharmacology, vol. 5, Issues 7-8, Jul. 2005, pp. 1279-1290.

Presta, et al., "Humanization of an Anti-Vascular Endothelial Growht Factor Monoclonal Antibody for the Therapy of Solid Tumors and Other Disorders" Cancer Res., 1997, 4593-4599, vol. 57.

Presta, L.G., et al., "Engineering Antibodies for Therapy" Curr. Pharma. Biotechnology, 2002, vol. 3, 237-256.

Queen, et al., "A humanized antibody that binds to the Interleukin 2 Receptor" Proc. Natl. Acad. Sci., 1989, 10029-10033, vol. 86.

Rader, et al.,"A phage display approach for rapid antibody humanization: Designed combinatorial V gene libraries" Proc. Natl. Acad. Sci., 1998, 8910-8915, vol. 95.

Reichmann et al., 2007, "Binding Hot Spots in the TEM1-BLIP Interface in Light of its Modular Architecture", *J. Mol. Biol.*, vol. 365, 663-679.

Reichmann et al., 2007, "The molecular architecture of protein-protein binding sites", Curr. Opn. Structc. Biol., vol. 17, pp. 67-76.

Richards et al., 2008, "Optimization of antibody bidning to FCγRIIa enhances macrophage phagocytosis of tumor cells", Mol. Cancer Ther., vol. 7(8), pp. 2517-2527.

Riechmann, et al., "Reshaping human antibodies for therapy" Nature, 1988, 323-327, vol. 332.

Rodeck, et al., "Interactions between growth factor receptors and corresponding monoclonal antibodies in human tumors" J. Cell Biochem., 1987, 315-320, vol. 35.

Roguska, et al., "Humanization of Murine monoclonal Antibodies through variable domain resurfacing" Proc. Natl. Acad. Sci., 1994, 969-973, vol. 91.

Rosok, et al., "A combinatorial library strategy for the rapid humanization of anticarcinoma BR96 Fab" J. Biol. Chem., 1996, 22611-22618, vol. 271, No. 37.

Samuelsson, et al "Anti-inflammatory activity of IVIG mediated through the inhibitory Fc receptor" Science, 2001, 484-486, vol. 291.

Sauer-Eriksson, et al., "Crystal structure of the C2 fragment of streptococcal protein G in complex with the Fc domain of human IgG" Structure, 1995, 265-278, vol. 3.

Schreiber & Fersht, 1995, "Energetics of Protein-Protein Interactions: Analysis of the Barnase-Barstar Interface by Single Mutations and Double Mutant Cycles", *J. Biol. Mol.*, vol. 248, pp. 478-486.

Simon, et al., "Peptoids: A modular approach to drug discovery" Proc. Natl. Acad. Sci., 1992, 9367-9371, vol. 89.

Smith, "Filamentous fusion phage: Novel expression vectors that display cloned antigens on the virion surface" Science, 1985, 1315-1317.

Spira et al., "Generation of biologically active anti-Cryptococcus neoformans IgG, IgE and IgA isotype switch variant antibodies by acridine orange mutagenesis," Clin Exp Immunol. Sep. 1996, 105(3):436-42.

Stella, et al., "Direceted Drug Delivery" 1985, The Humana Press, Inc.

Stevenson, et al "Engineered antibody for treating lymphoma" Recent Res. In Cancer Research, 2002, 105-112, vol. 159.

Sturniolo, et al., "Generation of tissue-specific and promiscuous HLA ligand databases using DNA microarrays and virtual HLA class II matrices" Nature Biotech., 1999, 555-561, vol. 17.

Tan, et al ""Superhumanized" Antibodies: Reduction of Immunogenic Potential by Complementarity-Determining Region Grafting

(56) References Cited

OTHER PUBLICATIONS with Human Germline Sequences: Application to an Anti-CD28" J.Immunol., 2002, 1119-1125, vol. 169.
Tashiro, et al., "Structures of bacterial immunoglobulin-binding domains and their complexes with immunoglobulins" Current Opinion Struct. Biol., 1995, 471-481, vol. 5.
Tsurushita, et al "Humanization of Monoclonal Antibodies" Molecular B Cells, 2004, 533-545.
Tutuncu, et al., "Fcγ receptor type IIIA polymorphisms influence treatment outcomes in patients with inflammatory arthritis treated with tumor necrosis factor a-blocking agents" Arthritis & Rheumatism, 2005, 2693-2696, vol. 52, vol. 9.
Vaccaro et al., "Divergent activities of an engineered antibody in murine and human systems have implications for therapeutic antibodies," Proc Natl Acad Sci U S A. Dec. 5, 2006, 103(49):18709-14.
Van Mirre, et al., "Monomeric IgG in intravenous Ig preparations is a functional antagonist of FcγRII and FcγRIIIb" J. Immunol., 2004, 332-339, vol. 173.
Verhoeyen, et al "Reshaping Human Antibodies: Grafting an Antilysozyme Activity" Science, 1988, 1534-1536, vol. 239, No. 4847.
Vitetta, et al., "Redesigning Nature's Posions to Create Anti-Tumor Reagents" Science, 1987 , 1098-1104, vol. 238.
White, et al., "Design and Expression of Poymeric Immunoglobulin Fusin Proteins: A Strategy for Targeting Low-Affinity Fcγ Receptors" Protein Expression and Purification, 2001, 446-455, vol. 21.
Wilman, et al., "Prodrugs in cancer chemotherapy" Action Cancer Guest Lecture, 615th meeting, Belfast, 1986, 375-382, vol. 14.
Wu, et al., "Humanization of a murine monoclonal antibody by simultaneous optimization of framework and CDR residues" J. Mol. Biol., 1999, 151-162, vol. 294.
Yoshida, et al "Human Neonatal Fc Receptor Mediates Transport of IgG into Lumina! Secretions for Delivery of Antigens to Mucosal Dendritic Cells" 2004, 769-783, vol. 20.
Young et al., 1997, "Characterization of the receptor binding determinants of granulocyte colony stimulating factor", Protein Science, vol. 6, pp. 1228-1236.
Zalevsky et al., 2009, "The impact of Fc Engineering on an anti-CD19 antibody: increased Fcγ receptor affinity enhances B-cell clearing in nonhuman primates", Blood, vol. 113 (16), pp. 3735-3743.
Zhang, et al "A new strategy for the synthesis of gylcoproteins" Science, 2004, 371-373, vol. 303.
Lance, "Crystal structure at 2.8 ANG of an FcRn/heterodimeric Fc complex: Mechanism of pH-dependent binding" Molecular Cell, 2001, 7;867-877.
Dall'Acqua, D. F., et al., "Increasing the Affinity of a Human IgG1 for the Neonatal Fc Receptor: Biological Consequences," Journal of Immunology, 169:5171-5180 (2002).
Clarkson, et al., "Sequence of Ovine Ig-Gamma-2 Constant Region Heavy Chain CDNA and Molecular Modelling of Ruminant IGG Isotypes" Molecular Immuno., 1993, 30;1195-1204.
Bernstein, et al. "Nucleotide sequence of a rabbit IgG heavy chain from the recombinant F-I haplotype" Immunogenetics, 1983, 18;387-39.
Ober, R. J. , et al., "Differences in promiscuity for antibody-FcRn interactions across species: implications for therapeutic antibodies," International Immunology, 13(12):155.
Shields, "High Resolution Mapping of the Binding Site on Human IgG1 for Fc RI, Fc RII, Fc RIII, and FcRn and Design of IgG1 Varients with Improved Binding to the Fc R" J. Biol. Chem., 276(9):6591-6604 (2001).
Ghetie, V., et al., "Increasing the serum persistence of an IgG fragment random mutagenesis," Nat. Biotechol., 15(7):637-640 (Jul. 1997).
Hinton, P. R., et al.,"An Engineered Human IgG1 Antibody with Longer Serum Half-Life" J. of Immuno., 2006, 176;346-356.
Roopenian et al. "FcRn: the neonatal Fc Receptor comes of age" Nature Reviews, Immuno, 2007, 7:7; 715-725.
Bastida-Corcuera, et al., "Differential complement activation by bovine IgG2 allotypes" Veterinary Immunology and Immunopathology, 1999, vol. 71 No. 2, 115-123.
Burton, et al. "Immunoglobulin G: Functional sites", Molecular Immunology, vol. 22, No. 3, (Mar. 1985).

Chan, et al. "Variable Region Domain Exchange in Human IgGs promotes antibody complex formation with accompanying structural changes and altered effector functions" Molecular Immunology 2004, 21:527-538.
Chirino, A.J. et al."Minimizing the immunogenicity of protein therapeutics", Drug Discovery Today, 2004, vol. 9, No. 2, pp. 82-90.
Cole, M.S., et al., "HUM291, a Humanized Anti-CD3 Antibody, is immunosuppressive to T cells while exhibiting reduced mitogenicity in vitro", Transplantation, vol. 68, No. 4, pp. 563-571 (1999).
Dahiyat, B. I. et al. "Protein Design Automation", Protein Science, 1996, vol. 5, No. 5, ps. 895-903.
Dall'Acqua, W. et al. "Modulation of the Effector Functions of a Human IgG1 through Engineering of Its Hinge Region", 2006, J. Immunology, 177:1129-1138.
Hayes R.J. et al. "Combining computational and experimental screening for rapid optimization of protein properties", PNAS, 2002, vol. 99, No. 25, pp. 15926-15931.
Kabat et al., NIH Pub. No. 91-3242, p. 679-687 (1991).
Kato, K. et al., "Analysis of IgG-FcgammaR interactions in solution: Mapping of the FcgammaR binding site and evidence for a conformational change occurring in the Fc region", Immunology Letters, vol. 73, No. 2-3 (2000).
Lazar, et al. "Engineered antibody Fc variants with enhanced effector function" PNAS, 2006, 4005-4010.
Liu, et al. "Production of a Mouse-Human Chimeric Monoclonal Antibody to CD20 with Potent Fc-Dependent Biologic Activity" The Journal of Immunology, 1998, 139-10:3521-3526.
Medesan, et al. "Comparative studies of rat IgG to further delineate the Fc:FcRn interaction site" Eur.J. Immunol. (1998) 28:2092-2100.
Morrison, et al. "Variable Region Domain Exchange Influences the Functional Properties of IgG$^1$"The Journal of Immunology 1998, 160:2802-2808.
Natsume, A. et al. "Engineered Antibodies of IgG1/IgG3 Mixed Isotype with Enhanced Cytotoxic Activities", 2008, Cancer Research, 68:(10) pp. 3863-3871.
Pendley C. et al., "Immunogencity of therapeutic monoclonal antibodies", Current Opinion in Molecular Therapeutics, 2003, vol. 5, No. 2, pp. 172-179.
Shitara et al. "A new vector for the high level expression of chimeric antibodies in myeloma cells" J. of Immunological Methods, 1994, 167: 271-278.
Tamm, A. et al., "IgG Binding Sites on Human Fcγ Receptors" 1997, International Reviews of Immunology, 16:1,57-85.
Valerius, T. et al., "Fcalpha RI (CD89) as a Novel Trigger Molecule for Bispecific Antibody Therapy" Blood, 1997, 90:4485-4492.
Vitetta, E., et al., "Considering Therapeutic Antibodies", Science, 2006, vol. 313, pp. 308-309.
WHO Review of the notation for the allotypic and related markers of human immunoglobulins. J Immunogen 1976, 3:357-362.
WHO Review of the notation for the allotypic and related markers of human immunoglobulins. 1976, Eur. J. Immunol. 6, 599-601.
Wines, B.D. et al. "The IgG Fc contains distinct Fc receptor (FcR) binding sites: the leukocyte receptors Fc[gamma] RIIa bind to a region in the Fc distinct from that recognized by neonatal FcR and protein A" Journal of Immunology, (2000), pp. 5313-5318.
Woof, J.M. et al. "Localisation of the Monocyte-Binding Region on Human Immunoglobulin G" Molecular Immunology, 1986, vol. 23, No. 3, pp. 319-330.
Yamane-Ohnuki N. et al., "Establishment of FUT8 knockout chinese hamster ovary cells: an ideal host cell line for producing completely defucosylated antibodies with enhanced antibody-dependent cellular cytoxicity", Biotechnology and Bioengineering Interscience Publishers, London, GB, vol. 87, No. 5, Sep. 5, 2004.
GenBank [Online] XP002665294, "IgG1 heavy chain [Felis catus]", Apr. 10, 2002, Database Accession No. BAA32229.
Wagner et al., "Evolution of the six-horse IGHG genes and corresponding immunoglobulin gamma heavy chains.", 2002 Immunogenetics; 54:353-364.
Reff et al., A review of modifications to recombinant antibodies: attempt to increase efficacy in oncology applications, Critical Review Oncology Hematology, 2001 40:25-35.

\* cited by examiner

| | Hinge Region | | | | | | | | | | | | | Fc Region -> | | |
|---|---|---|---|---|---|---|---|---|---|---|---|---|---|---|---|---|

| | EU | 221 | 222 | 223 | 224 | 225 | 226 | 227 | 228 | 229 | 230 | 231 | 232 | 233 | 234 | 235 | 236 |
|---|---|---|---|---|---|---|---|---|---|---|---|---|---|---|---|---|---|
| SEQ ID NO:1 | IgG1 | D | - | - | K | T | H | T | C | P | P | C | P | A | P | E | L | L | G |
| 2 | IgG2 | - | | | V | - | E | - | | | | | | | P | V | A | - |
| 3 | IgG3 | L | G | D | T | | | | | R | | | | | | | | |
| 4 | IgG4 | - | | | - | - | P | P | | S | | | | | F | | | |

CH2 Domain

| EU | 237 | 238 | 239 | 240 | 241 | 242 | 243 | 244 | 245 | 246 | 247 | 248 | 249 | 250 | 251 | 252 | 253 | 254 | 255 | 256 | 257 | 258 | 259 | 260 | 261 | 262 | 263 |
|---|---|---|---|---|---|---|---|---|---|---|---|---|---|---|---|---|---|---|---|---|---|---|---|---|---|---|---|
| IgG1 | G | P | S | V | F | L | F | P | P | K | P | K | D | T | L | M | I | S | R | T | P | E | V | T | C | V | V |
| IgG2 | | | | | | | | | | | | | | | | | | | | | | | | | | | |
| IgG3 | | | | | | | | | | | | | | | | | | | | | | | | | | | |
| IgG4 | | | | | | | | | | | | | | | | | | | | | | | | | | | |

| EU | 264 | 265 | 266 | 267 | 268 | 269 | 270 | 271 | 272 | 273 | 274 | 275 | 276 | 277 | 278 | 279 | 280 | 281 | 282 | 283 | 284 | 285 | 286 | 287 | 288 | 289 | 290 |
|---|---|---|---|---|---|---|---|---|---|---|---|---|---|---|---|---|---|---|---|---|---|---|---|---|---|---|---|
| IgG1 | V | D | V | S | H | E | D | P | E | V | K | F | N | W | Y | V | D | G | V | E | V | H | N | A | K | T | K |
| IgG2 | | | | | | | | | | | Q | | | | | | | | | | | | | | | | |
| IgG3 | | | | | | | | | | | Q | | K | | | | | | | | | | | | | | |
| IgG4 | | | | | | Q | | | | | Q | | | | | | | | | | | | | | | | |

| EU | 291 | 292 | 293 | 294 | 295 | 296 | 297 | 298 | 299 | 300 | 301 | 302 | 303 | 304 | 305 | 306 | 307 | 308 | 309 | 310 | 311 | 312 | 313 | 314 | 315 | 316 | 317 |
|---|---|---|---|---|---|---|---|---|---|---|---|---|---|---|---|---|---|---|---|---|---|---|---|---|---|---|---|
| IgG1 | P | R | E | E | Q | Y | N | S | T | Y | R | V | V | S | V | L | T | V | L | H | Q | D | W | L | N | G | K |
| IgG2 | | | | | | F | | | | F | | | | | | | | | V | | | | | | | | |
| IgG3 | | | | | | F | | | | | | | | | | | | | | | | | | | | | |
| IgG4 | | | | | | F | | | | | | | | | | | | | | | | | | | | | |

| EU | 318 | 319 | 320 | 321 | 322 | 323 | 324 | 325 | 326 | 327 | 328 | 329 | 330 | 331 | 332 | 333 | 334 | 335 | 336 | 337 | 338 | 339 | 340 |
|---|---|---|---|---|---|---|---|---|---|---|---|---|---|---|---|---|---|---|---|---|---|---|---|
| IgG1 | E | Y | K | C | K | V | S | N | K | A | L | P | A | P | I | E | K | T | I | S | K | A | K |
| IgG2 | | | | | | | | | | G | | | | | | | | | | | | T | |
| IgG3 | | | | | | | | | | | | | | | | | | | | | | T | |
| IgG4 | | | | | | | | | G | | | S | S | | | | | | | | | | |

CH3 Domain

| EU | 341 | 342 | 343 | 344 | 345 | 346 | 347 | 348 | 349 | 350 | 351 | 352 | 353 | 354 | 355 | 356 | 357 | 358 | 359 | 360 | 361 | 362 | 363 | 364 | 365 | 366 | 367 |
|---|---|---|---|---|---|---|---|---|---|---|---|---|---|---|---|---|---|---|---|---|---|---|---|---|---|---|---|
| IgG1 | G | Q | P | R | E | P | Q | V | Y | T | L | P | P | S | R | D | E | L | T | K | N | Q | V | S | L | T | C |
| IgG2 | | | | | | | | | | | | | | | | E | | M | | | | | | | | | |
| IgG3 | | | | | | | | | | | | | | | | E | | M | | | | | | | | | |
| IgG4 | | | | | | | | | | | | | | | | Q | E | M | | | | | | | | | |

*FIG. 2a*

| EU | 368 | 369 | 370 | 371 | 372 | 373 | 374 | 375 | 376 | 377 | 378 | 379 | 380 | 381 | 382 | 383 | 384 | 385 | 386 | 387 | 388 | 389 | 390 | 391 | 392 | 393 | 394 |
|---|---|---|---|---|---|---|---|---|---|---|---|---|---|---|---|---|---|---|---|---|---|---|---|---|---|---|---|
| IgG1 | L | V | K | G | F | Y | P | S | D | I | A | V | E | W | E | S | N | G | Q | P | E | N | N | Y | K | T | T |
| IgG2 | | | | | | | | | | | | | | | | | | | | | | | | | | | |
| IgG3 | | | | | | | | | | | | | | | | | S | | | | | | | | N | | |
| IgG4 | | | | | | | | | | | | | | | | | | | | | | | | | | | |

| EU | 395 | 396 | 397 | 398 | 399 | 400 | 401 | 402 | 403 | 404 | 405 | 406 | 407 | 408 | 409 | 410 | 411 | 412 | 413 | 414 | 415 | 416 | 417 | 418 | 419 | 420 | 421 |
|---|---|---|---|---|---|---|---|---|---|---|---|---|---|---|---|---|---|---|---|---|---|---|---|---|---|---|---|
| IgG1 | P | P | V | L | D | S | D | G | S | F | F | L | Y | S | K | L | T | V | D | K | S | R | W | Q | Q | G | N |
| IgG2 | | | M | | | | | | | | | | | | | | | | | | | | | | | | |
| IgG3 | | | M | | | | | | | | | | | | | | | | | | | | | | | | |
| IgG4 | | | | | | | | | | | | | | | R | | | | | | | | | | E | | |

| EU | 422 | 423 | 424 | 425 | 426 | 427 | 428 | 429 | 430 | 431 | 432 | 433 | 434 | 435 | 436 | 437 | 438 | 439 | 440 | 441 | 442 | 443 | 444 | 445 | 446 | 447 |
|---|---|---|---|---|---|---|---|---|---|---|---|---|---|---|---|---|---|---|---|---|---|---|---|---|---|---|
| IgG1 | V | F | S | C | S | V | M | H | E | A | L | H | N | H | Y | T | Q | K | S | L | S | L | S | P | G | K |
| IgG2 | | | | | | | | | | | | | | | | | | | | | | | | | | |
| IgG3 | I | | | | | | | | | | | | | R | F | | | | | | | | | | | |
| IgG4 | | | | | | | | | | | | | | | | | | | | | | | L | | | |

FIG. 2b

|  |  |  | 237 | 238 | 239 | 240 | 241 | 242 | 243 | 244 | 245 | 246 | 247 | 248 | 249 | 250 | 251 | 252 | 253 |
|---|---|---|---|---|---|---|---|---|---|---|---|---|---|---|---|---|---|---|---|
| SEQ ID NO:5 | Fc Human | 1DN2.pdb Chain A | G | P | S | V | F | L | F | P | P | K | P | K | D | T | L | M | I |
| 6 | Fc Rat | 1I1A.pdb Chain C | - | - | S | V | F | [I] | F | P | P | K | [T] | K | D | [V] | L | [T] | I |

|  |  |  | 254 | 255 | 256 | 257 | 258 | 259 | 260 | 261 | 262 | 263 | 264 | 265 | 266 | 267 | 268 | 269 | 270 |
|---|---|---|---|---|---|---|---|---|---|---|---|---|---|---|---|---|---|---|---|
|  | Fc Human | 1DN2.pdb Chain A | S | R | T | P | E | V | T | C | V | V | V | D | V | S | H | E | N |
|  | Fc Rat | 1I1A.pdb Chain C | [T] | [L] | T | P | [K] | V | T | C | V | V | V | D | [I] | S | [Q] | [N] | [D] |

|  |  |  | 271 | 272 | 273 | 274 | 275 | 276 | 277 | 278 | 279 | 280 | 281 | 282 | 283 | 284 | 285 | 286 | 287 |
|---|---|---|---|---|---|---|---|---|---|---|---|---|---|---|---|---|---|---|---|
|  | Fc Human | 1DN2.pdb Chain A | P | E | V | K | F | N | W | Y | V | D | G | V | E | V | H | N | A |
|  | Fc Rat | 1I1A.pdb Chain C | P | E | V | [R] | F | [S] | W | [F] | [I] | D | [D] | V | E | V | H | [T] | A |

|  |  |  | 288 | 289 | 290 | 291 | 292 | 293 | 294 | 295 | 296 | 297 | 298 | 299 | 300 | 301 | 302 | 303 | 304 |
|---|---|---|---|---|---|---|---|---|---|---|---|---|---|---|---|---|---|---|---|
|  | Fc Human | 1DN2.pdb Chain A | K | T | K | P | R | E | E | Q | Y | N | S | T | Y | R | V | V | S |
|  | Fc Rat | 1I1A.pdb Chain C | [Q] | T | [H] | [A] | [P] | E | [K] | Q | [S] | N | S | T | [L] | R | [S] | V | S |

|  |  |  | 305 | 306 | 307 | 308 | 309 | 310 | 311 | 312 | 313 | 314 | 315 | 316 | 317 | 318 | 319 | 320 | 321 |
|---|---|---|---|---|---|---|---|---|---|---|---|---|---|---|---|---|---|---|---|
|  | Fc Human | 1DN2.pdb Chain A | V | L | T | V | L | H | Q | D | W | L | N | G | K | E | Y | K | C |
|  | Fc Rat | 1I1A.pdb Chain C | [E] | L | [P] | [I] | [V] | H | [R] | D | W | L | N | G | K | [T] | [F] | K | C |

|  |  |  | 322 | 323 | 324 | 325 | 326 | 327 | 328 | 329 | 330 | 331 | 332 | 333 | 334 | 335 | 336 | 337 | 338 |
|---|---|---|---|---|---|---|---|---|---|---|---|---|---|---|---|---|---|---|---|
|  | Fc Human | 1DN2.pdb Chain A | K | V | S | N | K | A | L | P | A | P | I | E | K | T | I | S | K |
|  | Fc Rat | 1I1A.pdb Chain C | K | V | [N] | [S] | [G] | A | [F] | P | A | P | I | E | K | [S] | I | S | K |

|  |  |  | 339 | 340 | 341 | 342 | 343 | 344 | 345 | 346 | 347 | 348 | 349 | 350 | 351 | 352 | 353 | 354 | 355 |
|---|---|---|---|---|---|---|---|---|---|---|---|---|---|---|---|---|---|---|---|
|  | Fc Human | 1DN2.pdb Chain A | A | K | G | Q | P | R | E | P | Q | V | Y | T | L | P | P | S | R |
|  | Fc Rat | 1I1A.pdb Chain C | [P] | [E] | G | [T] | P | R | [G] | P | Q | V | Y | T | [M] | [A] | P | [P] | [K] |

|  |  |  | 356 | 357 | 358 | 359 | 360 | 361 | 362 | 363 | 364 | 365 | 366 | 367 | 368 | 369 | 370 | 371 | 372 |
|---|---|---|---|---|---|---|---|---|---|---|---|---|---|---|---|---|---|---|---|
|  | Fc Human | 1DN2.pdb Chain A | E | E | M | T | K | N | Q | V | S | L | T | C | L | V | K | G | F |
|  | Fc Rat | 1I1A.pdb Chain C | E | E | M | T | [Q] | [S] | Q | V | S | [I] | T | C | [M] | V | K | G | F |

|  |  |  | 373 | 374 | 375 | 376 | 377 | 378 | 379 | 380 | 381 | 382 | 383 | 384 | 385 | 386 | 387 | 388 | 389 |
|---|---|---|---|---|---|---|---|---|---|---|---|---|---|---|---|---|---|---|---|
|  | Fc Human | 1DN2.pdb Chain A | Y | P | S | D | I | A | V | E | W | E | S | N | G | Q | P | E | N |
|  | Fc Rat | 1I1A.pdb Chain C | Y | P | [P] | D | I | [Y] | [T] | E | W | [K] | [M] | N | G | Q | P | [Q] | [E] |

|  |  |  | 390 | 391 | 392 | 393 | 394 | 395 | 396 | 397 | 398 | 399 | 400 | 401 | 402 | 403 | 404 | 405 | 406 |
|---|---|---|---|---|---|---|---|---|---|---|---|---|---|---|---|---|---|---|---|
|  | Fc Human | 1DN2.pdb Chain A | N | Y | K | T | T | P | P | V | L | D | S | D | G | S | F | F | L |
|  | Fc Rat | 1I1A.pdb Chain C | N | Y | K | [N] | T | P | P | [T] | [M] | D | [T] | D | G | S | [Y] | F | L |

|  |  |  | 407 | 408 | 409 | 410 | 411 | 412 | 413 | 414 | 415 | 416 | 417 | 418 | 419 | 420 | 421 | 422 | 423 |
|---|---|---|---|---|---|---|---|---|---|---|---|---|---|---|---|---|---|---|---|
|  | Fc Human | 1DN2.pdb Chain A | Y | S | K | L | T | V | D | K | S | R | W | Q | Q | G | N | V | F |
|  | Fc Rat | 1I1A.pdb Chain C | Y | S | K | L | [N] | V | [K] | K | [E] | [T] | W | Q | Q | G | N | [T] | F |

|  |  |  | 424 | 425 | 426 | 427 | 428 | 429 | 430 | 431 | 432 | 433 | 434 | 435 | 436 | 437 | 438 | 439 | 440 |
|---|---|---|---|---|---|---|---|---|---|---|---|---|---|---|---|---|---|---|---|
|  | Fc Human | 1DN2.pdb Chain A | S | C | S | V | M | H | E | A | L | H | N | H | Y | T | Q | K | S |
|  | Fc Rat | 1I1A.pdb Chain C | [T] | C | S | V | [L] | H | E | [G] | L | H | N | H | [H] | T | [E] | K | S |

|  |  |  | 441 | 442 | 443 |
|---|---|---|---|---|---|
|  | Fc Human | 1DN2.pdb Chain A | L | S | L |
|  | Fc Rat | 1I1A.pdb Chain C | L | S | [H] |

FIG. 3

| | | AA Number | 1EXU.pdb | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| SEQ ID NO:7 | FcRn Human Heavy Chain | 1EXU.pdb Chain A | | H | L | S | L | L | Y | H | L | T | A | V | S | S |
| 8 | FcRn Rat Heavy Chain | 1I1A.pdb Chain A | | [-] | L | [P] | L | [M] | Y | H | L | [A] | A | V | S | [D] |

| 17 | 18 | 19 | 20 | 21 | 22 | 23 | 24 | 25 | 26 | 27 | 28 | 29 | 30 | 31 | 32 | 33 | 34 | 35 | 36 |
|---|---|---|---|---|---|---|---|---|---|---|---|---|---|---|---|---|---|---|---|
| P | A | P | G | T | P | A | F | W | V | S | G | W | L | G | P | Q | Q | Y | L |
| [L] | [S] | [T] | G | [L] | P | [S] | F | W | [A] | [T] | G | W | L | G | [A] | Q | Q | Y | L |

| 37 | 38 | 39 | 40 | 41 | 42 | 43 | 44 | 45 | 46 | 47 | 48 | 49 | 50 | 51 | 52 | 53 | 54 | 55 | 56 |
|---|---|---|---|---|---|---|---|---|---|---|---|---|---|---|---|---|---|---|---|
| S | Y | N | S | L | R | G | E | A | E | P | C | G | A | W | - | - | - | - | - |
| [T] | Y | N | [N] | L | R | [Q] | E | A | [D] | P | C | G | A | W | [I | W | E | N | Q] |

| 57 | 58 | 59 | 60 | 61 | 62 | 63 | 64 | 65 | 66 | 67 | 68 | 69 | 70 | 71 | 72 | 73 | 74 | 75 | 76 |
|---|---|---|---|---|---|---|---|---|---|---|---|---|---|---|---|---|---|---|---|
| - | - | - | Y | W | E | K | E | T | T | D | L | R | I | K | E | K | L | F | L |
| [V | S | W] | Y | W | E | K | E | T | T | D | L | [K | S] | K | E | [Q] | L | F | L |

| 77 | 78 | 79 | 80 | 81 | 82 | | | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|
| E | A | F | K | A | L | - | - | G | G | K | G | P | Y | T | L | Q | G | L | L |
| E | A | [I] | [R] | [T] | L | [E | N | Q | I | N] | G | [T | F] | T | L | Q | G | L | L |

| 95 | 96 | 97 | 98 | 99 | 100 | 101 | 102 | 103 | 104 | 105 | 106 | 107 | 108 | 109 | 110 | 111 | 112 | 113 | 114 |
|---|---|---|---|---|---|---|---|---|---|---|---|---|---|---|---|---|---|---|---|
| G | C | E | L | G | P | D | N | T | S | V | P | T | A | K | F | A | L | N | G |
| G | C | E | L | [A] | P | D | N | [S] | S | [L] | P | T | A | [V] | F | A | L | N | G |

| 115 | 116 | 117 | 118 | 119 | 120 | 121 | 122 | 123 | 124 | 125 | 126 | 127 | 128 | 129 | 130 | 131 | 132 | 133 | 134 |
|---|---|---|---|---|---|---|---|---|---|---|---|---|---|---|---|---|---|---|---|
| E | E | F | M | N | F | D | L | K | Q | G | T | W | G | G | D | W | P | E | A |
| E | E | F | M | [R] | F | [N | P | R | T] | G | [N] | W | [S] | G | [E] | W | P | E | [T] |

| 135 | 136 | 137 | 138 | 139 | 140 | 141 | 142 | 143 | 144 | 145 | 146 | 147 | 148 | 149 | 150 | 151 | 152 | 153 | 154 |
|---|---|---|---|---|---|---|---|---|---|---|---|---|---|---|---|---|---|---|---|
| L | A | I | S | Q | R | W | Q | Q | Q | D | K | A | A | N | K | E | L | T | F |
| [D] | [I] | [V] | [G] | [N] | [L] | W | [M | K] | Q | [P | E] | A | A | [R] | K | E | [S | E] | F |

| 155 | 156 | 157 | 158 | 159 | 160 | 161 | 162 | 163 | 164 | 165 | 166 | 167 | 168 | 169 | 170 | 171 | 172 | 173 | 174 |
|---|---|---|---|---|---|---|---|---|---|---|---|---|---|---|---|---|---|---|---|
| L | L | F | S | C | P | H | R | L | R | E | H | L | E | R | G | R | G | N | L |
| L | L | [T] | S | C | P | [E] | R | L | [L | G] | H | L | E | R | G | R | [Q] | N | L |

| 175 | 176 | 177 | 178 | 179 | 180 | 181 | 182 | 183 | 184 | 185 | 186 | 187 | 188 | 189 | 190 | 191 | 192 | 193 | 194 |
|---|---|---|---|---|---|---|---|---|---|---|---|---|---|---|---|---|---|---|---|
| E | W | K | E | P | P | S | M | R | L | K | A | R | P | S | S | P | G | F | S |
| E | W | K | E | P | P | S | M | R | L | K | A | R | P | [G | N | S] | G | [S] | S |

| 195 | 196 | 197 | 198 | 199 | 200 | 201 | 202 | 203 | 204 | 205 | 206 | 207 | 208 | 209 | 210 | 211 | 212 | 213 | 214 |
|---|---|---|---|---|---|---|---|---|---|---|---|---|---|---|---|---|---|---|---|
| V | L | T | C | S | A | F | S | F | Y | P | P | E | L | Q | L | R | F | L | R |
| V | L | T | C | [A] | A | F | S | F | Y | P | P | E | L | [K | F] | R | F | L | R |

*FIG. 4a*

| 215 | 216 | 217 | 218 | 219 | 220 | 221 | 222 | 223 | 224 | 225 | 226 | 227 | 228 | 229 | 230 | 231 | 232 | 233 | 234 |
|---|---|---|---|---|---|---|---|---|---|---|---|---|---|---|---|---|---|---|---|
| N | G | L | A | A | G | T | G | Q | G | D | F | G | P | N | S | D | G | S | F |
| N | G | L | A | [S] | G | [S] | G | [N | C | S | T] | G | P | N | [G] | D | G | S | F |

| 235 | 236 | 237 | 238 | 239 | 240 | 241 | 242 | 243 | 244 | 245 | 246 | 247 | 248 | 249 | 250 | 251 | 252 | 253 | 254 |
|---|---|---|---|---|---|---|---|---|---|---|---|---|---|---|---|---|---|---|---|
| H | A | S | S | S | L | T | V | K | S | G | D | E | H | H | Y | C | C | I | V |
| H | A | [W] | S | [L] | L | [E] | V | K | [R] | G | D | E | H | H | Y | [Q] | C | [Q] | V |

| 255 | 256 | 257 | 258 | 259 | 260 | 261 | 262 | 263 | 264 | 265 | 266 | 267 |
|---|---|---|---|---|---|---|---|---|---|---|---|---|
| Q | H | A | G | L | A | Q | P | L | R | V | E | L |
| [E] | H | [E] | G | L | A | Q | P | L | [T] | V | [D] | L |

FIG. 4b

| | | | AA Number | 1EXU.pdb | 1 | 2 | 3 | 4 | 5 | 6 | 7 | 8 | 9 | 10 |
|---|---|---|---|---|---|---|---|---|---|---|---|---|---|---|
| SEQ ID NO:9 | Beta-2-microglobulin, Human | Light Chain | 1EXU.pdb Chain B | | I | Q | R | T | P | K | I | Q | V | Y |
| 10 | Beta-2-microglobulin, Rat | Light Chain | 1I1A.pdb Chain B | | I | Q | [K] | T | P | [Q] | I | Q | V | Y |

| 11 | 12 | 13 | 14 | 15 | 16 | 17 | 18 | 19 | 20 | 21 | 22 | 23 | 24 | 25 | 26 | 27 | 28 |
|---|---|---|---|---|---|---|---|---|---|---|---|---|---|---|---|---|---|
| S | R | H | P | A | E | N | G | K | S | N | F | L | N | C | Y | V | S |
| S | R | H | P | [P] | E | N | G | K | [P] | N | F | L | N | C | Y | V | S |

| 29 | 30 | 31 | 32 | 33 | 34 | 35 | 36 | 37 | 38 | 39 | 40 | 41 | 42 | 43 | 44 | 45 | 46 |
|---|---|---|---|---|---|---|---|---|---|---|---|---|---|---|---|---|---|
| G | F | H | P | S | D | I | E | V | D | L | L | K | N | G | E | R | I |
| [Q] | F | H | P | [P | Q] | I | E | [I | E] | L | L | K | N | G | [K | K] | I |

| 47 | 48 | 49 | 50 | 51 | 52 | 53 | 54 | 55 | 56 | 57 | 58 | 59 | 60 | 61 | 62 | 63 | 64 |
|---|---|---|---|---|---|---|---|---|---|---|---|---|---|---|---|---|---|
| E | K | V | E | H | S | D | L | S | F | S | K | D | W | S | F | Y | L |
| [P | N | I] | E | [M] | S | D | L | S | F | S | K | D | W | S | F | Y | [I] |

| 65 | 66 | 67 | 68 | 69 | 70 | 71 | 72 | 73 | 74 | 75 | 76 | 77 | 78 | 79 | 80 | 81 | 82 |
|---|---|---|---|---|---|---|---|---|---|---|---|---|---|---|---|---|---|
| L | Y | Y | T | E | F | T | P | T | E | K | D | E | Y | A | C | R | V |
| L | [A | H] | T | E | F | T | P | T | E | [T] | D | [V] | Y | A | C | R | V |

| 83 | 84 | 85 | 86 | 87 | 88 | 89 | 90 | 91 | 92 | 93 | 94 | 95 | 96 | 97 | 98 | 99 |
|---|---|---|---|---|---|---|---|---|---|---|---|---|---|---|---|---|
| N | H | V | T | L | S | Q | P | K | I | V | K | W | D | R | D | M |
| [K] | H | V | T | L | [K | E] | P | K | [T] | V | [T] | W | D | R | D | M |

FIG. 5

| Human IgG1 WT | Position Substitution | Human IgG1 WT | Position Substitution | Human IgG1 WT | Position Substitution | Human IgG1 WT | Position Substitution |
|---|---|---|---|---|---|---|---|
| K | 246H | R | 255E | V | 279D | V | 284K |
| K | 246S | R | 255F | V | 279F | V | 284P |
| P | 247D | R | 255H | V | 279G | V | 284Q |
| P | 247T | R | 255K | V | 279H | V | 284R |
| K | 248H | R | 255S | V | 279I | V | 284S |
| K | 248P | R | 255V | V | 279K | V | 284Y |
| K | 248Q | T | 256E | V | 279L | H | 285S |
| K | 248R | T | 256H | V | 279M | H | 285V |
| K | 248Y | T | 256V | V | 279N | N | 286# |
| D | 249T | P | 257A | V | 279P | N | 286L |
| D | 249W | P | 257C | V | 279Q | A | 287H |
| L | 251D | P | 257D | V | 279R | A | 287S |
| L | 251E | P | 257E | V | 279S | A | 287V |
| L | 251H | P | 257F | V | 279T | A | 287Y |
| L | 251I | P | 257G | V | 279W | K | 288H |
| L | 251K | P | 257H | V | 279Y | K | 288Q |
| L | 251M | P | 257I | D | 280E | K | 288R |
| L | 251N | P | 257K | D | 280H | K | 288S |
| L | 251T | P | 257L | ^ | ^281A | V | 305H |
| L | 251V | P | 257M | ^ | ^281D | V | 305T |
| L | 251Y | P | 257N | ^ | ^281S | L | 306F |
| M | 252F | P | 257Q | ^ | ^281T | L | 306H |
| M | 252L | P | 257R | V | 282D | L | 306I |
| I | 253L | P | 257S | V | 282F | L | 306N |
| I | 253T | P | 257T | V | 282H | L | 306T |
| I | 253V | P | 257V | V | 282I | L | 306V |
| S | 254H | P | 257W | V | 282T | L | 306Y |
| S | 254L | P | 257Y | E | 283F | T | 307D |
| S | 254N | E | 258R | E | 283I | T | 307V |
| S | 254T | E | 258V | E | 283L | T | 307Y |
| S | 254V | V | 279A | E | 283Y | V | 308A |
| ^ | ^254N | V | 279C | V | 284H | V | 308C |

*FIG. 8a*

| Human IgG1 WT | Position Substitution | Human IgG1 WT | Position Substitution | Human IgG1 WT | Position Substitution | Human IgG1 WT | Position Substitution |
|---|---|---|---|---|---|---|---|
| V | 308D | N | 315E | G | 385N | E | 430H |
| V | 308E | N | 315G | G | 385P | E | 430K |
| V | 308F | N | 315H | G | 385Q | E | 430L |
| V | 308G | N | 315Q | G | 385R | E | 430Q |
| V | 308H | N | 315S | G | 385S | E | 430Y |
| V | 308I | N | 315T | G | 385T | A | 431G |
| V | 308K | K | 317H | G | 385V | A | 431H |
| V | 308L | K | 317S | G | 385W | A | 431I |
| V | 308M | A | 339P | G | 385Y | A | 431P |
| V | 308N | K | 340P | Q | 386E | A | 431S |
| V | 308P | G | 341S | Q | 386H | L | 432F |
| V | 308Q | P | 374H | Q | 386K | L | 432H |
| V | 308R | P | 374S | P | 387# | L | 432N |
| V | 308S | D | 376H | P | 387A | L | 432S |
| V | 308T | D | 376L | P | 387H | L | 432V |
| V | 308W | A | 378H | P | 387K | H | 433E |
| V | 308Y | A | 378N | P | 387Q | H | 433N |
| L | 309F | E | 380T | N | 389E | H | 433P |
| L | 309H | E | 380Y | N | 389H | H | 433R |
| L | 309I | E | 382H | S | 426E | H | 433S |
| L | 309N | S | 383H | S | 426H | N | 434H |
| L | 309P | S | 383K | S | 426L | N | 434Q |
| L | 309Q | S | 383Q | S | 426N | N | 434S |
| L | 309V | N | 384E | S | 426R | N | 434Y |
| L | 309Y | N | 384G | S | 426V | H | 435N |
| H | 310K | N | 384H | S | 426Y | Y | 436E |
| H | 310N | G | 385A | V | 427I | Y | 436F |
| H | 310T | G | 385C | H | 429D | Y | 436H |
| Q | 311H | G | 385D | H | 429F | Y | 436L |
| Q | 311L | G | 385E | H | 429K | Y | 436Q |
| Q | 311S | G | 385F | H | 429N | Y | 436V |
| Q | 311T | G | 385H | H | 429Q | Y | 436W |
| Q | 311V | G | 385I | H | 429S | T | 437E |
| Q | 311W | G | 385K | H | 429T | T | 437V |
| D | 312H | G | 385L | H | 429Y | Q | 438E |
| W | 313Y | G | 385M | E | 430D | Q | 438H |
|   |   |   |   |   |   | Q | 438K |

*FIG. 8b*

| Human IgG1 WT | Position Substitution | Human IgG1 WT | Position Substitution | Human IgG1 WT | Position Substitution | Human IgG1 WT | Position Substitution |
|---|---|---|---|---|---|---|---|
| K | 246H | R | 255S | V | 279N | A | 287S |
| K | 246S | R | 255V | V | 279P | A | 287V |
| P | 247D | T | 256H | V | 279Q | A | 287Y |
| P | 247T | T | 256V | V | 279R | K | 288H |
| K | 248H | P | 257A | V | 279S | K | 288Q |
| K | 248P | P | 257C | V | 279T | K | 288S |
| K | 248Q | P | 257D | V | 279W | V | 305H |
| K | 248R | P | 257E | V | 279Y | V | 305T |
| K | 248Y | P | 257F | D | 280H | L | 306F |
| D | 249T | P | 257G | ^ | ^281A | L | 306H |
| D | 249W | P | 257H | ^ | ^281D | L | 306I |
| L | 251D | P | 257I | ^ | ^281S | L | 306N |
| L | 251E | P | 257K | ^ | ^281T | L | 306T |
| L | 251H | P | 257L | V | 282D | L | 306V |
| L | 251I | P | 257M | V | 282F | L | 306Y |
| L | 251K | P | 257N | V | 282H | T | 307D |
| L | 251M | P | 257Q | V | 282I | T | 307V |
| L | 251N | P | 257R | V | 282T | T | 307Y |
| L | 251T | P | 257S | E | 283F | V | 308C |
| L | 251V | P | 257T | E | 283I | V | 308E |
| L | 251Y | P | 257V | E | 283L | V | 308F |
| M | 252L | P | 257W | E | 283Y | V | 308G |
| I | 253L | P | 257Y | V | 284H | V | 308H |
| I | 253T | E | 258R | V | 284K | V | 308I |
| I | 253V | E | 258V | V | 284P | V | 308K |
| S | 254H | V | 279A | V | 284Q | V | 308L |
| S | 254L | V | 279C | V | 284R | V | 308M |
| S | 254N | V | 279D | V | 284S | V | 308N |
| S | 254V | V | 279F | V | 284Y | V | 308P |
| ^ | ^254N | V | 279G | H | 285S | V | 308Q |
| R | 255E | V | 279H | H | 285V | V | 308R |
| R | 255F | V | 279I | N | 286# | V | 308S |
| R | 255H | V | 279K | N | 286L | V | 308W |
| R | 255K | V | 279M | A | 287H | V | 308Y |

*FIG. 9a*

| Human IgG1 WT | Position Substitution | Human IgG1 WT | Position Substitution | Human IgG1 WT | Position Substitution | Human IgG1 WT | Position Substitution |
|---|---|---|---|---|---|---|---|
| L | 309F | E | 382H | S | 426H | H | 433S |
| L | 309H | S | 383H | S | 426L | N | 434H |
| L | 309N | S | 383K | S | 426N | N | 434Q |
| L | 309Q | S | 383Q | S | 426R | N | 434S |
| L | 309V | N | 384E | S | 426V | H | 435N |
| L | 309Y | N | 384G | S | 426Y | Y | 436E |
| H | 310K | N | 384H | V | 427I | Y | 436F |
| H | 310N | G | 385A | H | 429D | Y | 436L |
| H | 310T | G | 385C | H | 429F | Y | 436V |
| Q | 311L | G | 385F | H | 429K | Y | 436W |
| Q | 311T | G | 385H | H | 429N | T | 437E |
| Q | 311V | G | 385I | H | 429Q | T | 437V |
| Q | 311W | G | 385K | H | 429S | Q | 438H |
| D | 312H | G | 385L | H | 429T | Q | 438K |
| W | 313Y | G | 385M | H | 429Y | | |
| N | 315E | G | 385N | E | 430D | | |
| N | 315G | G | 385P | E | 430H | | |
| N | 315H | G | 385Q | E | 430K | | |
| N | 315Q | G | 385S | E | 430L | | |
| N | 315S | G | 385T | E | 430Q | | |
| N | 315T | G | 385V | E | 430Y | | |
| K | 317H | G | 385W | A | 431G | | |
| K | 317S | G | 385Y | A | 431H | | |
| A | 339P | Q | 386E | A | 431I | | |
| K | 340P | Q | 386H | A | 431P | | |
| G | 341S | Q | 386K | A | 431S | | |
| P | 374H | P | 387# | L | 432F | | |
| P | 374S | P | 387A | L | 432H | | |
| D | 376H | P | 387H | L | 432N | | |
| D | 376L | P | 387K | L | 432S | | |
| A | 378H | P | 387Q | L | 432V | | |
| A | 378N | N | 389E | H | 433E | | |
| E | 380T | N | 389H | H | 433N | | |
| E | 380Y | S | 426E | H | 433P | | |

*FIG. 9b*

| Human IgG1 WT | Position Substitution | Human IgG1 WT | Position Substitution | Human IgG1 WT | Position Substitution | Human IgG1 WT | Position Substitution |
|---|---|---|---|---|---|---|---|
| K | 246H | P | 257I | N | 286L | W | 313Y |
| K | 246S | P | 257L | A | 287V | N | 315G |
| P | 247D | P | 257M | K | 288Q | N | 315Q |
| P | 247T | P | 257N | K | 288S | N | 315S |
| K | 248P | P | 257Q | V | 305T | N | 315T |
| K | 248Q | P | 257S | L | 306F | A | 339P |
| K | 248Y | P | 257T | L | 306H | K | 340P |
| D | 249T | P | 257V | L | 306I | G | 341S |
| D | 249W | P | 257W | L | 306N | P | 374H |
| L | 251D | P | 257Y | L | 306T | P | 374S |
| L | 251E | E | 258V | L | 306V | D | 376L |
| L | 251H | V | 279A | L | 306Y | A | 378H |
| L | 251I | V | 279C | T | 307V | A | 378N |
| L | 251T | V | 279F | V | 308C | E | 380T |
| L | 251V | V | 279I | V | 308F | E | 380Y |
| M | 252L | V | 279P | V | 308G | E | 382H |
| I | 253L | V | 279S | V | 308L | S | 383Q |
| I | 253T | V | 279T | V | 308M | N | 384E |
| I | 253V | V | 279W | V | 308N | N | 384G |
| S | 254H | V | 279Y | V | 308P | N | 384H |
| S | 254L | ^ | ^281A | V | 308Q | G | 385A |
| S | 254N | ^ | ^281D | V | 308S | G | 385C |
| S | 254V | ^ | ^281S | V | 308W | G | 385F |
| ^ | ^254N | ^ | ^281T | V | 308Y | G | 385I |
| R | 255E | V | 282F | L | 309F | G | 385L |
| R | 255H | V | 282I | L | 309N | G | 385M |
| R | 255K | V | 282T | L | 309Q | G | 385N |
| R | 255V | E | 283F | L | 309V | G | 385P |
| T | 256H | E | 283I | L | 309Y | G | 385Q |
| T | 256V | E | 283L | H | 310T | G | 385S |
| P | 257A | E | 283Y | Q | 311L | G | 385T |
| P | 257C | V | 284P | Q | 311T | G | 385V |
| P | 257F | H | 285V | Q | 311V | G | 385W |
| P | 257G | N | 286# | Q | 311W | G | 385Y |

FIG. 10a

| Human IgG1 WT | Position Substitution | Human IgG1 WT | Position Substitution |
|---|---|---|---|
| Q | 386E | N | 434H |
| Q | 386H | N | 434Q |
| Q | 386K | N | 434S |
| P | 387# | H | 435N |
| P | 387A | Y | 436F |
| P | 387H | Y | 436L |
| P | 387K | Y | 436V |
| P | 387Q | Y | 436W |
| N | 389H | T | 437E |
| S | 426L | T | 437V |
| S | 426N | | |
| S | 426V | | |
| S | 426Y | | |
| V | 427I | | |
| H | 429D | | |
| H | 429F | | |
| H | 429K | | |
| H | 429N | | |
| H | 429Q | | |
| H | 429S | | |
| H | 429T | | |
| H | 429Y | | |
| E | 430L | | |
| A | 431G | | |
| A | 431I | | |
| A | 431P | | |
| A | 431S | | |
| L | 432F | | |
| L | 432H | | |
| L | 432V | | |
| H | 433E | | |
| H | 433N | | |
| H | 433P | | |
| H | 433S | | |

FIG. 10b

| Variant | Variable - Fc region | Background Mutations | Median Fold Increase | N |
|---|---|---|---|---|
| WT | Herceptin-IgG1 | | 1.00 | 19 |
| WT | Herceptin-IgG2 | | 0.45 | 2 |
| K246H | Herceptin-IgG1 | | 0.65 | 1 |
| K246S | Herceptin-IgG1 | | 0.55 | 1 |
| P247D | Herceptin-IgG1 | | 1.45 | 1 |
| P247T | Herceptin-IgG1 | | 0.23 | 1 |
| K248H | Herceptin-IgG1 | | 0.62 | 2 |
| K248P | Herceptin-IgG1 | | | 0 |
| K248Q | Herceptin-IgG1 | | 1.00 | 1 |
| K248R | Herceptin-IgG1 | | 0.44 | 1 |
| K248Y | Herceptin-IgG1 | | 2.09 | 3 |
| D249T | Herceptin-IgG1 | | | 0 |
| D249W | Herceptin-IgG1 | | 0.56 | 1 |
| T250Q | Herceptin-IgG1 | | | 0 |
| T250Q/M428L | Herceptin-IgG1 | | 2.06 | 13 |
| L251D | Herceptin-IgG1 | | 0.28 | 2 |
| L251E | Herceptin-IgG1 | | 0.07 | 1 |
| L251H | Herceptin-IgG1 | | 0.57 | 1 |
| L251I | Herceptin-IgG1 | | 0.28 | 1 |
| L251K | Herceptin-IgG1 | | 0.10 | 1 |
| L251M | Herceptin-IgG1 | | 0.26 | 1 |
| L251N | Herceptin-IgG1 | | 0.10 | 1 |
| L251T | Herceptin-IgG1 | | 1.12 | 1 |
| L251V | Herceptin-IgG1 | | 0.29 | 1 |
| L251Y | Herceptin-IgG1 | | 0.55 | 1 |
| M252F | Herceptin-IgG1 | | 0.70 | 1 |
| M252L | Herceptin-IgG1 | | 0.10 | 1 |
| M252W | Herceptin-IgG1 | | 7.55 | 7 |
| M252Y | Herceptin-IgG1 | | | 0 |
| M252Y/S254T/T256E | Herceptin-IgG1 | | | 0 |
| M252Y/P257L | Herceptin-IgG1 | | 1.22 | 1 |
| M252Y/P257N | Herceptin-IgG1 | | 25.48 | 3 |
| M252Y/V279Q | Herceptin-IgG1 | | 5.62 | 3 |
| M252Y/V308F | Herceptin-IgG1 | | 1.44 | 2 |
| I253L | Herceptin-IgG1 | | 0.32 | 1 |
| I253T | Herceptin-IgG1 | | | 0 |
| I253V | Herceptin-IgG1 | | 0.28 | 1 |
| S254H | Herceptin-IgG1 | | 1.34 | 2 |
| S254L | Herceptin-IgG1 | | 0.61 | 1 |
| S254N | Herceptin-IgG1 | | 0.15 | 1 |
| S254T | Herceptin-IgG1 | | 0.61 | 1 |
| S254V | Herceptin-IgG1 | | 0.62 | 1 |
| ^254N | Herceptin-IgG1 | | 0.01 | 1 |

*FIG. 13a*

| Variant | Variable - Fc region | Background Mutations | Median Fold Increase | N |
|---|---|---|---|---|
| R255E | Herceptin-IgG1 | | | 0 |
| R255F | Herceptin-IgG1 | | | 0 |
| R255H | Herceptin-IgG1 | | 0.69 | 2 |
| R255K | Herceptin-IgG1 | | 0.22 | 1 |
| R255S | Herceptin-IgG1 | | | 0 |
| R255V | Herceptin-IgG1 | | 0.46 | 1 |
| T256E | Herceptin-IgG1 | | | 0 |
| T256H | Herceptin-IgG1 | | 0.06 | 1 |
| T256V | Herceptin-IgG1 | | 0.29 | 1 |
| P257A | Herceptin-IgG1 | | 1.88 | 1 |
| P257C | Herceptin-IgG1 | | 15.69 | 1 |
| P257D | Herceptin-IgG1 | | 0.08 | 1 |
| P257E | Herceptin-IgG1 | | 0.13 | 1 |
| P257F | Herceptin-IgG1 | | 0.05 | 1 |
| P257G | Herceptin-IgG1 | | 0.76 | 1 |
| P257H | Herceptin-IgG1 | | 0.49 | 1 |
| P257I | Herceptin-IgG1 | | 1.80 | 2 |
| P257K | Herceptin-IgG1 | | 0.07 | 1 |
| P257L | Herceptin-IgG1 | | 2.63 | 6 |
| P257L | Herceptin-IgG1 | I332E | 5.04 | 1 |
| P257L | Herceptin-IgG1 | S239D/I332E | 3.96 | 2 |
| P257L/^281S | Herceptin-IgG1 | | 11.26 | 3 |
| P257L/G385H | Herceptin-IgG1 | | 0.41 | 2 |
| P257L/V279E | Herceptin-IgG1 | | 3.01 | 3 |
| P257L/V279Q | Herceptin-IgG1 | | 12.40 | 3 |
| P257L/V279Q/V284E | Herceptin-IgG1 | | | 0 |
| P257L/V279Y | Herceptin-IgG1 | | 0.75 | 1 |
| P257L/V284E | Herceptin-IgG1 | | 0.65 | 1 |
| P257L/V308F | Herceptin-IgG1 | | 6.68 | 4 |
| P257L/V308Y | Herceptin-IgG1 | | 3.50 | 3 |
| P257L/Q311V | Herceptin-IgG1 | | 23.30 | 3 |
| P257L/G385N | Herceptin-IgG1 | | 3.03 | 2 |
| P257L/M428L | Herceptin-IgG1 | | 3.73 | 1 |
| P257L/N434Y | Herceptin-IgG1 | | 835.00 | 3 |
| P257M | Herceptin-IgG1 | | 8.32 | 1 |
| P257N | Herceptin-IgG1 | | 2.56 | 8 |
| P257N/V279E | Herceptin-IgG1 | | 6.00 | 3 |
| P257N/V279Q | Herceptin-IgG1 | | 4.05 | 1 |
| P257N/V279Q/V284E | Herceptin-IgG1 | | | 0 |
| P257N/V279Y | Herceptin-IgG1 | | 6.22 | 3 |
| P257N/^281S | Herceptin-IgG1 | | 5.99 | 3 |
| P257N/V284E | Herceptin-IgG1 | | 5.92 | 2 |
| P257N/V284E/V308F | Herceptin-IgG1 | | | 0 |
| P257N/G385H | Herceptin-IgG1 | | 0.84 | 2 |
| P257N/L306Y | Herceptin-IgG1 | | 1.29 | 2 |
| P257N/V308F | Herceptin-IgG1 | | 0.88 | 4 |
| P257N/V308Y | Herceptin-IgG1 | | 48.20 | 1 |
| P257Q | Herceptin-IgG1 | | 0.25 | 2 |
| P257Q/V279Q | Herceptin-IgG1 | | 0.71 | 2 |
| P257Q/V284E | Herceptin-IgG1 | | | 0 |

FIG. 13b

| Variant | Variable - Fc region | Background Mutations | Median Fold Increase | N |
|---|---|---|---|---|
| P257R | Herceptin-IgG1 | | 0.29 | 1 |
| P257S | Herceptin-IgG1 | | 1.94 | 2 |
| P257T | Herceptin-IgG1 | | 1.85 | 1 |
| P257V | Herceptin-IgG1 | | 1.90 | 1 |
| P257W | Herceptin-IgG1 | | 0.24 | 1 |
| P257Y | Herceptin-IgG1 | | 3.40 | 2 |
| P257Y/V279Q | Herceptin-IgG1 | | 1.78 | 2 |
| P257Y/^281S | Herceptin-IgG1 | | | 0 |
| P257Y/V308F | Herceptin-IgG1 | | | 0 |
| E258R | Herceptin-IgG1 | | 0.19 | 1 |
| E258V | Herceptin-IgG1 | | 0.22 | 1 |
| V279A | Herceptin-IgG1 | | 5.20 | 1 |
| V279C | Herceptin-IgG1 | | 3.93 | 1 |
| V279D | Herceptin-IgG1 | | 0.93 | 2 |
| V279E | Herceptin-IgG1 | | 0.47 | 5 |
| V279E/G385H | Herceptin-IgG1 | | 0.61 | 3 |
| V279E/V284E | Herceptin-IgG1 | | 3.91 | 2 |
| V279F | Herceptin-IgG1 | | | 0 |
| V279G | Herceptin-IgG1 | | 1.27 | 1 |
| V279H | Herceptin-IgG1 | | | 0 |
| V279I | Herceptin-IgG1 | | 15.12 | 1 |
| V279K | Herceptin-IgG1 | | | 0 |
| V279L | Herceptin-IgG1 | | 0.30 | 1 |
| V279M | Herceptin-IgG1 | | 2.89 | 1 |
| V279N | Herceptin-IgG1 | | | 0 |
| V279P | Herceptin-IgG1 | | 0.31 | 1 |
| V279Q | Herceptin-IgG1 | | 0.50 | 9 |
| V279Q/V284E | Herceptin-IgG1 | | 0.86 | 2 |
| V279Q/L306Y | Herceptin-IgG1 | | 3.93 | 3 |
| V279Q/V308F | Herceptin-IgG1 | | 4.60 | 3 |
| V279Q/Q311V | Herceptin-IgG1 | | | 0 |
| V279Q/G385H | Herceptin-IgG1 | | 1.08 | 4 |
| V279R | Herceptin-IgG1 | | 1.11 | 1 |
| V279S | Herceptin-IgG1 | | 0.96 | 1 |
| V279T | Herceptin-IgG1 | | 0.75 | 3 |
| V279W | Herceptin-IgG1 | | 0.44 | 1 |
| V279Y | Herceptin-IgG1 | | 0.67 | 5 |

*FIG. 13c*

| Variant | Variable - Fc region | Background Mutations | Median Fold Increase | N |
|---|---|---|---|---|
| V279Y/G385H | Herceptin-IgG1 | | 0.58 | 3 |
| V279Y/V284E | Herceptin-IgG1 | | | 0 |
| V279Y/V308F | Herceptin-IgG1 | | 1.59 | 4 |
| D280E | Herceptin-IgG1 | | 0.28 | 1 |
| D280H | Herceptin-IgG1 | | 0.53 | 2 |
| ^281A | Herceptin-IgG1 | | | 0 |
| ^281D | Herceptin-IgG1 | | 0.89 | 3 |
| ^281S | Herceptin-IgG1 | | 0.62 | 7 |
| ^281S/V284E | Herceptin-IgG1 | | | 0 |
| ^281S/V308F | Herceptin-IgG1 | | 2.13 | 2 |
| ^281S/V308Y | Herceptin-IgG1 | | 1.46 | 1 |
| ^281S/N434Y | Herceptin-IgG1 | | 176.70 | 3 |
| ^281T | Herceptin-IgG1 | | 0.56 | 1 |
| V282D | Herceptin-IgG1 | | 0.25 | 1 |
| V282F | Herceptin-IgG1 | | 0.42 | 1 |
| V282H | Herceptin-IgG1 | | 0.31 | 1 |
| V282I | Herceptin-IgG1 | | 0.36 | 1 |
| V282T | Herceptin-IgG1 | | 0.58 | 1 |
| E283F | Herceptin-IgG1 | | 0.79 | 3 |
| E283F/V284E | Herceptin-IgG1 | | 1.93 | 1 |
| E283I | Herceptin-IgG1 | | 1.15 | 2 |
| E283L | Herceptin-IgG1 | | 1.85 | 5 |
| E283L/V284E | Herceptin-IgG1 | | | 0 |
| E283Y | Herceptin-IgG1 | | | 0 |
| V284D | Herceptin-IgG1 | | | 0 |
| V284E | Herceptin-IgG1 | | 0.68 | 10 |
| V284E/G385H | Herceptin-IgG1 | | 1.13 | 3 |
| V284E/L306Y | Herceptin-IgG1 | | 0.66 | 3 |
| V284E/V308F | Herceptin-IgG1 | | 3.96 | 3 |
| V284E/V308Y | Herceptin-IgG1 | | 0.22 | 1 |
| V284H | Herceptin-IgG1 | | | 0 |
| V284K | Herceptin-IgG1 | | 0.15 | 1 |
| V284P | Herceptin-IgG1 | | | 0 |
| V284Q | Herceptin-IgG1 | | 1.60 | 2 |
| V284R | Herceptin-IgG1 | | | 0 |
| V284S | Herceptin-IgG1 | | 0.48 | 2 |
| V284Y | Herceptin-IgG1 | | 0.55 | 1 |
| H285F | Herceptin-IgG1 | | 0.98 | 1 |
| H285S | Herceptin-IgG1 | | 0.89 | 2 |
| H285V | Herceptin-IgG1 | | 0.74 | 2 |
| deleteN286 | Herceptin-IgG1 | | 1.95 | 1 |
| N286D | Herceptin-IgG1 | | 10.18 | 1 |
| N286L | Herceptin-IgG1 | | 1.45 | 1 |

*FIG. 13d*

| Variant | Variable - Fc region | Background Mutations | Median Fold Increase | N |
|---|---|---|---|---|
| A287H | Herceptin-IgG1 | | 0.81 | 1 |
| A287S | Herceptin-IgG1 | | 1.27 | 2 |
| A287V | Herceptin-IgG1 | | 0.74 | 1 |
| A287Y | Herceptin-IgG1 | | 0.52 | 1 |
| K288D | Herceptin-IgG1 | | | 0 |
| K288H | Herceptin-IgG1 | | 0.53 | 2 |
| K288Q | Herceptin-IgG1 | | 0.33 | 1 |
| K288R | Herceptin-IgG1 | | 0.27 | 3 |
| K288S | Herceptin-IgG1 | | 0.03 | 1 |
| V305H | Herceptin-IgG1 | | 0.51 | 1 |
| V305T | Herceptin-IgG1 | | 0.55 | 1 |
| L306E | Herceptin-IgG1 | | | 0 |
| L306F | Herceptin-IgG1 | | 0.46 | 1 |
| L306H | Herceptin-IgG1 | | | 0 |
| L306I | Herceptin-IgG1 | | 0.70 | 2 |
| L306N | Herceptin-IgG1 | | 0.91 | 1 |
| L306T | Herceptin-IgG1 | | 0.64 | 2 |
| L306V | Herceptin-IgG1 | | 0.34 | 1 |
| L306Y | Herceptin-IgG1 | | 1.18 | 6 |
| T307D | Herceptin-IgG1 | | 0.82 | 1 |
| T307V | Herceptin-IgG1 | | 0.57 | 3 |
| T307Y | Herceptin-IgG1 | | | 0 |
| V308A | Herceptin-IgG1 | | 1.38 | 1 |
| V308C | Herceptin-IgG1 | | 2.84 | 1 |
| V308D | Herceptin-IgG1 | | 0.02 | 1 |
| V308E | Herceptin-IgG1 | | | 0 |
| V308F | Herceptin-IgG1 | | 2.87 | 14 |
| V308F | Herceptin-IgG1 | S298A/E333A/K334A | 36.04 | 1 |
| V308F | Herceptin-IgG1 | I332E | 1.82 | 3 |
| V308F | Herceptin-IgG1 | S239D/I332E | 1.91 | 3 |
| V308F/Q311V | Herceptin-IgG1 | | 11.73 | 1 |
| V308F/G385H | Herceptin-IgG1 | | 1.62 | 3 |
| V308F/G385N | Herceptin-IgG1 | | | 0 |
| V308F/M428L | Herceptin-IgG1 | | 11.79 | 1 |
| V308F/N434Y | Herceptin-IgG1 | | 353.73 | 3 |

*FIG. 13e*

| Variant | Variable - Fc region | Background Mutations | Median Fold Increase | N |
|---|---|---|---|---|
| V308G | Herceptin-IgG1 | | 0.18 | 1 |
| V308H | Herceptin-IgG1 | | | 0 |
| V308I | Herceptin-IgG1 | | 0.48 | 1 |
| V308K | Herceptin-IgG1 | | 0.53 | 1 |
| V308L | Herceptin-IgG1 | | 0.48 | 1 |
| V308M | Herceptin-IgG1 | | 0.45 | 1 |
| V308N | Herceptin-IgG1 | | 1.22 | 3 |
| V308P | Herceptin-IgG1 | | | 0 |
| V308Q | Herceptin-IgG1 | | 0.58 | 1 |
| V308R | Herceptin-IgG1 | | 1.56 | 1 |
| V308S | Herceptin-IgG1 | | 0.15 | 1 |
| V308T | Herceptin-IgG1 | | 0.45 | 2 |
| V308W | Herceptin-IgG1 | | 9.57 | 1 |
| V308Y | Herceptin-IgG1 | | 4.25 | 4 |
| V308Y/G385H | Herceptin-IgG1 | | | 0 |
| L309F | Herceptin-IgG1 | | 0.36 | 1 |
| L309H | Herceptin-IgG1 | | | 0 |
| L309I | Herceptin-IgG1 | | 0.34 | 2 |
| L309N | Herceptin-IgG1 | | | 0 |
| L309P | Herceptin-IgG1 | | | 0 |
| L309Q | Herceptin-IgG1 | | 0.15 | 1 |
| L309V | Herceptin-IgG1 | | 0.59 | 3 |
| L309Y | Herceptin-IgG1 | | 0.20 | 1 |
| H310K | Herceptin-IgG1 | | 0.62 | 2 |
| H310N | Herceptin-IgG1 | | 0.39 | 1 |
| H310T | Herceptin-IgG1 | | 0.39 | 2 |
| Q311A | Herceptin-IgG1 | | 2.52 | 1 |
| Q311H | Herceptin-IgG1 | | 0.87 | 1 |
| Q311L | Herceptin-IgG1 | | 2.34 | 1 |
| Q311S | Herceptin-IgG1 | | | 0 |
| Q311T | Herceptin-IgG1 | | 1.47 | 1 |
| Q311V | Herceptin-IgG1 | | 3.15 | 3 |
| Q311W | Herceptin-IgG1 | | 0.89 | 1 |
| D312H | Herceptin-IgG1 | | 0.38 | 1 |
| W313Y | Herceptin-IgG1 | | 0.48 | 1 |
| N315E | Herceptin-IgG1 | | 0.53 | 1 |
| N315G | Herceptin-IgG1 | | | 0 |
| N315H | Herceptin-IgG1 | | 0.45 | 1 |
| N315Q | Herceptin-IgG1 | | 0.79 | 3 |
| N315R | Herceptin-IgG1 | | 0.48 | 1 |
| N315S | Herceptin-IgG1 | | 0.31 | 1 |
| N315T | Herceptin-IgG1 | | 1.72 | 1 |
| K317H | Herceptin-IgG1 | | 0.71 | 1 |
| K317S | Herceptin-IgG1 | | | 0 |
| A339P | Herceptin-IgG1 | | | 0 |

*FIG. 13f*

| Variant | Variable - Fc region | Background Mutations | Median Fold Increase | N |
|---|---|---|---|---|
| K340P | Herceptin-IgG1 | | 0.54 | 1 |
| G341S | Herceptin-IgG1 | | 0.77 | 1 |
| P374H | Herceptin-IgG1 | | | 0 |
| P374S | Herceptin-IgG1 | | 0.59 | 1 |
| D376H | Herceptin-IgG1 | | 0.42 | 1 |
| D376L | Herceptin-IgG1 | | 0.49 | 1 |
| A378H | Herceptin-IgG1 | | 0.50 | 1 |
| A378N | Herceptin-IgG1 | | 0.58 | 1 |
| E380T | Herceptin-IgG1 | | | 0 |
| E380Y | Herceptin-IgG1 | | 0.35 | 1 |
| E382H | Herceptin-IgG1 | | 0.43 | 3 |
| S383H | Herceptin-IgG1 | | 0.96 | 1 |
| S383K | Herceptin-IgG1 | | | 0 |
| S383Q | Herceptin-IgG1 | | 0.90 | 1 |
| N384E | Herceptin-IgG1 | | 0.57 | 1 |
| N384G | Herceptin-IgG1 | | 0.38 | 1 |
| N384H | Herceptin-IgG1 | | 0.57 | 1 |
| G385A | Herceptin-IgG1 | | 0.27 | 1 |
| G385C | Herceptin-IgG1 | | 0.36 | 1 |
| G385D | Herceptin-IgG1 | | 0.54 | 1 |
| G385E | Herceptin-IgG1 | | 6.12 | 1 |
| G385F | Herceptin-IgG1 | | | 0 |
| G385H | Herceptin-IgG1 | | 1.05 | 5 |
| G385H | Herceptin-IgG1 | I332E | 1.37 | 3 |
| G385H | Herceptin-IgG1 | S239D/I332E | 17.37 | 2 |
| G385I | Herceptin-IgG1 | | | 0 |
| G385K | Herceptin-IgG1 | | 0.38 | 1 |
| G385L | Herceptin-IgG1 | | | 0 |
| G385M | Herceptin-IgG1 | | | 0 |
| G385N | Herceptin-IgG1 | | 2.94 | 2 |
| G385P | Herceptin-IgG1 | | | 0 |
| G385Q | Herceptin-IgG1 | | | 0 |
| G385R | Herceptin-IgG1 | | 0.11 | 1 |
| G385S | Herceptin-IgG1 | | 0.18 | 1 |
| G385T | Herceptin-IgG1 | | 0.16 | 1 |
| G385V | Herceptin-IgG1 | | 0.13 | 1 |
| G385W | Herceptin-IgG1 | | 0.08 | 1 |
| G385Y | Herceptin-IgG1 | | | 0 |
| Q386E | Herceptin-IgG1 | | 0.85 | 1 |
| Q386H | Herceptin-IgG1 | | 0.68 | 1 |
| Q386K | Herceptin-IgG1 | | 0.06 | 1 |

FIG. 13g

| Variant | Variable - Fc region | Background Mutations | Median Fold Increase | N |
|---|---|---|---|---|
| deleteP387 | Herceptin-IgG1 | | | 0 |
| P387A | Herceptin-IgG1 | | 0.26 | 1 |
| P387H | Herceptin-IgG1 | | 1.04 | 1 |
| P387K | Herceptin-IgG1 | | 0.86 | 1 |
| P387Q | Herceptin-IgG1 | | 1.06 | 1 |
| N389E | Herceptin-IgG1 | | 0.78 | 1 |
| N389H | Herceptin-IgG1 | | 0.53 | 1 |
| S426E | Herceptin-IgG1 | | 0.60 | 1 |
| S426H | Herceptin-IgG1 | | 1.14 | 1 |
| S426L | Herceptin-IgG1 | | 1.30 | 1 |
| S426N | Herceptin-IgG1 | | 0.25 | 1 |
| S426R | Herceptin-IgG1 | | 1.47 | 1 |
| S426V | Herceptin-IgG1 | | 1.38 | 1 |
| S426Y | Herceptin-IgG1 | | 0.53 | 1 |
| V427A | Herceptin-IgG1 | | 0.81 | 1 |
| V427I | Herceptin-IgG1 | | 0.64 | 1 |
| M428L | Herceptin-IgG1 | | 2.92 | 5 |
| H429D | Herceptin-IgG1 | | 0.47 | 2 |
| H429F | Herceptin-IgG1 | | 0.13 | 1 |
| H429K | Herceptin-IgG1 | | | 0 |
| H429N | Herceptin-IgG1 | | 0.50 | 2 |
| H429Q | Herceptin-IgG1 | | 1.40 | 1 |
| H429S | Herceptin-IgG1 | | 0.53 | 3 |
| H429T | Herceptin-IgG1 | | 0.66 | 3 |
| H429Y | Herceptin-IgG1 | | 0.13 | 1 |
| E430D | Herceptin-IgG1 | | 0.20 | 1 |
| E430H | Herceptin-IgG1 | | 0.35 | 1 |
| E430K | Herceptin-IgG1 | | | 0 |
| E430L | Herceptin-IgG1 | | 0.50 | 1 |
| E430Q | Herceptin-IgG1 | | 0.26 | 1 |
| E430Y | Herceptin-IgG1 | | | 0 |
| A431G | Herceptin-IgG1 | | 0.05 | 1 |
| A431H | Herceptin-IgG1 | | 0.45 | 3 |
| A431I | Herceptin-IgG1 | | 0.55 | 1 |
| A431P | Herceptin-IgG1 | | | 0 |
| A431S | Herceptin-IgG1 | | 0.51 | 1 |
| L432F | Herceptin-IgG1 | | 0.39 | 1 |
| L432H | Herceptin-IgG1 | | | 0 |
| L432N | Herceptin-IgG1 | | 0.45 | 1 |
| L432S | Herceptin-IgG1 | | 0.57 | 1 |
| L432V | Herceptin-IgG1 | | 0.73 | 3 |
| H433E | Herceptin-IgG1 | | | 0 |
| H433N | Herceptin-IgG1 | | 0.19 | 1 |
| H433P | Herceptin-IgG1 | | 1.18 | 1 |
| H433R | Herceptin-IgG1 | | 0.88 | 1 |
| H433S | Herceptin-IgG1 | | | 0 |

*FIG. 13h*

| Variant | Variable - Fc region | Background Mutations | Median Fold Increase | N |
|---|---|---|---|---|
| N434A | Herceptin-IgG1 | | 3.23 | 6 |
| N434H | Herceptin-IgG1 | | 3.91 | 1 |
| N434L | Herceptin-IgG1 | | 0.16 | 1 |
| N434Q | Herceptin-IgG1 | | 0.15 | 1 |
| N434S | Herceptin-IgG1 | | 0.29 | 1 |
| N434Y | Herceptin-IgG1 | | 16.25 | 3 |
| H435N | Herceptin-IgG1 | | 0.19 | 1 |
| Y436E | Herceptin-IgG1 | | 0.39 | 1 |
| Y436F | Herceptin-IgG1 | | 0.39 | 2 |
| Y436H | Herceptin-IgG1 | | 0.48 | 1 |
| Y436L | Herceptin-IgG1 | | 0.28 | 1 |
| Y436Q | Herceptin-IgG1 | | 0.24 | 1 |
| Y436V | Herceptin-IgG1 | | 0.51 | 1 |
| Y436W | Herceptin-IgG1 | | 0.30 | 1 |
| T437E | Herceptin-IgG1 | | | 0 |
| T437V | Herceptin-IgG1 | | 0.16 | 1 |
| Q438E | Herceptin-IgG1 | | 0.28 | 1 |
| Q438H | Herceptin-IgG1 | | 0.24 | 1 |
| Q438K | Herceptin-IgG1 | | 0.24 | 1 |

*FIG. 13i*

| Variant | Variable - Fc region | Background Mutations | Median Fold Increase | N |
|---|---|---|---|---|
| WT | Herceptin - IgG1/2 Hybrid Fc v1 | | 1.45 | 6 |
| WT | Herceptin - IgG1/2 Hybrid Fc | | | 0 |
| P257L | Herceptin - IgG1/2 Hybrid Fc | | | 0 |
| V308F | Herceptin - IgG1/2 Hybrid Fc | | | 0 |
| G385H | Herceptin - IgG1/2 Hybrid Fc | | | 0 |
| WT | Herceptin - IgG1/2 Hybrid Fc | S239D/I332E | | 0 |
| P257L | Herceptin - IgG1/2 Hybrid Fc | S239D/I332E | | 0 |
| V308F | Herceptin - IgG1/2 Hybrid Fc | S239D/I332E | | 0 |
| G385H | Herceptin - IgG1/2 Hybrid Fc | S239D/I332E | | 0 |
| P257L | AC10 - IgG1 | | | 0 |
| V308F | AC10 - IgG1 | | | 0 |
| G385H | AC10 - IgG1 | | | 0 |
| P257L | AC10 - IgG1 | S239D/I332E | | 0 |
| V308F | AC10 - IgG1 | S239D/I332E | | 0 |
| G385H | AC10 - IgG1 | S239D/I332E | | 0 |
| P257L | AC10 - IgG1/2 Hybrid Fc | | | 0 |
| V308F | AC10 - IgG1/2 Hybrid Fc | | | 0 |
| G385H | AC10 - IgG1/2 Hybrid Fc | | | 0 |
| P257L | AC10 - IgG1/2 Hybrid Fc | S239D/I332E | | 0 |
| V308F | AC10 - IgG1/2 Hybrid Fc | S239D/I332E | | 0 |
| G385H | AC10 - IgG1/2 Hybrid Fc | S239D/I332E | | 0 |
| T250Q | AC10 - IgG1 | S239D/I332E | 0.59 | 1 |
| V284D | AC10 - IgG1 | S239D/I332E | 0.88 | 1 |
| V284E | AC10 - IgG1 | S239D/I332E | 0.17 | 1 |
| M428L | AC10 - IgG1 | S239D/I332E | 1.82 | 1 |

*FIG. 13j*

| Mutations | FcRn Binding ratio Variant / WT |
|---|---|
| D221K | 5.66 |
| D221Y | 2.74 |
| K222Y | 1.31 |
| T223E | 2.04 |
| T223K | 2.97 |
| H224E | 5.11 |
| H224Y | 1.68 |
| T225E | 4.89 |
| T225K | 5.68 |
| T225W | 6.89 |
| P227E | 1.49 |
| P227G | 1.67 |
| P227K | 1.45 |
| P228G | 1.77 |
| P228K | 1.55 |
| P228Y | 1.45 |
| P230E | 1.01 |
| P230G | 1.16 |
| P232K | 1.56 |
| E233G | 2.09 |
| E233M | 1.13 |
| E233R | 1.05 |
| E233S | 1.10 |
| E233T | 1.19 |
| E233W | 1.64 |
| E233Y | 1.86 |
| L234D | 1.54 |
| L234E | 1.25 |
| L234F | 1.46 |
| L234G | 2.54 |
| L234H | 1.48 |
| L234I | 1.26 |
| L234I/L235D | 1.03 |
| L234N | 1.06 |
| L234R | 1.19 |
| L234V | 1.45 |
| L234Y | 1.90 |
| L235N | 1.32 |
| L235Q | 1.67 |
| L235S | 1.51 |
| L235T | 1.65 |
| L235V | 1.31 |
| L235Y | 1.02 |
| G236A | 1.75 |
| G236D | 1.53 |
| G236A | 1.75 |
| G236D | 1.53 |
| G236E | 1.46 |
| G236F | 1.75 |
| G236H | 1.48 |
| G236I | 1.33 |
| G236K | 1.38 |
| G236M | 1.60 |
| G236N | 1.89 |
| G236P | 1.41 |
| G236Q | 1.46 |
| G236R | 1.99 |
| G236S | 1.77 |
| G236T | 1.56 |
| G236V | 1.35 |
| G236W | 1.52 |
| G236Y | 1.52 |
| G237D | 1.84 |
| G237E | 1.36 |
| G237H | 1.48 |
| G237I | 1.01 |
| G237K | 1.47 |
| G237L | 5.91 |
| G237M | 73.39 |
| G237N | 1.39 |
| G237P | 2.80 |
| G237Q | 1.39 |
| G237R | 1.36 |
| G237S | 1.29 |
| G237T | 1.32 |
| G237W | 1.20 |
| G237Y | 1.92 |
| P238D | 1.03 |
| P238E | 3.71 |
| P238F | 2.41 |
| P238G | 1.53 |
| P238H | 1.46 |
| P238I | 1.44 |
| P238K | 5.01 |
| P238L | 1.71 |
| P238M | 2.33 |
| P238N | 1.15 |
| P238S | 1.12 |
| P238T | 1.12 |
| P238V | 1.43 |
| P238W | 1.30 |

*FIG. 14a*

| | | | |
|---|---|---|---|
| P238W | 1.30 | F241Y/F243Y/V262T/V264T | 1.89 |
| S239D | 1.73 | F243E | 1.14 |
| S239D/D265H/N297D/I332E | 1.26 | F243L/V262I/V264W | 1.35 |
| S239D/D265I/N297D/I332E | | F243W | 4.63 |
| S239D/E272I/I332E | 1.81 | K246H | 4.02 |
| S239D/E272S/I332E | 1.49 | K246Y | 2.47 |
| | | D249Q | 2.06 |
| | | D249Y | 2.57 |
| S239D/E272Y/I332E | 1.31 | R255E | 1.16 |
| S239D/I332D | 1.12 | R255Y | 12.88 |
| S239D/I332E | 1.22 | E258Y | 1.07 |
| | | T260D | 1.71 |
| S239D/K326T/I332E | 2.22 | T260E | 5.49 |
| | | T260H | 7.30 |
| S239D/N297D/I332E | 3.09 | T260Y | 7.51 |
| S239E | 1.47 | V262E | 9.27 |
| S239E/I332E | 1.34 | V263I | 2.71 |
| | | V264A | 1.12 |
| S239E/N297D/I332E | | V264D | 7.67 |
| S239E/V264I/A330Y/I332E | 2.36 | V264F | 1.07 |
| | | V264I | 1.32 |
| S239E/V264I/I332E | 2.71 | V264I/A330L/I332E | 1.13 |
| S239E/V264I/S298A/A330Y/I332E | 10.14 | V264I/I332E | 1.70 |
| | | V264N | 3.39 |
| S239G | 1.16 | V264S | 5.13 |
| S239L | 4.60 | V264T | 1.66 |
| S239M | 1.03 | | |
| S239Q/I332E | 1.33 | D265F/N297E/I332E | 1.38 |
| S239Q/I332N | 1.11 | D265G | 1.74 |
| S239Q/I332Q | 1.04 | D265P | 1.18 |
| S239Q/V264I/I332E | | D265R | 1.16 |
| S239R | 1.04 | V266I | 1.17 |
| S239T | 1.12 | S267E | 2.24 |
| S239V | 1.17 | S267K | 1.70 |
| S239Y | | S267L/A327S | 1.05 |
| V240I | 1.28 | H268E | 1.71 |
| V240M | 2.50 | H268M | 1.88 |
| V240T | 2.61 | E269F | 1.51 |
| F241E | 1.09 | E269G | 1.34 |
| F241L | 1.99 | E269I | 1.26 |
| F241L/V262I | 1.37 | E269K | 1.23 |
| F241W | 1.70 | E269M | 1.11 |
| F241W/F243W | 1.12 | E269P | 1.23 |
| F241W/F243W/V262A/V264A | 1.91 | E269S | 1.31 |
| | | E269V | 1.38 |
| F241Y/F243Y/V262T/V264T | 1.89 | E269W | 1.19 |
| | | E269Y | 24.75 |

*FIG. 14b*

| | | | | |
|---|---|---|---|---|
| E269Y | 24.75 | | V282E | 1.91 |
| D270I | 1.23 | | V282G | 1.16 |
| D270S | 1.03 | | V282K | 1.44 |
| P271A | 1.01 | | V282Y | 1.92 |
| P271I | 1.99 | | E283H | 6.25 |
| P271S | 1.14 | | E283K | 2.74 |
| P271T | 3.88 | | E283L | 9.25 |
| P271V | 1.06 | | E283P | 1.33 |
| P271Y | 1.48 | | E283R | 1.86 |
| E272D | 1.37 | | E283Y | 1.42 |
| E272H | 1.45 | | V284E | 25.76 |
| E272I | 1.05 | | V284L | 1.51 |
| E272L | 1.81 | | V284T | 1.15 |
| E272P | 2.17 | | H285D | 2.40 |
| E272R | 1.83 | | H285E | 1.93 |
| E272T | 2.46 | | H285K | 1.76 |
| E272V | 1.77 | | H285Q | 1.38 |
| E272W | 1.82 | | H285W | 1.33 |
| E272Y | 2.08 | | H285Y | 1.25 |
| K274E | 1.05 | | N286E | 2.12 |
| K274F | 1.02 | | N286P | 2.90 |
| K274G | 1.04 | | N286Y | 1.45 |
| K274I | 1.08 | | K288Y | 1.10 |
| K274M | 1.01 | | P291H | 2.56 |
| K274N | 1.26 | | P291I | 1.15 |
| K274T | 1.08 | | P291Q | 1.24 |
| N276D | 1.18 | | R292D | 1.67 |
| N276F | 1.18 | | R292E | 1.45 |
| N276H | 1.19 | | R292Y | 1.36 |
| N276L | 1.21 | | E294G | 1.25 |
| N276R | 1.19 | | E294I | 1.09 |
| N276V | 1.27 | | E294K | 1.16 |
| N276W | 2.00 | | Q295T | 3.82 |
| Y278D | 1.79 | | Q295V | 1.19 |
| Y278I | 1.52 | | Y296E | 1.23 |
| Y278L | 1.74 | | Y296I | 1.71 |
| Y278M | 1.28 | | Y296L | 2.78 |
| Y278N | 1.33 | | Y296S | |
| Y278R | 1.23 | | S298E | 1.54 |
| Y278S | 1.23 | | S298F | 1.15 |
| Y278V | 1.27 | | S298H | 3.99 |
| G281D | 1.33 | | S298T | 2.13 |
| G281Y | 1.46 | | T299F | 1.86 |
| V282E | 1.91 | | T299H | 2.03 |
| | | | T299W | 1.09 |
| | | | T299Y | 3.85 |

FIG. 14c

| | | | |
|---|---|---|---|
| T299Y | 3.85 | L328R | 1.82 |
| Y300A | 1.04 | L328W | 1.35 |
| Y300E | 1.27 | P329K | 1.27 |
| Y300G | 1.07 | P329R | 1.64 |
| Y300K | 1.01 | P329W | 3.16 |
| Y300M | 1.10 | A330F | 25.29 |
| Y300N | 1.14 | A330G | 1.01 |
| Y300Q | 1.11 | A330H | 9.87 |
| Y300V | 1.09 | A330I | |
| R301E | 2.92 | A330L/I332E | 1.50 |
| V302I | 2.44 | A330P | 5.48 |
| V303E | 1.63 | A330R | |
| V303Y | 1.15 | A330V | 1.78 |
| S304N | 1.19 | A330W | 1.02 |
| S304T | 2.86 | A330Y/I332E | 1.53 |
| E318L | 3.61 | P331F | 3.91 |
| E318R | 1.17 | P331L | 1.77 |
| E318Y | 6.14 | P331Y | 6.06 |
| K320H | 1.13 | I332D | 1.75 |
| K320L | 1.07 | I332E | 1.32 |
| K320N | 2.01 | I332H | 1.24 |
| K320W | 1.11 | I332N | 3.20 |
| S324D | 1.27 | I332Q | 1.20 |
| S324G | 2.74 | I332T | 1.02 |
| S324T | 1.07 | I332V | 59.27 |
| N325D | 1.45 | I332Y | 1.43 |
| N325F | 1.22 | E333F | 1.96 |
| N325M | 1.43 | E333L | 1.03 |
| N325T | | E333M | 5.46 |
| N325V | | T335F | 1.19 |
| A327D | 1.01 | T335H | 1.16 |
| A327H | 1.29 | T335I | 1.41 |
| A327K | 1.01 | T335L | 1.50 |
| A327L | 1.55 | T335M | 1.35 |
| A327M | 1.08 | T335N | 1.23 |
| A327Y | 1.23 | T335P | 1.45 |
| L328A | 1.32 | T335S | 1.42 |
| L328D/I332E | 11.84 | T335V | 1.25 |
| L328E/I332E | 1.44 | T335W | 1.35 |
| L328F | 2.06 | I336E | 8.11 |
| L328G | 1.16 | I336K | 12.12 |
| L328H/I332E | 1.16 | | |
| L328I/I332E | 2.21 | | |
| L328N/I332E | 1.18 | | |
| L328Q/I332E | 4.29 | | |
| L328R | 1.82 | | |

*FIG. 14d*

SEQUENCE LISTING

<160> NUMBER OF SEQ ID NOS: 10

<210> SEQ ID NO 1
<211> LENGTH: 227
<212> TYPE: PRT
<213> ORGANISM: Homo sapiens

<400> SEQUENCE: 1

Asp Lys Thr His Thr Cys Pro Pro Cys Pro Ala Pro Glu Leu Leu Gly

```
      1               5                  10                 15
    Gly Pro Ser Val Phe Leu Phe Pro Pro Lys Pro Lys Asp Thr Leu Met
                    20                  25                 30

Ile Ser Arg Thr Pro Glu Val Thr Cys Val Val Val Asp Val Ser His
                    35                  40                 45

Glu Asp Pro Glu Val Lys Phe Asn Trp Tyr Val Asp Gly Val Glu Val
                50                  55                  60

His Asn Ala Lys Thr Lys Pro Arg Glu Gln Tyr Asn Ser Thr Tyr
     65                 70                  75                 80

Arg Val Val Ser Val Leu Thr Val Leu His Gln Asp Trp Leu Asn Gly
                    85                  90                 95

Lys Glu Tyr Lys Cys Lys Val Ser Asn Lys Ala Leu Pro Ala Pro Ile
                    100                 105                110

Glu Lys Thr Ile Ser Lys Ala Lys Gly Gln Pro Arg Glu Pro Gln Val
                    115                 120                125

Tyr Thr Leu Pro Pro Ser Arg Asp Glu Leu Thr Lys Asn Gln Val Ser
                130                 135                 140

Leu Thr Cys Leu Val Lys Gly Phe Tyr Pro Ser Asp Ile Ala Val Glu
    145                 150                 155                 160

Trp Glu Ser Asn Gly Gln Pro Glu Asn Asn Tyr Lys Thr Thr Pro Pro
                    165                 170                175

Val Leu Asp Ser Asp Gly Ser Phe Phe Leu Tyr Ser Lys Leu Thr Val
                    180                 185                 190

Asp Lys Ser Arg Trp Gln Gln Gly Asn Val Phe Ser Cys Ser Val Met
                    195                 200                 205

His Glu Ala Leu His Asn His Tyr Thr Gln Lys Ser Leu Ser Leu Ser
                    210                 215                 220

Pro Gly Lys
    225

<210> SEQ ID NO 2
<211> LENGTH: 223
<212> TYPE: PRT
<213> ORGANISM: Homo sapiens

<400> SEQUENCE: 2

Val Glu Cys Pro Pro Cys Pro Ala Pro Pro Val Ala Gly Pro Ser Val
     1               5                  10                 15

Phe Leu Phe Pro Pro Lys Pro Lys Asp Thr Leu Met Ile Ser Arg Thr
                    20                  25                 30

Pro Glu Val Thr Cys Val Val Val Asp Val Ser His Glu Asp Pro Glu
                    35                  40                 45

Val Gln Phe Asn Trp Tyr Val Asp Gly Val Glu Val His Asn Ala Lys
                50                  55                  60

Thr Lys Pro Arg Glu Glu Gln Phe Asn Ser Thr Phe Arg Val Val Ser
     65                 70                  75                 80

Val Leu Thr Val Val His Gln Asp Trp Leu Asn Gly Lys Glu Tyr Lys
                    85                  90                 95

Cys Lys Val Ser Asn Lys Gly Leu Pro Ala Pro Ile Glu Lys Thr Ile
                    100                 105                110

Ser Lys Thr Lys Gly Gln Pro Arg Glu Pro Gln Val Tyr Thr Leu Pro
                    115                 120                125

Pro Ser Arg Glu Glu Met Thr Lys Asn Gln Val Ser Leu Thr Cys Leu
                130                 135                 140
```

```
Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220

<210> SEQ ID NO 3
<211> LENGTH: 229
<212> TYPE: PRT
<213> ORGANISM: Homo sapiens

<400> SEQUENCE: 3

Leu Gly Asp Thr Thr His Thr Cys Pro Arg Cys Pro Ala Pro Glu Leu
1               5                   10                  15

Leu Gly Gly Pro Ser Val Phe Leu Phe Pro Pro Lys Pro Lys Asp Thr
                20                  25                  30

Leu Met Ile Ser Arg Thr Pro Glu Val Thr Cys Val Val Val Asp Val
            35                  40                  45

Ser His Glu Asp Pro Glu Val Gln Phe Lys Trp Tyr Val Asp Gly Val
    50                  55                  60

Glu Val His Asn Ala Lys Thr Lys Pro Arg Glu Glu Gln Tyr Asn Ser
65                  70                  75                  80

Thr Phe Arg Val Val Ser Val Leu Thr Val Leu His Gln Asp Trp Leu
                85                  90                  95

Asn Gly Lys Glu Tyr Lys Cys Lys Val Ser Asn Lys Ala Leu Pro Ala
            100                 105                 110

Pro Ile Glu Lys Thr Ile Ser Lys Thr Lys Gly Gln Pro Arg Glu Pro
        115                 120                 125

Gln Val Tyr Thr Leu Pro Pro Ser Arg Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Ser Gly Gln Pro Glu Asn Asn Tyr Asn Thr Thr
                165                 170                 175

Pro Pro Met Leu Asp Ser Asp Gly Ser Phe Phe Leu Tyr Ser Lys Leu
            180                 185                 190

Thr Val Asp Lys Ser Arg Trp Gln Gln Gly Asn Ile Phe Ser Cys Ser
        195                 200                 205

Val Met His Glu Ala Leu His Asn Arg Phe Thr Gln Lys Ser Leu Ser
    210                 215                 220

Leu Ser Pro Gly Lys
225

<210> SEQ ID NO 4
<211> LENGTH: 224
<212> TYPE: PRT
<213> ORGANISM: Homo sapiens

<400> SEQUENCE: 4

Pro Pro Cys Pro Ser Cys Pro Ala Pro Glu Phe Leu Gly Gly Pro Ser
1               5                   10                  15
```

Val Phe Leu Phe Pro Pro Lys Pro Lys Asp Thr Leu Met Ile Ser Arg
            20                  25                  30

Thr Pro Glu Val Thr Cys Val Val Asp Val Ser Gln Glu Asp Pro
        35                  40                  45

Glu Val Gln Phe Asn Trp Tyr Val Asp Gly Val Glu Val His Asn Ala
    50                  55                  60

Lys Thr Lys Pro Arg Glu Glu Gln Phe Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Gly Leu Pro Ser Ser Ile Glu Lys Thr
            100                 105                 110

Ile Ser Lys Ala Lys Gly Gln Pro Arg Glu Pro Gln Val Tyr Thr Leu
        115                 120                 125

Pro Pro Ser Gln Glu Glu Met Thr Lys Asn Gln Val Ser Leu Thr Cys
130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Arg Leu Thr Val Asp Lys Ser
            180                 185                 190

Arg Trp Gln Glu Gly Asn Val Phe Ser Cys Ser Val Met His Glu Ala
        195                 200                 205

Leu His Asn His Tyr Thr Gln Lys Ser Leu Ser Leu Ser Leu Gly Lys
210                 215                 220

<210> SEQ ID NO 5
<211> LENGTH: 207
<212> TYPE: PRT
<213> ORGANISM: Homo sapiens

<400> SEQUENCE: 5

Gly Pro Ser Val Phe Leu Phe Pro Pro Lys Pro Lys Asp Thr Leu Met
1               5                   10                  15

Ile Ser Arg Thr Pro Glu Val Thr Cys Val Val Asp Val Ser His
            20                  25                  30

Glu Asn Pro Glu Val Lys Phe Asn Trp Tyr Val Asp Gly Val Glu Val
        35                  40                  45

His Asn Ala Lys Thr Lys Pro Arg Glu Glu Gln Tyr Asn Ser Thr Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Ala Leu Pro Ala Pro Ile
                85                  90                  95

Glu Lys Thr Ile Ser Lys Ala Lys Gly Gln Pro Arg Glu Pro Gln Val
            100                 105                 110

Tyr Thr Leu Pro Pro Ser Arg Glu Glu Met Thr Lys Asn Gln Val Ser
        115                 120                 125

Leu Thr Cys Leu Val Lys Gly Phe Tyr Pro Ser Asp Ile Ala Val Glu
    130                 135                 140

Trp Glu Ser Asn Gly Gln Pro Glu Asn Asn Tyr Lys Thr Thr Pro Pro
145                 150                 155                 160

Val Leu Asp Ser Asp Gly Ser Phe Phe Leu Tyr Ser Lys Leu Thr Val
                165                 170                 175

Asp Lys Ser Arg Trp Gln Gln Gly Asn Val Phe Ser Cys Ser Val Met
            180                 185                 190

His Glu Ala Leu His Asn His Tyr Thr Gln Lys Ser Leu Ser Leu
        195                 200                 205

<210> SEQ ID NO 6
<211> LENGTH: 205
<212> TYPE: PRT
<213> ORGANISM: Rattus norvegicus

<400> SEQUENCE: 6

Ser Val Phe Ile Phe Pro Pro Lys Thr Lys Asp Val Leu Thr Ile Thr
1               5                   10                  15

Leu Thr Pro Lys Val Thr Cys Val Val Val Asp Ile Ser Gln Asn Asp
            20                  25                  30

Pro Glu Val Arg Phe Ser Trp Phe Ile Asp Asp Val Glu Val His Thr
        35                  40                  45

Ala Gln Thr His Ala Pro Glu Lys Gln Ser Asn Ser Thr Leu Arg Ser
    50                  55                  60

Val Ser Glu Leu Pro Ile Val His Arg Asp Trp Leu Asn Gly Lys Thr
65                  70                  75                  80

Phe Lys Cys Lys Val Asn Ser Gly Ala Phe Pro Ala Pro Ile Glu Lys
                85                  90                  95

Ser Ile Ser Lys Pro Glu Gly Thr Pro Arg Gly Pro Gln Val Tyr Thr
            100                 105                 110

Met Ala Pro Pro Lys Glu Glu Met Thr Gln Ser Gln Val Ser Ile Thr
        115                 120                 125

Cys Met Val Lys Gly Phe Tyr Pro Pro Asp Ile Tyr Thr Glu Trp Lys
    130                 135                 140

Met Asn Gly Gln Pro Gln Glu Asn Tyr Lys Asn Thr Pro Pro Thr Met
145                 150                 155                 160

Asp Thr Asp Gly Ser Tyr Phe Leu Tyr Ser Lys Leu Asn Val Lys Lys
                165                 170                 175

Glu Thr Trp Gln Gln Gly Asn Thr Phe Thr Cys Ser Val Leu His Glu
            180                 185                 190

Gly Leu His Asn His His Thr Glu Lys Ser Leu Ser His
        195                 200                 205

<210> SEQ ID NO 7
<211> LENGTH: 256
<212> TYPE: PRT
<213> ORGANISM: Homo sapiens

<400> SEQUENCE: 7

His Leu Ser Leu Leu Tyr His Leu Thr Ala Val Ser Ser Pro Ala Pro
1               5                   10                  15

Gly Thr Pro Ala Phe Trp Val Ser Gly Trp Leu Gly Pro Gln Gln Tyr
            20                  25                  30

Leu Ser Tyr Asn Ser Leu Arg Gly Glu Ala Glu Pro Cys Gly Ala Trp
        35                  40                  45

Tyr Trp Glu Lys Glu Thr Thr Asp Leu Arg Ile Lys Glu Lys Leu Phe
    50                  55                  60

Leu Glu Ala Phe Lys Ala Leu Gly Gly Lys Gly Pro Tyr Thr Leu Gln
65                  70                  75                  80

Gly Leu Leu Gly Cys Glu Leu Gly Pro Asp Asn Thr Ser Val Pro Thr
                85                  90                  95

```
Ala Lys Phe Ala Leu Asn Gly Glu Glu Phe Met Asn Phe Asp Leu Lys
            100                 105                 110

Gln Gly Thr Trp Gly Gly Asp Trp Pro Glu Ala Leu Ala Ile Ser Gln
            115                 120                 125

Arg Trp Gln Gln Gln Asp Lys Ala Ala Asn Lys Glu Leu Thr Phe Leu
        130                 135                 140

Leu Phe Ser Cys Pro His Arg Leu Arg Glu His Leu Glu Arg Gly Arg
145                 150                 155                 160

Gly Asn Leu Glu Trp Lys Glu Pro Pro Ser Met Arg Leu Lys Ala Arg
                165                 170                 175

Pro Ser Ser Pro Gly Phe Ser Val Leu Thr Cys Ser Ala Phe Ser Phe
            180                 185                 190

Tyr Pro Pro Glu Leu Gln Leu Arg Phe Leu Arg Asn Gly Leu Ala Ala
            195                 200                 205

Gly Thr Gly Gln Gly Asp Phe Gly Pro Asn Ser Asp Gly Ser Phe His
        210                 215                 220

Ala Ser Ser Ser Leu Thr Val Lys Ser Gly Asp Glu His His Tyr Cys
225                 230                 235                 240

Cys Ile Val Gln His Ala Gly Leu Ala Gln Pro Leu Arg Val Glu Leu
                245                 250                 255

<210> SEQ ID NO 8
<211> LENGTH: 265
<212> TYPE: PRT
<213> ORGANISM: Rattus norvegicus

<400> SEQUENCE: 8

Leu Pro Leu Met Tyr His Leu Ala Ala Val Ser Asp Leu Ser Thr Gly
1               5                   10                  15

Leu Pro Ser Phe Trp Ala Thr Gly Trp Leu Gly Ala Gln Gln Tyr Leu
            20                  25                  30

Thr Tyr Asn Asn Leu Arg Gln Glu Ala Asp Pro Cys Gly Ala Trp Ile
        35                  40                  45

Trp Glu Asn Gln Val Ser Trp Tyr Trp Glu Lys Glu Thr Thr Asp Leu
50                  55                  60

Lys Ser Lys Glu Gln Leu Phe Leu Glu Ala Ile Arg Thr Leu Glu Asn
65                  70                  75                  80

Gln Ile Asn Gly Thr Phe Thr Leu Gln Gly Leu Leu Gly Cys Glu Leu
                85                  90                  95

Ala Pro Asp Asn Ser Ser Leu Pro Thr Ala Val Phe Ala Leu Asn Gly
            100                 105                 110

Glu Glu Phe Met Arg Phe Asn Pro Arg Thr Gly Asn Trp Ser Gly Glu
            115                 120                 125

Trp Pro Glu Thr Asp Ile Val Gly Asn Leu Trp Met Lys Gln Pro Glu
        130                 135                 140

Ala Ala Arg Lys Glu Ser Glu Phe Leu Leu Thr Ser Cys Pro Glu Arg
145                 150                 155                 160

Leu Leu Gly His Leu Glu Arg Gly Arg Gln Asn Leu Glu Trp Lys Glu
                165                 170                 175

Pro Pro Ser Met Arg Leu Lys Ala Arg Pro Gly Asn Ser Gly Ser Ser
            180                 185                 190

Val Leu Thr Cys Ala Ala Phe Ser Phe Tyr Pro Pro Glu Leu Lys Phe
            195                 200                 205

Arg Phe Leu Arg Asn Gly Leu Ala Ser Gly Ser Gly Asn Cys Ser Thr
```

```
                    210                 215                 220
Gly Pro Asn Gly Asp Gly Ser Phe His Ala Trp Ser Leu Leu Glu Val
225                 230                 235                 240

Lys Arg Gly Asp Glu His His Tyr Gln Cys Gln Val Glu His Glu Gly
                    245                 250                 255

Leu Ala Gln Pro Leu Thr Val Asp Leu
                260                 265

<210> SEQ ID NO 9
<211> LENGTH: 99
<212> TYPE: PRT
<213> ORGANISM: Homo sapiens

<400> SEQUENCE: 9

Ile Gln Arg Thr Pro Lys Ile Gln Val Tyr Ser Arg His Pro Ala Glu
1               5                   10                  15

Asn Gly Lys Ser Asn Phe Leu Asn Cys Tyr Val Ser Gly Phe His Pro
                20                  25                  30

Ser Asp Ile Glu Val Asp Leu Leu Lys Asn Gly Glu Arg Ile Glu Lys
            35                  40                  45

Val Glu His Ser Asp Leu Ser Phe Ser Lys Asp Trp Ser Phe Tyr Leu
50                  55                  60

Leu Tyr Tyr Thr Glu Phe Thr Pro Thr Glu Lys Asp Glu Tyr Ala Cys
65                  70                  75                  80

Arg Val Asn His Val Thr Leu Ser Gln Pro Lys Ile Val Lys Trp Asp
                85                  90                  95

Arg Asp Met

<210> SEQ ID NO 10
<211> LENGTH: 99
<212> TYPE: PRT
<213> ORGANISM: Rattus norvegicus

<400> SEQUENCE: 10

Ile Gln Lys Thr Pro Gln Ile Gln Val Tyr Ser Arg His Pro Pro Glu
1               5                   10                  15

Asn Gly Lys Pro Asn Phe Leu Asn Cys Tyr Val Ser Gln Phe His Pro
                20                  25                  30

Pro Gln Ile Glu Ile Glu Leu Leu Lys Asn Gly Lys Lys Ile Pro Asn
            35                  40                  45

Ile Glu Met Ser Asp Leu Ser Phe Ser Lys Asp Trp Ser Phe Tyr Ile
50                  55                  60

Leu Ala His Thr Glu Phe Thr Pro Thr Glu Thr Asp Val Tyr Ala Cys
65                  70                  75                  80

Arg Val Lys His Val Thr Leu Lys Glu Pro Lys Thr Val Thr Trp Asp
                85                  90                  95

Arg Asp Met
```

FC VARIANTS WITH ALTERED BINDING TO FCRN

This application claims benefit under 35 U.S.C. §119(e) to U.S. Ser. No. 60/627,763, filed Nov. 12, 2004; U.S. Ser. No. 60/642,886, filed Jan. 11, 2005; U.S. Ser. No. 60/649,508, filed Feb. 2, 2005; U.S. Ser. No. 60/662,468, filed Mar. 15, 2005; 2005; U.S. Ser. No. 60/669,311, filed Apr. 6, 2005; U.S. Ser. No. 60/681,607, filed May 16, 2005; U.S. Ser. No. 60/690,200, filed Jun. 13, 2005; U.S. Ser. No. 60/696,609, filed Jul. 5, 2005; U.S. Ser. No. 60/703,018, filed Jul. 27, 2005; and U.S. Ser. No. 60/726,453, filed Oct. 12, 2005, all entirely incorporated by reference.

FIELD OF THE INVENTION

The present application relates to optimized IgG immunoglobulin variants, engineering methods for their generation, and their application, particularly for therapeutic purposes.

BACKGROUND OF THE INVENTION

Antibodies are immunological proteins that bind a specific antigen. In most mammals, including humans and mice, antibodies are constructed from paired heavy and light polypeptide chains. Each chain is made up of individual immunoglobulin (Ig) domains, and thus the generic term immunoglobulin is used for such proteins. Each chain is made up of two distinct regions, referred to as the variable and constant regions. The light and heavy chain variable regions show significant sequence diversity between antibodies, and are responsible for binding the target antigen. The constant regions show less sequence diversity, and are responsible for binding a number of natural proteins to elicit important biochemical events. In humans there are five different classes of antibodies including IgA (which includes subclasses IgA1 and IgA2), IgD, IgE, IgG (which includes subclasses IgG1, IgG2, IgG3, and IgG4), and IgM. The distinguishing features between these antibody classes are their constant regions, although subtler differences may exist in the V region. FIG. 1 shows an IgG1 antibody, used here as an example to describe the general structural features of immunoglobulins. IgG antibodies are tetrameric proteins composed of two heavy chains and two light chains. The IgG heavy chain is composed of four immunoglobulin domains linked from N- to C-terminus in the order VH-CH1-CH2-CH3, referring to the heavy chain variable domain, heavy chain constant domain 1, heavy chain constant domain 2, and heavy chain constant domain 3 respectively (also referred to as VH-Cγ1-Cγ2-Cγ3, referring to the heavy chain variable domain, constant gamma 1 domain, constant gamma 2 domain, and constant gamma 3 domain respectively). The IgG light chain is composed of two immunoglobulin domains linked from N- to C-terminus in the order VL-CL, referring to the light chain variable domain and the light chain constant domain respectively.

The variable region of an antibody contains the antigen binding determinants of the molecule, and thus determines the specificity of an antibody for its target antigen. The variable region is so named because it is the most distinct in sequence from other antibodies within the same class. The majority of sequence variability occurs in the complementarity determining regions (CDRs). There are 6 CDRs total, three each per heavy and light chain, designated VH CDR1, VH CDR2, VH CDR3, VL CDR1, VL CDR2, and VL CDR3. The variable region outside of the CDRs is referred to as the framework (FR) region. Although not as diverse as the CDRs, sequence variability does occur in the FR region between different antibodies. Overall, this characteristic architecture of antibodies provides a stable scaffold (the FR region) upon which substantial antigen binding diversity (the CDRs) can be explored by the immune system to obtain specificity for a broad array of antigens. A number of high-resolution structures are available for a variety of variable region fragments from different organisms, some unbound and some in complex with antigen. The sequence and structural features of antibody variable regions are well characterized (Morea et al, 1997, *Biophys Chem* 68:9-16; Morea et al., 2000, *Methods* 20:267-279, entirely incorporated by reference), and the conserved features of antibodies have enabled the development of a wealth of antibody engineering techniques (Maynard et al., 2000, *Annu Rev Biomed Eng* 2:339-376, entirely incorporated by reference). For example, it is possible to graft the CDRs from one antibody, for example a murine antibody, onto the framework region of another antibody, for example a human antibody. This process, referred to in the art as "humanization", enables generation of less immunogenic antibody therapeutics from nonhuman antibodies. Fragments including the variable region can exist in the absence of other regions of the antibody, including for example the antigen binding fragment (Fab) including VH-Cγ1 and VH-CL, the variable fragment (Fv) including VH and VL, the single chain variable fragment (scFv) including VH and VL linked together in the same chain, as well as a variety of other variable region fragments (Little et al., 2000, *Immunol Today* 21:364-370, entirely incorporated by reference).

The Fc region of an antibody interacts with a number of Fc receptors and ligands, imparting an array of important functional capabilities referred to as effector functions. For IgG the Fc region, as shown in FIGS. 1 and 2, comprises Ig domains Cγ2 and Cγ3 and the N-terminal hinge leading into Cγ2. An important family of Fc receptors for the IgG class are the Fc gamma receptors (FcγRs). These receptors mediate communication between antibodies and the cellular arm of the immune system (Raghavan et al., 1996, *Annu Rev Cell Dev Biol* 12:181-220; Ravetch et al., 2001, *Annu Rev Immunol* 19:275-290, both entirely incorporated by reference). In humans this protein family includes FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRII b-2), and FcγRIIc; and FcγRII (CD16), including isoforms FcγRIIIa (including allotypes V158 and F158) and FcγRIIIb (including allotypes FcγRIIIb-NA1 and FcγRIIIb-NA2) (Jefferis et al., 2002, *Immunol Lett* 82:57-65, entirely incorporated by reference). These receptors typically have an extracellular domain that mediates binding to Fc, a membrane spanning region, and an intracellular domain that may mediate some signaling event within the cell. These receptors are expressed in a variety of immune cells including monocytes, macrophages, neutrophils, dendritic cells, eosinophils, mast cells, platelets, B cells, large granular lymphocytes, Langerhans' cells, natural killer (NK) cells, and γγ T cells. Formation of the Fc/FcγR complex recruits these effector cells to sites of bound antigen, typically resulting in signaling events within the cells and important subsequent immune responses such as release of inflammation mediators, B cell activation, endocytosis, phagocytosis, and cytotoxic attack. The ability to mediate cytotoxic and phagocytic effector functions is a potential mechanism by which antibodies destroy targeted cells. The cell-mediated reaction wherein nonspecific cytotoxic cells that express FcγRs recognize bound antibody on a target cell and subsequently cause lysis of the target cell is referred to as antibody dependent cell-mediated cytotoxicity (ADCC) (Raghavan et al., 1996, *Annu Rev Cell Dev Biol* 12:181-220;

Ghetie et al., 2000, *Annu Rev Immunol* 18:739-766; Ravetch et al., 2001, *Annu Rev Immunol* 19:275-290, all entirely incorporated by reference). The cell-mediated reaction wherein nonspecific cytotoxic cells that express FcγRs recognize bound antibody on a target cell and subsequently cause phagocytosis of the target cell is referred to as antibody dependent cell-mediated phagocytosis (ADCP). A number of structures have been solved of the extracellular domains of human FcγRs, including FcγRIIa (pdb accession code 1H9V, entirely incorporated by reference)(Sondermann et al., 2001, *J Mol Biol* 309:737-749, entirely incorporated by reference) (pdb accession code 1FCG, entirely incorporated by reference)(Maxwell et al., 1999, *Nat Struct Biol* 6:437-442, entirely incorporated by reference), FcγRIIb (pdb accession code 2FCB, entirely incorporated by reference)(Sondermann et al., 1999, *Embo J* 18:1095-1103, entirely incorporated by reference); and FcγRIIIb (pdb accession code 1E4J, entirely incorporated by reference)(Sondermann et al., 2000, *Nature* 406:267-273, entirely incorporated by reference.). All FcγRs bind the same region on Fc, at the N-terminal end of the Cγ2 domain and the preceding hinge, shown in FIG. 1. This interaction is well characterized structurally (Sondermann et al., 2001, *J Mol Biol* 309:737-749, entirely incorporated by reference), and several structures of the human Fc bound to the extracellular domain of human FcγRIIIb have been solved (pdb accession code 1E4K, entirely incorporated by reference)(Sondermann et al., 2000, *Nature* 406:267-273, entirely incorporated by reference) (pdb accession codes 1IIS and 1IIX, entirely incorporated by reference)(Radaev et al., 2001, *J Biol Chem* 276:16469-16477, entirely incorporated by reference), as well as has the structure of the human IgE Fc/FcεRIα complex (pdb accession code 1F6A, entirely incorporated by reference)(Garman et al., 2000, *Nature* 406:259-266, entirely incorporated by reference).

The different IgG subclasses have different affinities for the FcγRs, with IgG1 and IgG3 typically binding substantially better to the receptors than IgG2 and IgG4 (Jefferis et al., 2002, *Immunol Lett* 82:57-65, entirely incorporated by reference). All FcγRs bind the same region on IgG Fc, yet with different affinities: the high affinity binder FcγRI has a Kd for IgG1 of $10^{-8}$ $M^{-1}$, whereas the low affinity receptors FcγRII and FcγRIII generally bind at $10^{-6}$ and $10^{-5}$ respectively. The extracellular domains of FcγRIIIa and FcγRIIIb are 96% identical; however FcγRIIIb does not have an intracellular signaling domain. Furthermore, whereas FcγRI, FcγRIIa/c, and FcγRIIIa are positive regulators of immune complex-triggered activation, characterized by having an intracellular domain that has an immunoreceptor tyrosine-based activation motif (ITAM), FcγRIIb has an immunoreceptor tyrosine-based inhibition motif (ITIM) and is therefore inhibitory. Thus the former are referred to as activation receptors, and FcγRIIb is referred to as an inhibitory receptor. The receptors also differ in expression pattern and levels on different immune cells. Yet another level of complexity is the existence of a number of FcγR polymorphisms in the human proteome. A particularly relevant polymorphism with clinical significance is V158/F158 FcγRIIIa. Human IgG1 binds with greater affinity to the V158 allotype than to the F158 allotype. This difference in affinity, and presumably its effect on ADCC and/or ADCP, has been shown to be a significant determinant of the efficacy of the anti-CD20 antibody rituximab (Rituxan®, Biogenidec). Patients with the V158 allotype respond favorably to rituximab treatment; however, patients with the lower affinity F158 allotype respond poorly (Cartron et al., 2002, *Blood* 99:754-758, entirely incorporated by reference). Approximately 10-20% of humans are V158/V158 homozygous, 45% are V158/F158 heterozygous, and 35-45% of humans are F158/F158 homozygous (Lehrnbecher et al., 1999, *Blood* 94:4220-4232; Cartron et al., 2002, *Blood* 99:754-758, all entirely incorporated by reference). Thus 80-90% of humans are poor responders, i.e., they have at least one allele of the F158 FcγRIIIa.

An overlapping but separate site on Fc, shown in FIG. 1, serves as the interface for the complement protein C1q. In the same way that Fc/FcγR binding mediates ADCC, Fc/C1q binding mediates complement dependent cytotoxicity (CDC). C1q forms a complex with the serine proteases C1r and C1s to form the C1 complex. C1q is capable of binding six antibodies, although binding to two IgGs is sufficient to activate the complement cascade. Similar to Fc interaction with FcγRs, different IgG subclasses have different affinity for C1q, with IgG1 and IgG3 typically binding substantially better to the FcγRs than IgG2 and IgG4 (Jefferis et al., 2002, *Immunol Lett* 82:57-65, entirely incorporated by reference).

In IgG, a site on Fc between the Cg2 and Cg3 domains (FIG. 1) mediates interaction with the neonatal receptor FcRn, the binding of which recycles endocytosed antibody from the endosome back to the bloodstream (Raghavan et al., 1996, Annu Rev Cell Dev Biol 12:181-220; Ghetie et al., 2000, Annu Rev Immunol 18:739-766, both entirely incorporated by reference). This process, coupled with preclusion of kidney filtration due to the large size of the full-length molecule, results in favorable antibody serum half-lives ranging from one to three weeks. Binding of Fc to FcRn also plays a key role in antibody transport. The binding site on Fc for FcRn is also the site at which the bacterial proteins A and G bind. The tight binding by these proteins is typically exploited as a means to purify antibodies by employing protein A or protein G affinity chromatography during protein purification. Thus the fidelity of this region on Fc is important for both the clinical properties of antibodies and their purification. Available structures of the rat Fc/FcRn complex (Burmeister et al., 1994, Nature, 372:379-383; Martin et al., 2001, Mol Cell 7:867-877, both entirely incorporated by reference), and of the complexes of Fc with proteins A and G (Deisenhofer, 1981, Biochemistry 20:2361-2370; Sauer-Eriksson et al., 1995, Structure 3:265-278; Tashiro et al., 1995, Curr Opin Struct Biol 5:471-481, all entirely incorporated by reference), provide insight into the interaction of Fc with these proteins. The FcRn receptor is also responsible for the transfer of IgG to the neo-natal gut and to the lumen of the intestinal epithelia in adults (Ghetie and Ward, Annu. Rev. Immunol., 2000, 18:739-766; Yoshida et al., Immunity, 2004, 20(6):769-783, both entirely incorporated by reference).

Studies of rat and human Fcγ domains have demonstrated the importance of some Fc residues to the binding of FcRn. The rat and human sequences have about 64% sequence identity in the Fc regions (residues 237-443 in the numbering of Kabat et al.). See FIGS. 3, 4, and 5 for the rat/human alignments of Fc, FcRn heavy chain, and FcRn light chain (beta-2-microglobulin). A model of the human Fc/FcRn complex has been built from the existing structure of the rat Fc/FcRn complex (Martin et al., 2001, Mol Cell 7:867-877, entirely incorporated by reference). The rat and human sequences share some residues that are critical for FcRn binding, such as H310 and H435 (Medesan et al., 1997 J. Immunol. 158(5): 221-7; Shields et al., 2001, J. Biol. Chem. 276(9):6591-6604, both entirely incorporated by reference). In many positions, however, the human and rat proteins have different amino acids, giving the residues in the human sequence different environments, and possibly a different identities, than in the rat sequence. This variability limits the ability to transfer characteristics from one homolog to the other homolog.

In the murine Fcγ, random mutation and phage display selection at the sites, T252, T254, and T256 lead to a triple mutant, T252L/T254S/T256F, that has a 3.5-fold increase in FcRn affinity and a 1.5-fold increase in serum half-life (Ghetie et al., 1997, Nat. Biotech. 15(7): 637-640, entirely incorporated by reference).

The crystal structures of the rat Fc/FcRn complex identified important Fc residues for FcRn binding (Burmeister et al. Nature. 372:379-383 (1994); Martin et al. Molecular Cell. 7:867-877 (2001), both entirely incorporated by reference). The original Fc/FcRn complex structure was solved in 1994 to a resolution of 6 Å (Table 2a, Burmeister et al. Nature. 372:379-383 (1994), entirely incorporated by reference). The higher resolution structure, solved in 2001 by Marin et al, showed a more detailed view of the side chains positions (Martin et al. Molecular Cell. 7:867-877 (2001), entirely incorporated by reference). This crystal structure of rat Fc bound to rat FcRn was solved using an Fc dimer with one monomer containing the mutations T252G/I253G/T254G/H310E/H433E/H435E, which disrupt FcRn binding, and one monomer containing a wild-type Fc monomer.

Mutational studies in human Fcγ have been done on some of the residues that are important for binding to FcRn and have demonstrated have demonstrated an increased serum half-life. In human Fcγ1, Hinton et al. mutated three residues individually to the other 19 common amino acids. Hinton et al., found that some point mutants a double mutant increased the FcRn binding affinity (Hinton et al., 2004, J. Biol. Chem. 279(8): 6213-6216, entirely incorporated by reference). Two mutations had increased half-lives in monkeys. Shields et al. mutated residues, almost exclusively to Ala, and studied their binding to FcRn and the FcγR's (Shields et al., 2001, J. Biol. Chem., 276(9):6591-6604, entirely incorporated by reference).

Dall'Acqua et al. used phage display to select for Fc mutations that bound FcRn with increased affinity (Dall'Acqua et al. 2002, J. Immunol. 169:5171-5180, entirely incorporated by reference). The DNA sequences selected for were primarily double and triple mutants. The reference expressed the proteins encoded by many of their selected sequences and found some that bound to FcRn more tightly than the wild-type Fc.

The administration of antibodies and Fc fusion proteins as therapeutics requires injections with a prescribed frequency relating to the clearance and half-life characteristics of the protein. Longer in vivo half-lives allow more seldom injections or lower dosing, which is clearly advantageous. Although the past mutations in the Fc domain have lead to some proteins with increased FcRn binding affinity and in vivo half-lives, these mutations have not identified the optimal mutations and enhanced in vivo half-life.

One feature of the Fc region is the conserved N-linked glycosylation that occurs at N297, shown in FIG. 1. This carbohydrate, or oligosaccharide as it is sometimes referred, plays a critical structural and functional role for the antibody, and is one of the principle reasons that antibodies must be produced using mammalian expression systems. Umaña et al., 1999, Nat Biotechnol 17:176-180; Davies et al., 2001, Biotechnol Bioeng 74:288-294; Mimura et al., 2001, J Biol Chem 276:45539-45547.; Radaev et al., 2001, J Biol Chem 276:16478-16483; Shields et al., 2001, J Biol Chem 276: 6591-6604; Shields et al., 2002, J Biol Chem 277:26733-26740; Simmons et al., 2002, J Immunol Methods 263:133-147; Radaev et al., 2001, J Biol Chem 276:16469-16477; and Krapp et al., 2003, J Mol Biol 325:979-989, all entirely incorporated by reference).

Antibodies have been developed for therapeutic use. Representative publications related to such therapies include Chamow et al., 1996, Trends Biotechnol 14:52-60; Ashkenazi et al., 1997, Curr Opin Immunol 9:195-200, Cragg et al., 1999, Curr Opin Immunol 11:541-547; Glennie et al., 2000, Immunol Today 21:403-410, McLaughlin et al., 1998, J Clin Oncol 16:2825-2833, and Cobleigh et al., 1999, J Clin Oncol 17:2639-2648, all entirely incorporated by reference. Currently for anticancer therapy, any small improvement in mortality rate defines success. Certain IgG variants disclosed herein enhance the capacity of antibodies to limit further growth or destroy at least partially, targeted cancer cells.

Anti-tumor potency of antibodies is via enhancement of their ability to mediate cytotoxic effector functions such as ADCC, ADCP, and CDC. Examples include Clynes et al., 1998, Proc Natl Acad Sci USA 95:652-656; Clynes et al., 2000, Nat Med 6:443-446 and Cartron et al., 2002, Blood 99:754-758, both entirely incorporated by reference.

Human IgG1 is the most commonly used antibody for therapeutic purposes, and the majority of engineering studies have been constructed in this context. The different isotypes of the IgG class however, including IgG1, IgG2, IgG3, and IgG4, have unique physical, biological, and clinical properties. There is a need in the art to design improved IgG1, IgG2, IgG3, and IgG4 variants. There is a further need to design such variants to improve binding to FcRn and/or increase in vivo half-life as compared to native IgG polypeptides. The present application meets these and other needs.

SUMMARY OF THE INVENTION

The present invention discloses the generation of novel variants of Fc domains, including those found in antibodies, Fc fusions, and immuno-adhesions, which have an increased binding to the FcRn receptor and longer serum retention in vivo. An additional aspect of the invention is the increase in FcRn binding over wild type specifically at lower pH, about pH 6.0, to facilitate Fc/FcRn binding in the endosome. An additional aspect of the present invention is the preferential binding of the designed variants at about pH 6 compared to their binding at about pH 7.4 to facilitate the re-release of Fc into blood following cellular recycling.

A further aspect of the present invention relates to the design of Fc variants with decreased binding to FcRn and decreased in vivo half-lives. Such proteins comprising mutations to reduce FcRn affinity and/or the in vivo half-lives are useful in many therapies and diagnostics, including the delivery and monitoring of radiotherapeutics wherein, ideally, the half-life of the radiolabel is about equal to the in vivo half-life of its protein conjugate.

A further aspect of the invention relates to the alteration of the Fc domain binding to the FcR's, e.g. in humans, FcgRI, FcgRIIa, FcgRIIb, FcgRIIIa. These receptors are responsible for inducing the various effector functions of antibodies. Therefore, a further aspect of the invention relates to the alteration of the Fc domain effector functions, such as antibody-dependent cell-mediated toxicity (ADCC), complement-dependent cytotoxicity (CDC), and antibody dependent cell-mediated phagocytosis (ADCP).

A further aspect of the invention relates to Fc variants that contained both altered FcRn binding and altered Fcg binding to affect both the in vivo half life and the efffector functions of the Fc-comprising protein. For example, these variants may have increased half-life in vivo as well as improved ADCC. The variants, for example, may have increased half-life and decreased CDC.

In a further aspect, the invention provides recombinant nucleic acids encoding the variant Fc proteins, expression vectors, and host cells.

In an additional aspect, the invention provides methods of producing a variant Fc-comprising protein comprising culturing the host cells of the invention under conditions suitable for expression of the protein.

In a further aspect, the invention provides pharmaceutical compositions comprising a variant Fc protein of the invention and a pharmaceutical carrier.

In a further aspect, the invention provides methods for treating disorders comprising administering a protein comprising a variant Fc of the invention to a patient.

In an additional aspect, the invention provides an Fc variant region of a parent Fc polypeptide comprising at least one modification in the Fc region of said parent polypeptide, wherein said variant protein exhibits altered binding to FcRn as compared to the parent polypeptide, and wherein said Fc variant comprises at least one modification selected from the group consisting of: 246H, 246S, 247D, 247T, 248H, 248P, 248Q, 248R, 248Y, 249T, 249W, 251D, 251E, 251H, 251I, 251K, 251M, 251N, 251T, 251V, 251Y, 252F, 252L, 253L, 253T, 253V, 254H, 254L, 254N, 254T, 254V, A254N, 255E, 255F, 255H, 255K, 255S, 255V, 256E, 256H, 256V, 257A, 257C, 257D, 257E, 257F, 257G, 257H, 257I, 257K, 257L, 257M, 257N, 257Q, 257R, 257S, 257T, 257V, 257W, 257Y, 258R, 258V, 279A, 279C, 279D, 279F, 279G, 279H, 279I, 279K, 279L, 279M, 279N, 279P, 279Q, 279R, 279S, 279T, 279W, 279Y, 280E, 280H, A281A, A281D, A281S, A281T, 282D, 282F, 282H, 282I, 282T, 283F, 283I, 283L, 283Y, 284H, 284K, 284P, 284Q, 284R, 284S, 284Y, 285S, 285V, 286#, 286L, 287H, 287S, 287V, 287Y, 288H, 288Q, 288R, 288S, 305H, 305T, 306F, 306H, 306I, 306N, 306T, 306V, 306Y, 307D, 307V, 307Y, 308A, 308C, 308D, 308E, 308F, 308G, 308H, 308I, 308K, 308L, 308M, 308N, 308P, 308Q, 308R, 308S, 308T, 308W, 308Y, 309F, 309H, 309I, 309N, 309P, 309Q, 309V, 309Y, 310K, 310N, 310T, 311H, 311L, 311S, 311T, 311V, 311W, 312H, 313Y, 315E, 315G, 315H, 315Q, 315S, 315T, 317H, 317S, 339P, 340P, 341S, 374H, 374S, 376H, 376L, 378H, 378N, 380T, 380Y, 382H, 383H, 385A, 385C, 385D, 385E, 385F, 385H, 385I, 385K, 385L, 385M, 385N, 385P, 385O, 385R, 385S, 385T, 385V, 385W, 385Y, 386E, 386H, 386K, 387#, 387A, 387H, 387K, 387Q, 389E, 389H, 426E, 426H, 426L, 426N, 426R, 426V, 426Y, 427I, 429D, 429F, 429K, 429N, 429O, 429S, 429T, 429Y, 430D, 430H, 430K, 430L, 430Q, 430Y, 431G, 431H, 431I, 431P, 431S, 432F, 432H, 432N, 432S, 432V, 433E, 433N, 433P, 433R, 433S, 434H, 434Q, 434S, 434Y, 435N, 436E, 436F, 436H, 436L, 436Q, 436V, 436W, 437E, 437V, 438E, 438H and 438K, wherein numbering is according to the EU Index and A is an insertion after the identified position and # is a deletion of that identified position.

In a further aspect, the invention provides Fc variants comprising at least one modification selected from the group consisting of: 246H, 246S, 247D, 247T, 248H, 248P, 248Q, 248R, 248Y, 249T, 249W, 251D, 251E, 251H, 251I, 251K, 251M, 251N, 251T, 251V, 251Y, 252L, 253L, 253T, 253V, 254H, 254L, 254N, 254V, ^254N, 255E, 255F, 255H, 255K, 255V, 256H, 256V, 257A, 257C, 257D, 257E, 257F, 257G, 257H, 257I, 257K, 257L, 257M, 257N, 257Q, 257R, 257S, 257T, 257V, 257W, 257Y, 258R, 258V, 279A, 279C, 279F, 279I, 279P, 279S, 279T, 279W, 279Y, ^281A, ^281D, ^281S, ^281T, 282F, 282I, 282T, 283F, 283I, 283L, 283Y, 284P, 285V, 286#, 286L, 287V, 288Q, 288S, 305T, 306F, 306H, 306I, 306N, 306T, 306V, 306Y, 307V, 308C, 308F, 308G, 308L, 308M, 308N, 308P, 308Q, 308S, 308W, 308Y, 309F, 309N, 309Q, 309V, 309Y, 310T, 311L, 311T, 311V, 311W, 313Y, 315G, 315O, 315S, 315T, 339P, 340P, 341S, 374H, 374S, 376L, 378H, 378N, 380T, 380Y, 382H, 383Q, 384E, 384G, 384H, 385A, 385C, 385F, 385I, 385L, 385M, 385N, 385P, 385Q, 385S, 385T, 385V, 385W, 385Y, 386E, 386H, 386K, 387#, 387A, 387H, 387K, 387Q, 389H, 426L, 426N, 426V, 426Y, 427I, 429D, 429F, 429K, 429N, 429Q, 429S, 429T, 429Y, 430L, 431G, 431I, 431P, 431S, 432F, 432H, 432V, 433E, 433N, 433P, 433S, 434H, 434Q, 434S, 435N, 436F, 436L, 436V, 436W, 437E, and 437V.

BRIEF DESCRIPTION OF THE DRAWINGS

FIG. 3. Example human and rodent IgG sequences used in the present invention with the EU numbering as in Kabat.

FIG. 4. Example human and rodent FcRn heavy chain sequences used in the present invention.

FIG. 5. Example human and rodent beta-2-microglobulin sequences used in the present invention.

FIG. 8. Variants of the present invention.

FIG. 9. Variants of the present invention.

FIG. 10. Variants of the present invention.

FIG. 13. Summary of FcRn binding properties of the Fc variants. The columns from right to left show the FcRn binding modifications, the immunoglobulin used, other modifications, the relative FcRn affinity by AlphaScreen™ competition assays compared to wild type (median value), the number of assays performed, and a reference number of the protein. Relative FcRn affinity numbers greater than 1.0 demonstrate increased binding over wild type.

FIG. 14. FcRn binding data of Fc variants of the present invention. The Fc variants are in alemtuzumab or trastuzumab. The fold-increased binding compared to wild type are shown.

FIG. 16. Surface plasmon resonance experiments of wild-type antibody and variants of the present invention. The traces shown are the association and dissociation of the Fc variant antibody to FcRn at pH6.0.

DETAILED DESCRIPTION OF THE INVENTION

The present invention discloses the generation of novel variants of Fc domains, including those found in antibodies, Fc fusions, and immuno-adhesions, which have an increased binding to the FcRn receptor. As noted herein, binding to RcRn results in longer serum retention in vivo.

Figure 6:
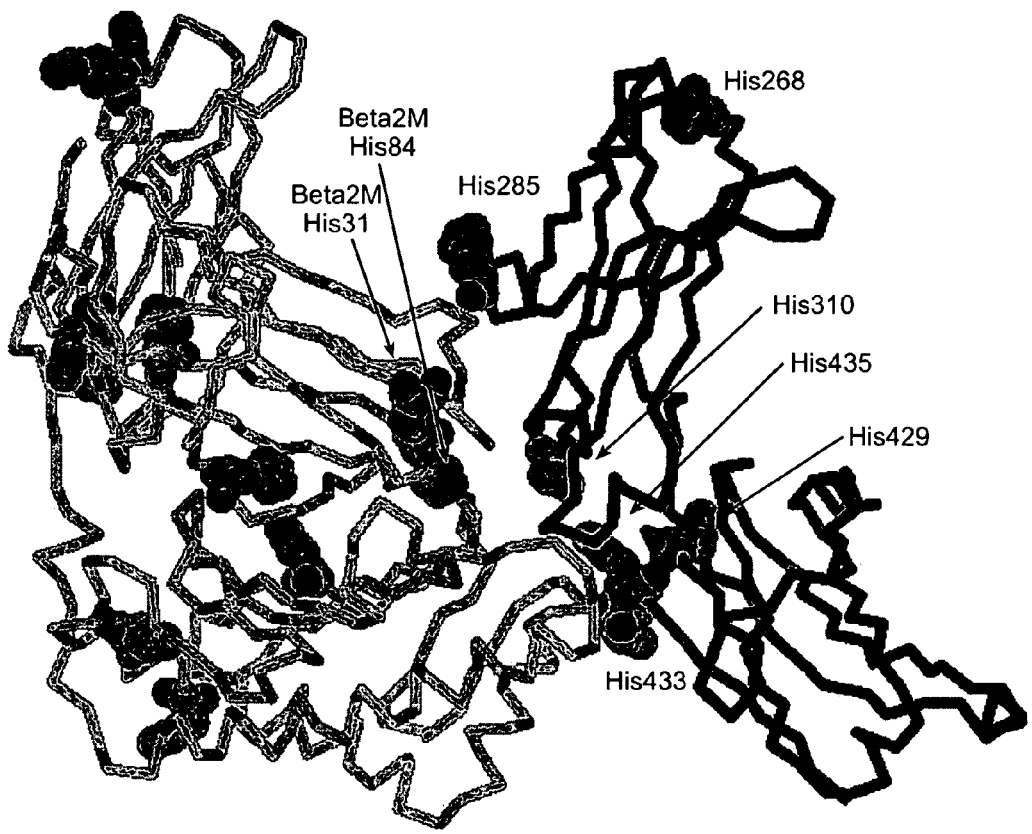
FIG. 6. A human Fc/FcRn complex model created from the rat structures (Burmeister et al., 1994, Nature, 372:379-383; Martin et al., 2001, Mol Cell 7:867-877, both entirely incorporated by reference). Some histidine residues are shown in space-filling atoms on the FcRn chains (light grey) and Fc polypeptide (dark grey).

In order to increase the retention of the Fc proteins in vivo, the increase in binding affinity must be at around pH 6 without a concomitant increase in affinity at around pH 7.4. Although still under examination, Fc regions are believed to have a longer half-lives in vivo, because binding to FcRn at pH 6 in an endosome sequesters the Fc (Ghetie and Ward, 1997 Immunol Today. 18(12): 592-598, entirely incorporated by reference). The endosomal compartment then recycles the Fc to the cell surface. Once the compartment opens to the extracellular space, the higher pH, ~7.4, induces the release of Fc back into the blood. Dall'Acqua et al. showed that Fc mutants with increased FcRn binding at pH 6 and pH 7.4 actually had reduced serum concentrations and the same half life as wild-type Fc (Dall'Acqua et al. 2002, J. Immunol. 169:5171-5180, entirely incorporated by reference). The increased affinity of Fc for FcRn at pH 7.4 is thought to forbid the release of the Fc back into the blood. Therefore, the Fc mutations that will increase Fc's half-life in vivo will ideally increase FcRn binding at the lower pH while still allowing release of Fc at higher pH. The amino acid histidine changes its charge state in the pH range of 6.0 to 7.4. Therefore, it is not surprising to find His residues at important positions in the Fc/FcRn complex (FIG. 6.)

An additional aspect of the invention is the increase in FcRn binding over wild type specifically at lower pH, about pH 6.0, to facilitate Fc/FcRn binding in the endosome. Also disclosed are Fc variants with altered FcRn binding and altered binding to another class of Fc receptors, the FcγR's, as differential binding to FcγRs, particularly increased binding to FcγRIIIb and decreased binding to FcγRIIb has been shown to result in increased efficacy.

DEFINITIONS

In order that the application may be more completely understood, several definitions are set forth below. Such definitions are meant to encompass grammatical equivalents.

By "ADCC" or "antibody dependent cell-mediated cytotoxicity" as used herein is meant the cell-mediated reaction wherein nonspecific cytotoxic cells that express FcγRs recognize bound antibody on a target cell and subsequently cause lysis of the target cell.

By "ADCP" or antibody dependent cell-mediated phagocytosis as used herein is meant the cell-mediated reaction wherein nonspecific cytotoxic cells that express FcγRs recognize bound antibody on a target cell and subsequently cause phagocytosis of the target cell.

By "amino acid modification" herein is meant an amino acid substitution, insertion, and/or deletion in a polypeptide sequence.

By "amino acid substitution" or "substitution" herein is meant the replacement of an amino acid at a particular position in a parent polypeptide sequence with another amino acid. For example, the substitution E272Y refers to a variant polypeptide, in this case an Fc variant, in which the glutamic acid at position 272 is replaced with tyrosine.

By "amino acid insertion" or "insertion" as used herein is meant the addition of an amino acid at a particular position in a parent polypeptide sequence. For example, –233E or ^233E designates an insertion of glutamic acid after position 233 and before position 234. Additionally,—233ADE or A233ADE designates an insertion of AlaAspGlu after position 233 and before position 234.

By "amino acid deletion" or "deletion" as used herein is meant the removal of an amino acid at a particular position in a parent polypeptide sequence. For example, E233- or E233# designates a deletion of glutamic acid at position 233. Additionally, EDA233- or EDA233# designates a deletion of the sequence GluAspAla that begins at position 233.

By "variant protein" or "protein variant", or "variant" as used herein is meant a protein that differs from that of a parent protein by virtue of at least one amino acid modification. Protein variant may refer to the protein itself, a composition comprising the protein, or the amino sequence that encodes it. Preferably, the protein variant has at least one amino acid modification compared to the parent protein, e.g. from about one to about ten amino acid modifications, and preferably from about one to about five amino acid modifications compared to the parent. The protein variant sequence herein will preferably possess at least about 80% homology with a parent protein sequence, and most preferably at least about 90% homology, more preferably at least about 95% homology. Variant protein can refer to the variant protein itself, compositions comprising the protein variant, or the amino acid sequence that encodes it. Accordingly, by "antibody variant" or "variant antibody" as used herein is meant an antibody that differs from a parent antibody by virtue of at least one amino acid modification, "IgG variant" or "variant IgG" as used herein is meant an antibody that differs from a parent IgG by virtue of at least one amino acid modification, and "immunoglobulin variant" or "variant immunoglobulin" as used herein is meant an immunoglobulin sequence that differs from that of a parent immunoglobulin sequence by virtue of at least one amino acid modification. Variants may comprise non-natural amino acids. Examples include U.S. Pat. No. 6,586,207; WO 98/48032; WO 03/073238; US2004-0214988A1; WO 05/35727A2; WO 05/74524A2; J. W. Chin et al., (2002), Journal of the American Chemical Society 124:9026-9027; J. W. Chin, & P. G. Schultz, (2002), ChemBioChem 11:1135-1137; J. W. Chin, et al., (2002), PICAS United States of America 99:11020-11024; and, L. Wang, & P. G. Schultz, (2002), Chem. 1-10, all entirely incorporated by reference.

As used herein, "protein" herein is meant at least two covalently attached amino acids, which includes proteins, polypeptides, oligopeptides and peptides. The peptidyl group may comprise naturally occurring amino acids and peptide bonds, or synthetic peptidomimetic structures, i.e. "analogs", such as peptoids (see Simon et al., PNAS USA 89(20):9367 (1992), entirely incorporated by reference). The amino acids may either be naturally occurring or non-naturally occurring; as will be appreciated by those in the art. For example, homophenylalanine, citrulline, and noreleucine are considered amino acids for the purposes of the invention, and both D- and L- (R or S) configured amino acids may be utilized. The variants of the present invention may comprise modifications that include the use of unnatural amino acids incorporated using, for example, the technologies developed by Schultz and colleagues, including but not limited to methods described by Cropp & Shultz, 2004, Trends Genet. 20(12): 625-30, Anderson et al., 2004, Proc Natl Acad Sci USA 101(2):7566-71, Zhang et al., 2003, 303(5656):371-3, and Chin et al., 2003, Science 301(5635):964-7, all entirely incorporated by reference. In addition, polypeptides may include synthetic derivatization of one or more side chains or termini, glycosylation, PEGylation, circular permutation, cyclization, linkers to other molecules, fusion to proteins or protein domains, and addition of peptide tags or labels.

By "residue" as used herein is meant a position in a protein and its associated amino acid identity. For example, Asparagine 297 (also referred to as Asn297, also referred to as N297) is a residue in the human antibody IgG1.

By "Fab" or "Fab region" as used herein is meant the polypeptides that comprises the VH, CH1, VL, and CL immunoglobulin domains. Fab may refer to this region in isolation, or this region in the context of a full length antibody or antibody fragment.

By "IgG subclass modification" as used herein is meant an amino acid modification that converts one amino acid of one IgG isotype to the corresponding amino acid in a different, aligned IgG isotype. For example, because IgG1 comprises a tyrosine and IgG2 a phenylalanine at EU position 296, a F296Y substitution in IgG2 is considered an IgG subclass modification.

By "non-naturally occurring modification" as used herein is meant an amino acid modification that is not isotypic. For example, because none of the IgGs comprise a glutamic acid at position 332, the substitution I332E in IgG1, IgG2, IgG3, or IgG4 is considered a non-naturally occurring modification.

By "amino acid" and "amino acid identity" as used herein is meant one of the 20 naturally occurring amino acids or any non-natural analogues that may be present at a specific, defined position.

By "effector function" as used herein is meant a biochemical event that results from the interaction of an antibody Fc region with an Fc receptor or ligand. Effector functions include but are not limited to ADCC, ADCP, and CDC.

By "effector cell" as used herein is meant a cell of the immune system that expresses one or more Fc receptors and mediates one or more effector functions. Effector cells include but are not limited to monocytes, macrophages, neutrophils, dendritic cells, eosinophils, mast cells, platelets, B cells, large granular lymphocytes, Langerhans' cells, natural killer (NK) cells, and γδT cells, and may be from any organism including but not limited to humans, mice, rats, rabbits, and monkeys.

By "IgG Fc ligand" as used herein is meant a molecule, preferably a polypeptide, from any organism that binds to the Fc region of an IgG antibody to form an Fc/Fc ligand complex. Fc ligands include but are not limited to FcγRs, FcγRs, FcγRs, FcRn, C1q, C3, mannan binding lectin, mannose receptor, staphylococcal protein A, streptococcal protein G, and viral FcγR. Fc ligands also include Fc receptor homologs (FcRH), which are a family of Fc receptors that are homologous to the FcγRs (Davis et al., 2002, *Immunological Reviews* 190:123-136, entirely incorporated by reference). Fc ligands may include undiscovered molecules that bind Fc. Particular IgG Fc ligands are FcRn and Fc gamma receptors. By "Fc ligand" as used herein is meant a molecule, preferably a polypeptide, from any organism that binds to the Fc region of an antibody to form an Fc/Fc ligand complex.

By "Fc gamma receptor" or "FcγR" as used herein is meant any member of the family of proteins that bind the IgG antibody Fc region and is encoded by an FcγR gene. In humans this family includes but is not limited to FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158) and FcγRIIIb (including allotypes FcγRIIIb-NA1 and FcγRIIIb-NA2) (Jefferis et al., 2002, *Immunol Lett* 82:57-65, entirely incorporated by reference), as well as any undiscovered human FcγRs or FcγR isoforms or allotypes. An FcγR may be from any organism, including but not limited to humans, mice, rats, rabbits, and monkeys. Mouse FcγRs include but are not limited to FcγRI (CD64), FcγRII (CD32), FcγRIII (CD16), and FcγRII-2 (CD16-2), as well as any undiscovered mouse FcγRs or FcγR isoforms or allotypes.

By "FcRn" or "neonatal Fc Receptor" as used herein is meant a protein that binds the IgG antibody Fc region and is encoded at least in part by an FcRn gene. The FcRn may be from any organism, including but not limited to humans, mice, rats, rabbits, and monkeys. As is known in the art, the functional FcRn protein comprises two polypeptides, often referred to as the heavy chain and light chain. The light chain is beta-2-microglobulin and the heavy chain is encoded by the FcRn gene. Unless other wise noted herein, FcRn or an FcRn protein refers to the complex of FcRn heavy chain with beta-2-microglobulin. Sequences of particular interest of FcRn are shown in the Figures, particularly the human species.

By "parent polypeptide" as used herein is meant an unmodified polypeptide that is subsequently modified to generate a variant. The parent polypeptide may be a naturally occurring polypeptide, or a variant or engineered version of a naturally occurring polypeptide. Parent polypeptide may refer to the polypeptide itself, compositions that comprise the parent polypeptide, or the amino acid sequence that encodes it. Accordingly, by "parent immunoglobulin" as used herein is meant an unmodified immunoglobulin polypeptide that is modified to generate a variant, and by "parent antibody" as used herein is meant an unmodified antibody that is modified to generate a variant antibody. It should be noted that "parent antibody" includes known commercial, recombinantly produced antibodies as outlined below.

By "position" as used herein is meant a location in the sequence of a protein. Positions may be numbered sequentially, or according to an established format, for example the EU index as in Kabat. For example, position 297 is a position in the human antibody IgG1.

By "target antigen" as used herein is meant the molecule that is bound specifically by the variable region of a given antibody. A target antigen may be a protein, carbohydrate, lipid, or other chemical compound.

By "target cell" as used herein is meant a cell that expresses a target antigen.

By "variable region" as used herein is meant the region of an immunoglobulin that comprises one or more Ig domains substantially encoded by any of the Vκ, Vλ, and/or VH genes that make up the kappa, lambda, and heavy chain immunoglobulin genetic loci respectively.

By "wild type or WT" herein is meant an amino acid sequence or a nucleotide sequence that is found in nature, including allelic variations. A WT protein has an amino acid sequence or a nucleotide sequence that has not been intentionally modified.

The present invention is directed to antibodies that exhibit moduluated binding to FcRn (modulation including increased as well as decreased binding). For example, in some instances, increased binding results in cellular recycling of the antibody and hence increased half-life, for example for therapeutic antibodies. Alternatively, decreased FcRn binding is desirable, for example for diagnostic antibodies or therapeutic antibodies that contain radiolabels. In addition, antibodies exhibiting increased binding to FcRn and altered binding to other Fc receptors, eg. FcγRs, find use in the present invention. Accordingly, the present invention provides antibodies.

Antibodies

The present application is directed to antibodies that include amino acid modifications that modulate binding to FcRn. Of particular interest are antibodies that minimally comprise an Fc region, or functional variant thereof, that display increased binding affinity to FcRn at lowered pH, and do not exhibit substantially altered binding at higher pH.

Traditional antibody structural units typically comprise a tetramer. Each tetramer is typically composed of two identical pairs of polypeptide chains, each pair having one "light" (typically having a molecular weight of about 25 kDa) and one "heavy" chain (typically having a molecular weight of about 50-70 kDa). Human light chains are classified as kappa and lambda light chains. Heavy chains are classified as mu, delta, gamma, alpha, or epsilon, and define the antibody's isotype as IgM, IgD, IgG, IgA, and IgE, respectively. IgG has several subclasses, including, but not limited to IgG1, IgG2, IgG3, and IgG4. IgM has subclasses, including, but not limited to, IgM1 and IgM2. Thus, "isotype" as used herein is meant any of the subclasses of immunoglobulins defined by the chemical and antigenic characteristics of their constant regions. The known human immunoglobulin isotypes are IgG1, IgG2, IgG3, IgG4, IgA1, IgA2, IgM1, IgM2, IgD, and IgE.

The amino-terminal portion of each chain includes a variable region of about 100 to 110 or more amino acids primarily responsible for antigen recognition. In the variable region, three loops are gathered for each of the V domains of the heavy chain and light chain to form an antigen-binding site. Each of the loops is referred to as a complementarity-determining region (hereinafter referred to as a "CDR"), in which the variation in the amino acid sequence is most significant.

The carboxy-terminal portion of each chain defines a constant region primarily responsible for effector function. Kabat et al. collected numerous primary sequences of the variable regions of heavy chains and light chains. Based on the degree of conservation of the sequences, they classified individual primary sequences into the CDR and the framework and made a list thereof (see SEQUENCES OF IMMUNOLOGICAL INTEREST, 5th edition, NIH publication, No. 91-3242, E. A. Kabat et al., entirely incorporated by reference).

In the IgG subclass of immunoglobulins, there are several immunoglobulin domains in the heavy chain. By "immunoglobulin (Ig) domain" herein is meant a region of an immunoglobulin having a distinct tertiary structure. Of interest in the present invention are the heavy chain domains, including, the constant heavy (CH) domains and the hinge domains. In the context of IgG antibodies, the IgG isotypes each have three CH regions. Accordingly, "CH" domains in the context of IgG are as follows: "CH1" refers to positions 118-220 according to the EU index as in Kabat. "CH2" refers to positions 237-340 according to the EU index as in Kabat, and "CH3" refers to positions 341-447 according to the EU index as in Kabat.

Another type of Ig domain of the heavy chain is the hinge region. By "hinge" or "hinge region" or "antibody hinge region" or "immunoglobulin hinge region" herein is meant the flexible polypeptide comprising the amino acids between the first and second constant domains of an antibody. Structurally, the IgG CH1 domain ends at EU position 220, and the IgG CH2 domain begins at residue EU position 237. Thus for IgG the antibody hinge is herein defined to include positions 221 (D221 in IgG1) to 236 (G236 in IgG1), wherein the numbering is according to the EU index as in Kabat. In some embodiments, for example in the context of an Fc region, the lower hinge is included, with the "lower hinge" generally referring to positions 226 or 230.

Figure 1:
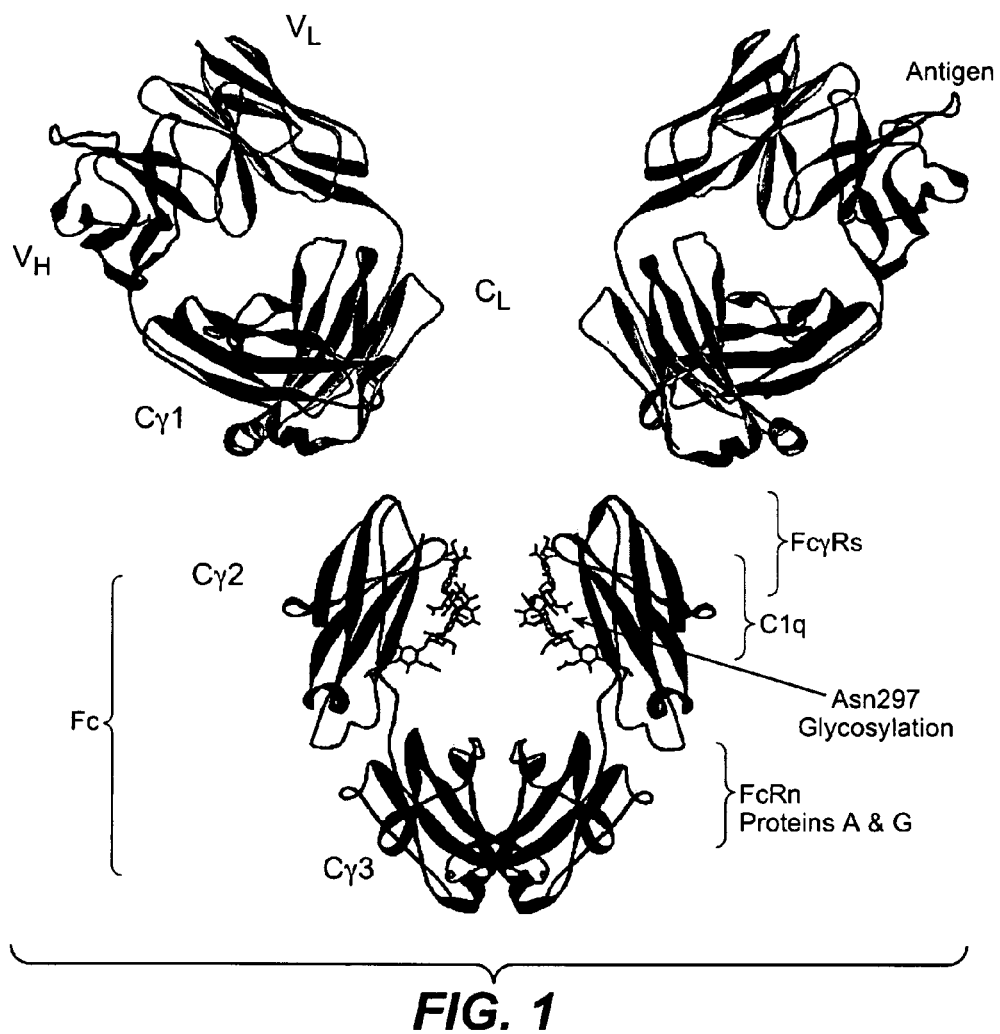
FIG. 1. Antibody structure and function. Shown is a model of a full length human IgG1 antibody, modeled using a humanized Fab structure from pdb accession code 1CE1 (James et al., 1999, *J Mol Biol* 289:293-301, entirely incorporated by reference) and a human IgG1 Fc structure from pdb accession code 1DN2 (DeLano et al., 2000, *Science* 287:1279-1283, entirely incorporated by reference). The flexible hinge that links the Fab and Fc regions is not shown. IgG1 is a homodimer of heterodimers, made up of two light chains and two heavy chains. The Ig domains that comprise the antibody are labeled, and include $V_L$ and $C_L$ for the light chain, and $V_H$, Cgamma1 (Cγ1), Cgamma2 (Cγ2), and Cgamma3 (Cγ3) for the heavy chain. The Fc region is labeled. Binding sites for relevant proteins are labeled, including the antigen binding site in the variable region, and the binding sites for FcγRs, FcRn, C1q, and proteins A and G in the Fc region.

Of particular interest in the present invention are the Fc regions. By "Fc" or "Fc region", as used herein is meant the polypeptide comprising the constant region of an antibody excluding the first constant region immunoglobulin domain and in some cases, part of the hinge. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM, Fc may include the J chain. For IgG, as illustrated in FIG. 1, Fc comprises immunoglobulin domains Cgamma2 and Cgamma3 (Cg2 and Cg3) and the lower hinge region between Cgamma1 (Cg1) and Cgamma2 (Cg2). Although the boundaries of the Fc region may vary, the human IgG heavy chain Fc region is usually defined to include residues C226 or P230 to its carboxyl-terminus, wherein the numbering is according to the EU index as in Kabat. Fc may refer to this region in isolation, or this region in the context of an Fc polypeptide, as described below. By "Fc polypeptide" as used herein is meant a polypeptide that comprises all or part of an Fc region. Fc polypeptides include antibodies, Fc fusions, isolated Fcs, and Fc fragments.

In some embodiments, the antibodies are full length. By "full length antibody" herein is meant the structure that constitutes the natural biological form of an antibody, including variable and constant regions, including one or more modifications as outlined herein.

Alternatively, the antibodies can be a variety of structures, including, but not limited to, antibody fragments, monoclonal antibodies, bispecific antibodies, minibodies, domain antibodies, synthetic antibodies (sometimes referred to herein as "antibody mimetics"), chimeric antibodies, humanized antibodies, antibody fusions (sometimes referred to as "antibody conjugates"), and fragments of each, respectively.

Antibody Fragments

In one embodiment, the antibody is an antibody fragment. Of particular interest are antibodies that comprise Fc regions, Fc fusions, and the constant region of the heavy chain (CH1-hinge-CH2-CH3), again also including constant heavy region fusions.

Specific antibody fragments include, but are not limited to, (i) the Fab fragment consisting of VL, VH, CL and CH1 domains, (ii) the Fd fragment consisting of the VH and CH1 domains, (iii) the Fv fragment consisting of the VL and VH domains of a single antibody; (iv) the dAb fragment (Ward et al., 1989, Nature 341:544-546, entirely incorporated by reference) which consists of a single variable, (v) isolated CDR regions, (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., 1988, Science 242: 423-426, Huston et al., 1988, Proc. Natl. Acad. Sci. U.S.A. 85:5879-5883, entirely incorporated by reference), (viii) bispecific single chain Fv (WO 03/11161, hereby incorporated by reference) and (ix) "diabodies" or "triabodies", multivalent or multispecific fragments constructed by gene fusion (Tomlinson et. al., 2000, Methods Enzymol. 326:461-479; WO94/13804; Holliger et al., 1993, Proc. Natl. Acad. Sci. U.S.A. 90:6444-6448, all entirely incorporated by reference). The antibody fragments may be modified. For example, the molecules may be stabilized by the incorporation of disulphide bridges linking the VH and VL domains (Reiter et al., 1996, Nature Biotech. 14:1239-1245, entirely incorporated by reference).

Chimeric and Humanized Antibodies

In some embodiments, the scaffold components can be a mixture from different species. As such, if the antibody is an antibody, such antibody may be a chimeric antibody and/or a humanized antibody. In general, both "chimeric antibodies" and "humanized antibodies" refer to antibodies that combine regions from more than one species. For example, "chimeric antibodies" traditionally comprise variable region(s) from a mouse (or rat, in some cases) and the constant region(s) from a human. "Humanized antibodies" generally refer to non-human antibodies that have had the variable-domain framework regions swapped for sequences found in human antibodies. Generally, in a humanized antibody, the entire antibody, except the CDRs, is encoded by a polynucleotide of human origin or is identical to such an antibody except within its CDRs. The CDRs, some or all of which are encoded by nucleic acids originating in a non-human organism, are grafted into the beta-sheet framework of a human antibody variable region to create an antibody, the specificity of which is determined by the engrafted CDRs. The creation of such antibodies is described in, e.g., WO 92/11018, Jones, 1986, Nature 321:522-525, Verhoeyen et al., 1988, Science 239: 1534-1536, all entirely incorporated by reference. "Backmutation" of selected acceptor framework residues to the corresponding donor residues is often required to regain affinity that is lost in the initial grafted construct (U.S. Pat. No. 5,530,101; U.S. Pat. No. 5,585,089; U.S. Pat. No. 5,693,761; U.S. Pat. No. 5,693,762; U.S. Pat. No. 6,180,370; U.S. Pat. No. 5,859,205; U.S. Pat. No. 5,821,337; U.S. Pat. No. 6,054,297; U.S. Pat. No. 6,407,213, all entirely incorporated by reference). The humanized antibody optimally also will comprise at least a portion of an immunoglobulin constant region, typically that of a human immunoglobulin, and thus will typically comprise a human Fc region. Humanized antibodies can also be generated using mice with a genetically engineered immune system. Roque et al., 2004, Biotechnol. Prog. 20:639-654, entirely incorporated by reference. A variety of techniques and methods for humanizing and reshaping non-human antibodies are well known in the art (See Tsurushita & Vasquez, 2004, Humanization of Monoclonal Antibodies, Molecular Biology of B Cells, 533-545, Elsevier Science (USA), and references cited therein, all entirely incorporated by reference). Humanization methods include but are not limited to methods described in Jones et al., 1986, Nature 321:522-525; Riechmann et al., 1988; Nature 332:323-329; Verhoeyen et al., 1988, Science, 239:1534-1536; Queen et al., 1989, Proc Natl Acad Sci, USA 86:10029-33; He et al., 1998, J. Immunol. 160: 1029-1035; Carter et al., 1992, Proc Natl Acad Sci USA 89:4285-9, Presta et al., 1997, Cancer Res. 57(20):4593-9; Gorman et al., 1991, Proc. Natl. Acad. Sci. USA 88:4181-4185; O'Connor et al., 1998, Protein Eng 11:321-8, all entirely incorporated by reference. Humanization or other methods of reducing the immunogenicity of nonhuman antibody variable regions may include resurfacing methods, as described for example in Roguska et al., 1994, Proc. Natl. Acad. Sci. USA 91:969-973, entirely incorporated by reference. In one embodiment, the parent antibody has been affinity matured, as is known in the art. Structure-based methods may be employed for humanization and affinity maturation, for example as described in U.S. Ser. No. 11/004,590. Selection based methods may be employed to humanize and/or affinity mature antibody variable regions, including but not limited to methods described in Wu et al., 1999, J. Mol. Biol. 294:151-162; Baca et al., 1997, J. Biol. Chem. 272(16):10678-10684; Rosok et al., 1996, J. Biol. Chem. 271(37): 22611-22618; Rader et al., 1998, Proc. Natl. Acad. Sci. USA 95: 8910-8915; Krauss et al., 2003, Protein Engineering 16(10):753-759, all entirely incorporated by reference. Other humanization methods may involve the grafting of only parts of the CDRs, including but not limited to methods described in U.S. Ser. No. 09/810,510; Tan et al., 2002, J. Immunol. 169:1119-1125; De Pascalis et al., 2002, J. Immunol. 169:3076-3084, all entirely incorporated by reference.

Bispecific Antibodies

In one embodiment, the antibodies of the invention multispecific antibody, and notably a bispecific antibody, also sometimes referred to as "diabodies". These are antibodies that bind to two (or more) different antigens. Diabodies can be manufactured in a variety of ways known in the art (Holliger and Winter, 1993, Current Opinion Biotechnol. 4:446-449, entirely incorporated by reference), e.g., prepared chemically or from hybrid hybridomas.

Minibodies

In one embodiment, the antibody is a minibody. Minibodies are minimized antibody-like proteins comprising a scFv joined to a CH3 domain. Hu et al., 1996, Cancer Res. 56:3055-3061, entirely incorporated by reference. In some cases, the scFv can be joined to the Fc region, and may include some or all of the hinge region.

Human Antibodies

In one embodiment, the antibody is a fully human antibody with at least one modification as outlined herein. "Fully human antibody" or "complete human antibody" refers to a human antibody having the gene sequence of an antibody derived from a human chromosome with the modifications outlined herein.

Antibody Fusions

In one embodiment, the antibodies of the invention are antibody fusion proteins (sometimes referred to herein as an "antibody conjugate"). One type of antibody fusions comprises Fc fusions, which join the Fc region with a conjugate partner. By "Fc fusion" as used herein is meant a protein wherein one or more polypeptides is operably linked to an Fc region. Fc fusion is herein meant to be synonymous with the terms "immunoadhesin", "Ig fusion", "Ig chimera", and "receptor globulin" (sometimes with dashes) as used in the prior art (Chamow et al., 1996, Trends Biotechnol 14:52-60; Ashkenazi et al., 1997, Curr Opin Immunol 9:195-200, both entirely incorporated by reference). An Fc fusion combines the Fc region of an immunoglobulin with a fusion partner, which in general can be any protein or small molecule. Virtually any protein or small molecule may be linked to Fc to generate an Fc fusion. Protein fusion partners may include, but are not limited to, the variable region of any antibody, the target-binding region of a receptor, an adhesion molecule, a ligand, an enzyme, a cytokine, a chemokine, or some other protein or protein domain. Small molecule fusion partners may include any therapeutic agent that directs the Fc fusion to a therapeutic target. Such targets may be any molecule, preferably an extracellular receptor, which is implicated in disease. Thus, the IgG variants can be linked to one or more fusion partners. In one alternate embodiment, the IgG variant is conjugated or operably linked to another therapeutic compound. The therapeutic compound may be a cytotoxic agent, a chemotherapeutic agent, a toxin, a radioisotope, a cytokine, or other therapeutically active agent. The IgG may be linked to one of a variety of nonproteinaceous polymers, e.g., polyethylene glycol, polypropylene glycol, polyoxyalkylenes, or copolymers of polyethylene glycol and polypropylene glycol.

In addition to Fc fusions, antibody fusions include the fusion of the constant region of the heavy chain with one or more fusion partners (again including the variable region of any antibody), while other antibody fusions are substantially or completely full length antibodies with fusion partners. In one embodiment, a role of the fusion partner is to mediate target binding, and thus it is functionally analogous to the variable regions of an antibody (and in fact can be). Virtually any protein or small molecule may be linked to Fc to generate an Fc fusion (or antibody fusion). Protein fusion partners may include, but are not limited to, the target-binding region of a receptor, an adhesion molecule, a ligand, an enzyme, a cytokine, a chemokine, or some other protein or protein domain. Small molecule fusion partners may include any therapeutic agent that directs the Fc fusion to a therapeutic target. Such targets may be any molecule, preferably an extracellular receptor, which is implicated in disease.

The conjugate partner can be proteinaceous or non-proteinaceous; the latter generally being generated using functional groups on the antibody and on the conjugate partner. For example linkers are known in the art; for example, homo- or hetero-bifunctional linkers as are well known (see, 1994 Pierce Chemical Company catalog, technical section on cross-linkers, pages 155-200, incorporated herein by reference).

Suitable conjugates include, but are not limited to, labels as described below, drugs and cytotoxic agents including, but not limited to, cytotoxic drugs (e.g., chemotherapeutic agents) or toxins or active fragments of such toxins. Suitable toxins and their corresponding fragments include diptheria A chain, exotoxin A chain, ricin A chain, abrin A chain, curcin, crotin, phenomycin, enomycin and the like. Cytotoxic agents also include radiochemicals made by conjugating radioisotopes to antibodies, or binding of a radionuclide to a chelating agent that has been covalently attached to the antibody. Additional embodiments utilize calicheamicin, auristatins, geldanamycin, maytansine, and duocarmycins and analogs; for the latter, see U.S. 2003/0050331A1, hereby incorporated by reference in its entirety.

Covalent Modifications of Antibodies

Covalent modifications of antibodies are included within the scope of this invention, and are generally, but not always, done post-translationally. For example, several types of covalent modifications of the antibody are introduced into the molecule by reacting specific amino acid residues of the antibody with an organic derivatizing agent that is capable of reacting with selected side chains or the N- or C-terminal residues.

Cysteinyl residues most commonly are reacted with $\alpha$-haloacetates (and corresponding amines), such as chloroacetic acid or chloroacetamide, to give carboxymethyl or carboxyamidomethyl derivatives. Cysteinyl residues may also be derivatized by reaction with bromotrifluoroacetone, $\alpha$-bromo-$\beta$-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole and the like.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using 125I or 131I to prepare labeled proteins for use in radioimmunoassay, the chloramine T method described above being suitable.

Carboxyl side groups (aspartyl or glutamyl) are selectively modified by reaction with carbodiimides (R'—N=C=N—R'), where R and R' are optionally different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking antibodies to a water-insoluble support matrix or surface for use in a variety of methods, in addition to methods described below. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440, all entirely incorporated by reference, are employed for protein immobilization.

Glutaminyl and asparaginyl residues are frequently deamidated to the corresponding glutamyl and aspartyl residues, respectively. Alternatively, these residues are deamidated under mildly acidic conditions. Either form of these residues falls within the scope of this invention. Other modifications include hydroxylation of proline and lysine, phosphorylation of hydroxyl groups of seryl or threonyl residues, methylation of the $\alpha$-amino groups of lysine, arginine, and histidine side chains (T. E. Creighton, Proteins: Structure and Molecular Properties, W.H. Freeman & Co., San Francisco, pp. 79-86 [1983], entirely incorporated by reference), acetylation of the N-terminal amine, and amidation of any C-terminal carboxyl group.

Glycosylation

Another type of covalent modification is glycosylation. In another embodiment, the IgG variants disclosed herein can be modified to include one or more engineered glycoforms. By "engineered glycoform" as used herein is meant a carbohydrate composition that is covalently attached to an IgG, wherein said carbohydrate composition differs chemically from that of a parent IgG. Engineered glycoforms may be useful for a variety of purposes, including but not limited to enhancing or reducing effector function. Engineered glycoforms may be generated by a variety of methods known in the art (Umaña et al., 1999, Nat Biotechnol 17:176-180; Davies et al., 2001, Biotechnol Bioeng 74:288-294; Shields et al., 2002, J Biol Chem 277:26733-26740; Shinkawa et al., 2003, J Biol Chem 278:3466-3473; U.S. Pat. No. 6,602,684; U.S. Ser. No. 10/277,370; U.S. Ser. No. 10/113,929; PCT WO 00/61739A1; PCT WO 01/29246A1; PCT WO 02/31140A1; PCT WO 02/30954A1, all entirely incorporated by reference; (Potelligent™ technology [Biowa, Inc., Princeton, N.J.]; GlycoMAb® glycosylation engineering technology [Glycart Biotechnology AG, Zürich, Switzerland]). Many of these techniques are based on controlling the level of fucosylated and/or bisecting oligosaccharides that are covalently attached to the Fc region, for example by expressing an IgG in various organisms or cell lines, engineered or otherwise (for example Lec-13 CHO cells or rat hybridoma YB2/0 cells), by regulating enzymes involved in the glycosylation pathway (for example FUT8 [1,6-fucosyltransferase] and/or $\beta$1-4-N-acetylglucosaminyltransferase III [GnTIII]), or by modifying carbohydrate(s) after the IgG has been expressed. Engineered glycoform typically refers to the different carbohydrate or oligosaccharide; thus an IgG variant, for example an antibody or Fc fusion, can include an engineered glycoform. Alternatively, engineered glycoform may refer to the IgG variant that comprises the different carbohydrate or oligosaccharide. As is known in the art, glycosylation patterns can depend on both the sequence of the protein (e.g., the presence or absence of particular glycosylation amino acid residues, discussed below), or the host cell or organism in which the protein is produced. Particular expression systems are discussed below.

Glycosylation of polypeptides is typically either N-linked or O-linked. N-linked refers to the attachment of the carbohydrate moiety to the side chain of an asparagine residue. The tri-peptide sequences asparagine-X-serine and asparagine-X-threonine, where X is any amino acid except proline, are the recognition sequences for enzymatic attachment of the carbohydrate moiety to the asparagine side chain. Thus, the presence of either of these tri-peptide sequences in a polypeptide creates a potential glycosylation site. O-linked glycosylation refers to the attachment of one of the sugars N-acetylgalactosamine, galactose, or xylose, to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tri-peptide sequences (for N-linked glycosylation sites). The alteration may also be made by the addition of, or substitution by, one or more serine or threonine residues to the starting sequence (for O-linked glycosylation sites). For ease, the antibody amino acid sequence is preferably altered through changes at the DNA level, particularly by mutating the DNA encoding the target polypeptide at preselected bases such that codons are generated that will translate into the desired amino acids.

Another means of increasing the number of carbohydrate moieties on the antibody is by chemical or enzymatic coupling of glycosides to the protein. These procedures are advantageous in that they do not require production of the protein in a host cell that has glycosylation capabilities for N- and O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 and in Aplin and Wriston, 1981, CRC Crit. Rev. Biochem., pp. 259-306, both entirely incorporated by reference.

Removal of carbohydrate moieties present on the starting antibody may be accomplished chemically or enzymatically. Chemical deglycosylation requires exposure of the protein to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin et al., 1987, Arch. Biochem. Biophys. 259:52 and by Edge et al., 1981, Anal. Biochem. 118:131, both entirely incorporated by reference. Enzymatic cleavage of carbohydrate moieties on polypeptides can be achieved by the use of a variety of endo- and exo-glycosidases as described by Thotakura et al., 1987, Meth. Enzymol. 138:350, entirely incorporated by reference. Glycosylation at potential glycosylation sites may be prevented by the use of the compound tunicamycin as described by Duskin et al., 1982, J. Biol. Chem. 257:3105, entirely incorporated by reference. Tunicamycin blocks the formation of protein-N-glycoside linkages.

Another type of covalent modification of the antibody comprises linking the antibody to various nonproteinaceous polymers, including, but not limited to, various polyols such as polyethylene glycol, polypropylene glycol or polyoxyalkylenes, in the manner set forth in, for example, 2005-2006 PEG Catalog from Nektar Therapeutics (available at the Nektar website) U.S. Pat. Nos. 4,640,835; 4,496,689; 4,301,144; 4,670,417; 4,791,192 or 4,179,337, all entirely incorporated by reference. In addition, as is known in the art, amino acid substitutions may be made in various positions within the antibody to facilitate the addition of polymers such as PEG. See for example, U.S. Publication No. 2005/0114037A1, entirely incorporated by reference.

Labeled Antibodies

In some embodiments, the covalent modification of the antibodies of the invention comprises the addition of one or more labels. In some cases, these are considered antibody fusions. The term "labelling group" means any detectable label. In some embodiments, the labelling group is coupled to the antibody via spacer arms of various lengths to reduce potential steric hindrance. Various methods for labelling proteins are known in the art and may be used in performing the present invention.

In general, labels fall into a variety of classes, depending on the assay in which they are to be detected: a) isotopic labels, which may be radioactive or heavy isotopes; b) magnetic labels (e.g., magnetic particles); c) redox active moieties; d) optical dyes; enzymatic groups (e.g. horseradish peroxidase, α-galactosidase, luciferase, alkaline phosphatase); e) biotinylated groups; and f) predetermined polypeptide epitopes recognized by a secondary reporter (e.g., leucine zipper pair sequences, binding sites for secondary antibodies, metal binding domains, epitope tags, etc.). In some embodiments, the labelling group is coupled to the antibody via spacer arms of various lengths to reduce potential steric hindrance. Various methods for labelling proteins are known in the art and may be used in performing the present invention.

Specific labels include optical dyes, including, but not limited to, chromophores, phosphors and fluorophores, with the latter being specific in many instances. Fluorophores can be either "small molecule" fluores, or proteinaceous fluores.

By "fluorescent label" is meant any molecule that may be detected via its inherent fluorescent properties. Suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade BlueJ, Texas Red, IAEDANS, EDANS, BODIPY FL, LC Red 640, Cy 5, Cy 5.5, LC Red 705, Oregon green, the Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 660, Alexa Fluor 680), Cascade Blue, Cascade Yellow and R-phycoerythrin (PE) (Molecular Probes, Eugene, Oreg.), FITC, Rhodamine, and Texas Red (Pierce, Rockford, Ill.), Cγ5, Cγ5.5, Cγ7 (Amersham Life Science, Pittsburgh, Pa.). Suitable optical dyes, including fluorophores, are described in Molecular Probes Handbook by Richard P. Haugland, entirely incorporated by reference.

Suitable proteinaceous fluorescent labels also include, but are not limited to, green fluorescent protein, including a *Renilla, Ptilosarcus*, or *Aequorea* species of GFP (Chalfie et al., 1994, Science 263:802-805), EGFP (Clontech Laboratories, Inc., Genbank Accession Number U55762), blue fluorescent protein (BFP, Quantum Biotechnologies, Inc. 1801 de Maisonneuve Blvd. West, 8th Floor, Montreal, Quebec, Canada H3H 1J9; Stauber, 1998, Biotechniques 24:462-471; Heim et al., 1996, Curr. Biol. 6:178-182), enhanced yellow fluorescent protein (EYFP, Clontech Laboratories, Inc.), luciferase (Ichiki et al., 1993, J. Immunol. 150:5408-5417), β galactosidase (Nolan et al., 1988, Proc. Natl. Acad. Sci. U.S.A. 85:2603-2607) and *Renilla* (WO92/15673, WO95/07463, WO98/14605, WO98/26277, WO99/49019, U.S. Pat. Nos. 5,292,658, 5,418,155, 5,683,888, 5,741,668, 5,777,079, 5,804,387, 5,874,304, 5,876,995, 5,925,558). All of the above-cited references in this paragraph are expressly incorporated herein by reference.

IgG Variants

In one embodiment, the invention provides variant IgG proteins. At a minimum, IgG variants comprise an antibody fragment comprising the CH2-CH3 region of the heavy chain. In addition, suitable IgG variants comprise Fc domains (e.g. including the lower hinge region), as well as IgG variants comprising the constant region of the heavy chain (CH1-hinge-CH2-CH3) also being useful in the present invention, all of which can be fused to fusion partners.

An IgG variant includes one or more amino acid modifications relative to a parent IgG polypeptide, in some cases relative to the wild type IgG. The IgG variant can have one or more optimized properties. An IgG variant differs in amino acid sequence from its parent IgG by virtue of at least one amino acid modification. Thus IgG variants have at least one amino acid modification compared to the parent. Alternatively, the IgG variants may have more than one amino acid modification as compared to the parent, for example from about one to fifty amino acid modifications, preferably from about one to ten amino acid modifications, and most preferably from about one to about five amino acid modifications compared to the parent.

Thus the sequences of the IgG variants and those of the parent Fc polypeptide are substantially homologous. For example, the variant IgG variant sequences herein will possess about 80% homology with the parent IgG variant sequence, preferably at least about 90% homology, and most preferably at least about 95% homology. Modifications may be made genetically using molecular biology, or may be made enzymatically or chemically.

Target Antigens for Antibodies

Virtually any antigen may be targeted by the IgG variants, including but not limited to proteins, subunits, domains, motifs, and/or epitopes belonging to the following list of target antigens, which includes both soluble factors such as cytokines and membrane-bound factors, including transmembrane receptors: 17-IA, 4-1BB, 4Dc, 6-keto-PGF1a, 8-iso-PGF2a, 8-oxo-dG, A1 Adenosine Receptor, A33, ACE, ACE-2, Activin, Activin A, Activin AB, Activin B, Activin C, Activin RIA, Activin RIA ALK-2, Activin RIB ALK-4, Activin RIIA, Activin RIIB, ADAM, ADAM10, ADAM12, ADAM15, ADAM17/TACE, ADAM8, ADAM9, ADAMTS, ADAMTS4, ADAMTS5, Addressins, aFGF, ALCAM, ALK, ALK-1, ALK-7, alpha-1-antitrypsin, alpha-V/beta-1 antagonist, ANG, Ang, APAF-1, APE, APJ, APP, APRIL, AR, ARC, ART, Artemin, anti-id, ASPARTIC, Atrial natriuretic factor, av/b3 integrin, AxI, b2M, B7-1, B7-2, B7-H, B-lymphocyte Stimulator (BlyS), BACE, BACE-1, Bad, BAFF, BAFF-R, Bag-1, BAK, Bax, BCA-1, BCAM, Bcl, BCMA, BDNF, b-ECGF, bFGF, BID, Bik, BIM, BLC, BL-CAM, BLK, BMP, BMP-2 BMP-2a, BMP-3 Osteogenin, BMP-4 BMP-2b, BMP-5, BMP-6 Vgr-1, BMP-7 (OP-1), BMP-8 (BMP-8a, OP-2), BMPR, BMPR-IA (ALK-3), BMPR-IB (ALK-6), BRK-2, RPK-1, BMPR-II (BRK-3), BMPs, b-NGF, BOK, Bombesin, Bone-derived neurotrophic factor, BPDE, BPDE-DNA, BTC, complement factor 3 (C3), C3a, C4, C5, C5a, C10, CA125, CAD-8, Calcitonin, cAMP, carcinoembryonic antigen (CEA), carcinoma-associated antigen, Cathepsin A, Cathepsin B, Cathepsin C/DPPI, Cathepsin D, Cathepsin E, Cathepsin H, Cathepsin L, Cathepsin O, Cathepsin S, Cathepsin V, Cathepsin X/Z/P, CBL, CCl, CCK2, CCL, CCL1, CCL11, CCL12, CCL13, CCL14, CCL15, CCL16, CCL17, CCL18, CCL19, CCL2, CCL20, CCL21, CCL22, CCL23, CCL24, CCL25, CCL26, CCL27, CCL28, CCL3, CCL4, CCL5, CCL6, CCL7, CCL8, CCL9/10, CCR, CCR1, CCR10, CCR10, CCR2, CCR3, CCR4, CCR5, CCR6, CCR7, CCR8, CCR9, CD1, CD2, CD3, CD3E, CD4, CD5, CD6, CD7, CD8, CD10, CD11a, CD11b, CD11c, CD13, CD14, CD15, CD16, CD18, CD19, CD20, CD21, CD22, CD23, CD25, CD27L, CD28, CD29, CD30, CD30L, CD32, CD33 (p67 proteins), CD34, CD38, CD40, CD40L, CD44, CD45, CD46, CD49a, CD52, CD54, CD55, CD56, CD61, CD64, CD66e, CD74, CD80 (B7-1), CD89, CD95, CD123, CD137, CD138, CD140a, CD146, CD147, CD148, CD152, CD164, CEACAM5, CFTR, cGMP, CINC, *Clostridium botulinum* toxin, *Clostridium perfringens* toxin, CKb8-1, CLC, CMV, CMV UL, CNTF, CNTN-1, COX, C-Ret, CRG-2, CT-1, CTACK, CTGF, CTLA-4, CX3CL1, CX3CR1, CXCL, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCR, CXCR1, CXCR2, CXCR3, CXCR4, CXCR5, CXCR6, cytokeratin tumor-associated antigen, DAN, DCC, DcR3, DC-SIGN, Decay accelerating factor, des(1-3)-IGF-I (brain IGF-1), Dhh, digoxin, DNAM-1, Dnase, Dpp, DPPIV/CD26, Dtk, ECAD, EDA, EDA-A1, EDA-A2, EDAR, EGF, EGFR (ErbB-1), EMA, EMMPRIN, ENA, endothelin receptor, Enkephalinase, eNOS, Eot, eotaxin1, EpCAM, Ephrin B2/EphB4, EPO, ERCC, E-selectin, ET-1, Factor IIa, Factor VII, Factor VIIIc, Factor IX, fibroblast activation protein (FAP), Fas, FcR1, FEN-1, Ferritin, FGF, FGF-19, FGF-2, FGF3, FGF-8, FGFR, FGFR-3, Fibrin, FL, FLIP, Flt-3, Flt-4, Follicle stimulating hormone, Fractalkine, FZD1, FZD2, FZD3, FZD4, FZD5, FZD6, FZD7, FZD8, FZD9, FZD10, G250, Gas 6, GCP-2, GCSF, GD2, GD3, GDF, GDF-1, GDF-3 (Vgr-2), GDF-5 (BMP-14, CDMP-1), GDF-6 (BMP-13, CDMP-2), GDF-7 (BMP-12, CDMP-3), GDF-8 (Myostatin), GDF-9, GDF-15 (MIC-1), GDNF, GDNF, GFAP, GFRa-1, GFR-alpha1, GFR-alpha2, GFR-alpha3, GITR, Glucagon, Glut 4, glycoprotein IIb/IIIa (GP IIb/IIIa), GM-CSF, gp130, gp72, GRO, Growth hormone releasing factor, Hapten (NP-cap or NIP-cap), HB-EGF, HCC, HCMV gB envelope glycoprotein, HCMV) gH envelope glycoprotein, HCMV UL, Hemopoietic growth factor (HGF), Hep B gp120, heparanase, Her2, Her2/neu (ErbB-2), Her3 (ErbB-3), Her4 (ErbB-4), herpes simplex virus (HSV) gB glycoprotein, HSV gD glycoprotein, HGFA, High molecular weight melanoma-associated antigen (HMW-MM), HIV gp120, HIV IIIB gp120 V3 loop, HLA, HLA-DR, HM1.24, HMFG PEM, HRG, Hrk, human cardiac myosin, human cytomegalovirus (HCMV), human growth hormone (HGH), HVEM, 1-309, IAP, ICAM, ICAM-1, ICAM-3, ICE, ICOS, IFNg, Ig, IgA receptor, IgE, IGF, IGF binding proteins, IGF-1R, IGFBP, IGF-I, IGF-II, IL, IL-1, IL-1R, IL-2, IL-2R, IL-4, IL-4R, IL-5, IL-5R, IL-6, IL-6R, IL-8, IL-9, IL-10, IL-12, IL-13, IL-15, IL-18, IL-18R, IL-23, interferon (INF)-alpha, INF-beta, INF-gamma, Inhibin, iNOS, Insulin A-chain, Insulin B-chain, Insulin-like growth factor 1, integrin alpha2, integrin alpha3, integrin alpha4, integrin alpha4/beta1, integrin alpha4/beta7, integrin alpha5 (alphaV), integrin alpha5/beta1, integrin alpha5/beta3, integrin alpha6, integrin beta1, integrin beta2, interferon gamma, IP-10, I-TAC, JE, Kallikrein 2, Kallikrein 5, Kallikrein 6, Kallikrein 11, Kallikrein 12, Kallikrein 14, Kallikrein 15, Kallikrein L1, Kallikrein L2, Kallikrein L3, Kallikrein L4, KC, KDR, Keratinocyte Growth Factor (KGF), laminin 5, LAMP, LAP, LAP (TGF-1), Latent TGF-1, Latent TGF-1 bp1, LBP, LDGF, LECT2, Lefty, Lewis-Y antigen, Lewis-Y related antigen, LFA-1, LFA-3, Lfo, LIF, LIGHT, lipoproteins, LIX, LKN, Lptn, L-Selectin, LT-a, LT-b, LTB4, LTBP-1, Lung surfactant, Luteinizing hormone, Lymphotoxin Beta Receptor, Mac-1, MAdCAM, MAG, MAP2, MARC, MCAM, MCAM, MCK-2, MCP, M-CSF, MDC, Mer, METALLOPROTEASES, MGDF receptor, MGMT, MHC (HLA-DR), MIF, MIG, MIP, MIP-1-alpha, MK, MMAC1, MMP, MMP-1, MMP-10, MMP-11, MMP-12, MMP-13, MMP-14, MMP-15, MMP-2, MMP-24, MMP-3, MMP-7, MMP-8, MMP-9, MPIF, Mpo, MSK, MSP, mucin (Muc1), MUC18, Muellerian-inhibitin substance, Mug, MuSK, NAIP, NAP, NCAD, N-Cadherin, NCA 90, NCAM, NCAM, Neprilysin, Neurotrophin-3, -4, or -6, Neurturin, Neuronal growth factor (NGF), NGFR, NGF-beta, nNOS, NO, NOS, Npn, NRG-3, NT, NTN, OB, OGG1, OPG, OPN, OSM, OX40L, OX40R, p150, p95, PADPr, Parathyroid hormone, PARC, PARP, PBR, PBSF, PCAD, P-Cadherin, PCNA, PDGF, PDGF, PDK-1, PECAM, PEM, PF4, PGE, PGF, PGI2, PGJ2, PIN, PLA2, placental alkaline phosphatase (PLAP), PIGF, PLP, PP14, Proinsulin, Prorelaxin, Protein C, PS, PSA, PSCA, prostate specific membrane antigen (PSMA), PTEN, PTHrp, Ptk, PTN, R51, RANK, RANKL, RANTES, RANTES, Relaxin A-chain, Relaxin B-chain, renin, respiratory syncytial virus (RSV) F, RSV Fgp, Ret, Rheumatoid factors, RLIP76, RPA2, RSK, S100, SCF/KL, SDF-1, SERINE, Serum albumin, sFRP-3, Shh, SIGIRR, SK-1, SLAM, SLPI, SMAC, SMDF, SMOH, SOD, SPARC, Stat, STEAP, STEAP-II, TACE, TACI, TAG-72 (tumor-associated glycoprotein-72), TARC, TCA-3, T-cell receptors (e.g., T-cell receptor alpha/beta), TdT, TECK, TEM1, TEM5, TEM7, TEM8, TERT, testicular PLAP-like alkaline phosphatase, TfR, TGF, TGF-alpha, TGF-beta, TGF-beta Pan Specific, TGF-beta R1 (ALK-5), TGF-beta RII, TGF-beta RIIb, TGF-beta RIII, TGF-beta1, TGF-beta2, TGF-beta3, TGF-beta4, TGF-beta5, Thrombin, Thymus Ck-1, Thyroid stimulating hormone, Tie, TIMP, TIQ, Tissue Factor, TMEFF2, Tmpo, TMPRSS2, TNF, TNF-alpha, TNF-alpha beta, TNF-beta2, TNFc, TNF-R1, TNF-R11, TNFRSF10A (TRAIL R1 Apo-2, DR4), TNFRSF10B (TRAIL R2 DR5, KILLER, TRICK-2A, TRICK-B), TNFRSF10C (TRAIL R3 DcR1, LIT, TRID), TNFRSF10D (TRAIL R4 DcR2, TRUNDD), TNFRSF11A (RANK ODF R, TRANCE R), TNFRSF11B (OPG OCIF, TR1), TNFRSF12 (TWEAK R FN14), TNFRSF13B (TACI), TNFRSF13C (BAFF R), TNFRSF14 (HVEM ATAR, HveA, LIGHT R, TR2), TNFRSF16 (NGFR p75NTR), TNFRSF17 (BCMA), TNFRSF18 (GITR AITR), TNFRSF19 (TROY TAJ, TRADE), TNFRSF19L (RELT), TNFRSF1A (TNF R1 CD120a, p55-60), TNFRSF18 (TNF RII CD120b, p75-80), TNFRSF26 (TNFRH3), TNFRSF3 (LTbR TNF RIII, TNFC R), TNFRSF4 (OX40 ACT35, TXGP1R), TNFRSF5 (CD40 p50), TNFRSF6 (Fas Apo-1, APT1, CD95), TNFRSF6B (DcR3 M68, TR6), TNFRSF7 (CD27), TNFRSF8 (CD30), TNFRSF9 (4-1BB CD137, ILA), TNFRSF21 (DR6), TNFRSF22 (DcTRAIL R2 TNFRH2), TNFRST23 (DcTRAIL R1 TNFRH1), TNFRSF25 (DR3 Apo-3, LARD, TR-3, TRAMP, WSL-1), TNFSF10 (TRAIL Apo-2 Ligand, TL2), TNFSF11 (TRANCE/RANK Ligand ODF, OPG Ligand), TNFSF12 (TWEAK Apo-3 Ligand, DR3 Ligand), TNFSF13 (APRIL TALL2), TNFSF13B (BAFF BLYS, TALL1, THANK, TNFSF20), TNFSF14 (LIGHT HVEM Ligand, LTg), TNFSF15 (TL1A/VEGI), TNFSF18 (GITR Ligand AITR Ligand, TL6), TNFSF1A (TNF-a Conectin, DIF, TNFSF2), TNFSF1B (TNF-b LTa, TNFSF1), TNFSF3 (LTb TNFC, p33), TNFSF4 (OX40 Ligand gp34, TXGP1), TNFSF5 (CD40 Ligand CD154, gp39, HIGM1, IMD3, TRAP), TNFSF6 (Fas Ligand Apo-1 Ligand, APT1 Ligand), TNFSF7 (CD27 Ligand CD70), TNFSF8 (CD30 Ligand CD153), TNFSF9 (4-1BB Ligand CD137 Ligand), TP-1, t-PA, Tpo, TRAIL, TRAIL R, TRAIL-R1, TRAIL-R2, TRANCE, transferring receptor, TRF, Trk, TROP-2, TSG, TSLP, tumor-associated antigen CA 125, tumor-associated antigen expressing Lewis Y related carbohydrate, TWEAK, TXB2, Ung, uPAR, uPAR-1, Urokinase, VCAM, VCAM-1, VECAD, VE-Cadherin, VE-cadherin-2, VEFGR-1 (fit-1), VEGF, VEGFR, VEGFR-3 (flt-4), VEGI, VIM, Viral antigens, VLA, VLA-1, VLA-4, VNR integrin, von Willebrands factor, WIF-1, WNT1, WNT2, WNT2B/13, WNT3, WNT3A, WNT4, WNT5A, WNT5B, WNT6, WNT7A, WNT7B, WNT8A, WNT8B, WNT9A, WNT9A, WNT9B, WNT10A, WNT10B, WNT11, WNT16, XCL1, XCL2, XCR1, XCR1, XEDAR, XIAP, XPD, and receptors for hormones and growth factors.

One skilled in the art will appreciate that the aforementioned list of targets refers not only to specific proteins and biomolecules, but the biochemical pathway or pathways that comprise them. For example, reference to CTLA-4 as a target antigen implies that the ligands and receptors that make up the T cell co-stimulatory pathway, including CTLA-4, B7-1, B7-2, CD28, and any other undiscovered ligands or receptors that bind these proteins, are also targets. Thus target as used herein refers not only to a specific biomolecule, but the set of proteins that interact with said target and the members of the biochemical pathway to which said target belongs. One skilled in the art will further appreciate that any of the aforementioned target antigens, the ligands or receptors that bind them, or other members of their corresponding biochemical pathway, may be operably linked to the Fc variants of the present invention in order to generate an Fc fusion. Thus for example, an Fc fusion that targets EGFR could be constructed by operably linking an Fc variant to EGF, TGF-b, or any other ligand, discovered or undiscovered, that binds EGFR. Accordingly, an Fc variant of the present invention could be operably linked to EGFR in order to generate an Fc fusion that binds EGF, TGF-b, or any other ligand, discovered or undiscovered, that binds EGFR. Thus virtually any polypeptide, whether a ligand, receptor, or some other protein or protein domain, including but not limited to the aforementioned targets and the proteins that compose their corresponding biochemical pathways, may be operably linked to the Fc variants of the present invention to develop an Fc fusion.

The choice of suitable antigen depends on the desired application. For anti-cancer treatment it is desirable to have a target whose expression is restricted to the cancerous cells. Some targets that have proven especially amenable to antibody therapy are those with signaling functions. Other therapeutic antibodies exert their effects by blocking signaling of the receptor by inhibiting the binding between a receptor and its cognate ligand. Another mechanism of action of therapeutic antibodies is to cause receptor down regulation. Other antibodies do not work by signaling through their target antigen. In some cases, antibodies directed against infectious disease agents are used.

In one embodiment, the Fc variants of the present invention are incorporated into an antibody against a cytokine. Alternatively, the Fc variants are fused or conjugated to a cytokine. By "cytokine" as used herein is meant a generic term for proteins released by one cell population that act on another cell as intercellular mediators. For example, as described in Penichet et al., 2001, J Immunol Methods 248:91-101, expressly incorporated by reference, cytokines may be fused to antibody to provide an array of desirable properties. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; C5a; and other polypeptide factors including LIF and kit ligand (KL). As used herein, the term cytokine includes proteins from natural sources or from recombinant cell culture, and biologically active equivalents of the native sequence cytokines.

Cytokines and soluble targets, such as TNF superfamily members, are preferred targets for use with the variants of the present invention. For example, anti-VEGF, anti-CTLA-4, and anti-TNF antibodies, or fragments thereof, are particularly good antibodies for the use of Fc variants that increase the FcRn binding. Therapeutics against these targets are frequently involved in the treatment of autoimmune diseases and require multiple injections over long time periods. Therefore, longer serum half-lives and less frequent treatments, brought about from the variants of the present invention, are particularly preferred.

A number of antibodies and Fc fusions that are approved for use, in clinical trials, or in development may benefit from the Fc variants of the present invention. These antibodies and Fc fusions are herein referred to as "clinical products and candidates". Thus in a preferred embodiment, the Fc polypeptides of the present invention may find use in a range of clinical products and candidates. For example, a number of antibodies that target CD20 may benefit from the Fc polypeptides of the present invention. For example the Fc polypeptides of the present invention may find use in an antibody that is substantially similar to rituximab (Rituxan®, IDEC/Genentech/Roche) (see for example U.S. Pat. No. 5,736,137), a chimeric anti-CD20 antibody approved to treat Non-Hodgkin's lymphoma; HuMax-CD20, an anti-CD20 currently being developed by Genmab, an anti-CD20 antibody described in U.S. Pat. No. 5,500,362, AME-133 (Applied Molecular Evolution), hA20 (Immunomedics, Inc.), HumaLYM (Intracel), and PRO70769 (PCT/US2003/040426, entitled "Immunoglobulin Variants and Uses Thereof"). A number of antibodies that target members of the family of epidermal growth factor receptors, including EGFR (ErbB-1), Her2/neu (ErbB-2), Her3 (ErbB-3), Her4 (ErbB-4), may benefit from the Fc polypeptides of the present invention. For example the Fc polypeptides of the present invention may find use in an antibody that is substantially similar to trastuzumab (Herceptin®, Genentech) (see for example U.S. Pat. No. 5,677,171), a humanized anti-Her2/neu antibody approved to treat breast cancer; pertuzumab (rhuMab-2C4, Omnitarg™), currently being developed by Genentech; an anti-Her2 antibody described in U.S. Pat. No. 4,753,894; cetuximab (Erbitux®, Imclone) (U.S. Pat. No. 4,943,533; PCT WO 96/40210), a chimeric anti-EGFR antibody in clinical trials for a variety of cancers; ABX-EGF (U.S. Pat. No. 6,235,883), currently being developed by Abgenix-Immunex-Amgen; HuMax-EGFr (U.S. Ser. No. 10/172,317), currently being developed by Genmab; 425, EMD55900, EMD62000, and EMD72000 (Merck KGaA) (U.S. Pat. No. 5,558,864; Murthy et al. 1987, Arch Biochem Biophys. 252(2):549-60; Rodeck et al., 1987, J Cell Biochem. 35(4):315-20; Kettleborough et al., 1991, Protein Eng. 4(7):773-83); ICR62 (Institute of Cancer Research) (PCT WO 95/20045; Modjtahedi et al., 1993, J. Cell Biophys. 1993, 22(1-3):129-46; Modjtahedi et al., 1993, Br J Cancer. 1993, 67(2):247-53; Modjtahedi et al, 1996, Br J Cancer, 73(2):228-35; Modjtahedi et al, 2003, Int J Cancer, 105(2):273-80); TheraCIM hR3 (YM Biosciences, Canada and Centro de Immunologia Molecular, Cuba (U.S. Pat. No. 5,891,996; U.S. Pat. No. 6,506,883; Mateo et al, 1997, Immunotechnology, 3(1):71-81); mAb-806 (Ludwig Institue for Cancer Research, Memorial Sloan-Kettering) (Jungbluth et al. 2003, Proc Natl Acad Sci USA. 100(2):639-44); KSB-102 (KS Biomedix); MR1-1 (IVAX, National Cancer Institute) (PCT WO 0162931A2); and SC100 (Scancell) (PCT WO 01/88138). In another preferred embodiment, the Fc polypeptides of the present invention may find use in alemtuzumab (Campath®, Millenium), a humanized monoclonal antibody currently approved for treatment of B-cell chronic lymphocytic leukemia. The Fc polypeptides of the present invention may find use in a variety of antibodies or Fc fusions that are substantially similar to other clinical products and candidates, including but not limited to muromonab-CD3 (Orthoclone OKT3®), an anti-CD3 antibody developed by Ortho Biotech/Johnson & Johnson, ibritumomab tiuxetan (Zevalin®), an anti-CD20 antibody developed by IDEC/Schering AG, gemtuzumab ozogamicin (Mylotarg®), an anti-CD33 (p67 protein) antibody developed by Celltech/Wyeth, alefacept (Amevive®), an anti-LFA-3 Fc fusion developed by Biogen), abciximab (ReoPro®), developed by Centocor/Lilly, basiliximab (Simulect®), developed by Novartis, palivizumab (Synagis®), developed by Medimmune, infliximab (Remicade®), an anti-TNFalpha antibody developed by Centocor, adalimumab (Humira®), an anti-TNFalpha antibody developed by Abbott, Humicade™, an anti-TNFalpha antibody developed by Celltech, etanercept (Enbrel®), an anti-TNFalpha Fc fusion developed by Immunex/Amgen, ABX-CBL, an anti-CD147 antibody being developed by Abgenix, ABX-IL8, an anti-IL8 antibody being developed by Abgenix, ABX-MA1, an anti-MUC18 antibody being developed by Abgenix, Pemtumomab (R1549, 90Y-muHMFG1), an anti-MUC1 In development by Antisoma, Therex (R1550), an anti-MUC1 antibody being developed by Antisoma, AngioMab (AS1405), being developed by Antisoma, HuBC-1, being developed by Antisoma, Thioplatin (AS1407) being developed by Antisoma, Antegren® (natalizumab), an anti-alpha-4-beta-1 (VLA-4) and alpha-4-beta-7 antibody being developed by Biogen, VLA-1 mAb, an anti-VLA-1 integrin antibody being developed by Biogen, LTBR mAb, an anti-lymphotoxin beta receptor (LTBR) antibody being developed by Biogen, CAT-152, an anti-TGF-β2 antibody being developed by Cambridge Antibody Technology, J695, an anti-IL-12 antibody being developed by Cambridge Antibody Technology and Abbott, CAT-192, an anti-TGFβ1 antibody being developed by Cambridge Antibody Technology and Genzyme, CAT-213, an anti-Eotaxin1 antibody being developed by Cambridge Antibody Technology, LymphoStat-B™ an anti-Blys antibody being developed by Cambridge Antibody Technology and Human Genome Sciences Inc., TRAIL-R1mAb, an anti-TRAIL-R1 antibody being developed by Cambridge Antibody Technology and Human Genome Sciences, Inc., Avastin™ (bevacizumab, rhuMAb-VEGF), an anti-VEGF antibody being developed by Genentech, an anti-HER receptor family antibody being developed by Genentech, Anti-Tissue Factor (ATF), an anti-Tissue Factor antibody being developed by Genentech, Xolair™ (Omalizumab), an anti-IgE antibody being developed by Genentech, Raptiva™ (Efalizumab), an anti-CD11a antibody being developed by Genentech and Xoma, MLN-02 Antibody (formerly LDP-02), being developed by Genentech and Millenium Pharmaceuticals, HuMax CD4, an anti-CD4 antibody being developed by Genmab, HuMax-IL15, an anti-IL15 antibody being developed by Genmab and Amgen, HuMax-Inflam, being developed by Genmab and Medarex, HuMax-Cancer, an anti-Heparanase I antibody being developed by Genmab and Medarex and Oxford GcoSciences, HuMax-Lymphoma, being developed by Genmab and Amgen, HuMax-TAC, being developed by Genmab, IDEC-131, and anti-CD40L antibody being developed by IDEC Pharmaceuticals, IDEC-151 (Clenoliximab), an anti-CD4 antibody being developed by IDEC Pharmaceuticals, IDEC-114, an anti-CD80 antibody being developed by IDEC Pharmaceuticals, IDEC-152, an anti-CD23 being developed by IDEC Pharmaceuticals, anti-macrophage migration factor (MIF) antibodies being developed by IDEC Pharmaceuticals, BEC2, an anti-idiotypic antibody being developed by Imclone, IMC-1C11, an anti-KDR antibody being developed by Imclone, DC101, an anti-flk-1 antibody being developed by Imclone, anti-VE cadherin antibodies being developed by Imclone, CEA-Cide™ (labetuzumab), an anti-carcinoembryonic antigen (CEA) antibody being developed by Immunomedics, LymphoCide™ (Epratuzumab), an anti-CD22 antibody being developed by Immunomedics, AFP-Cide, being developed by Immunomedics, MyelomaCide, being developed by Immunomedics, LkoCide, being developed by Immunomedics, ProstaCide, being developed by Immunomedics, MDX-010, an anti-CTLA4 antibody being developed by Medarex, MDX-060, an anti-CD30 antibody being developed by Medarex, MDX-070 being developed by Medarex, MDX-018 being developed by Medarex, Osidem™ (IDM-1), and anti-Her2 antibody being developed by Medarex and Immuno-Designed Molecules, HuMax™-CD4, an anti-CD4 antibody being developed by Medarex and Genmab, HuMax-IL15, an anti-IL15 antibody being developed by Medarex and Genmab, CNTO 148, an anti-TNFα antibody being developed by Medarex and Centocor/J&J, CNTO 1275, an anti-cytokine antibody being developed by Centocor/J&J, MOR101 and MOR102, anti-intercellular adhesion molecule-1 (ICAM-1) (CD54) antibodies being developed by MorphoSys, MOR201, an anti-fibroblast growth factor receptor 3 (FGFR-3) antibody being developed by MorphoSys, Nuvion® (visilizumab), an anti-CD3 antibody being developed by Protein Design Labs, HuZAF™, an anti-gamma interferon antibody being developed by Protein Design Labs, Anti-α5β1 Integrin, being developed by Protein Design Labs, anti-IL-12, being developed by Protein Design Labs, ING-1, an anti-Ep-CAM antibody being developed by Xoma, and MLN01, an anti-Beta2 integrin antibody being developed by Xoma, all of the above-cited references in this paragraph are expressly incorporated herein by reference.

The Fc polypeptides of the present invention may be incorporated into the aforementioned clinical candidates and products, or into antibodies and Fc fusions that are substantially similar to them. The Fc polypeptides of the present invention may be incorporated into versions of the aforementioned clinical candidates and products that are humanized, affinity matured, engineered, or modified in some other way.

In one embodiment, the Fc polypeptides of the present invention are used for the treatment of autoimmune, inflammatory, or transplant indications. Target antigens and clinical products and candidates that are relevant for such diseases include but are not limited to anti-α4β7 integrin antibodies such as LDP-02, anti-beta2 integrin antibodies such as LDP-01, anti-complement (C5) antibodies such as 5G1.1, anti-CD2 antibodies such as BTI-322, MEDI-507, anti-CD3 antibodies such as OKT3, SMART anti-CD3, anti-CD4 antibodies such as IDEC-151, MDX-CD4, OKT4A, anti-CD11a antibodies, anti-CD14 antibodies such as IC14, anti-CD18 antibodies, anti-CD23 antibodies such as IDEC 152, anti-CD25 antibodies such as Zenapax, anti-CD40L antibodies such as 5c8, Antova, IDEC-131, anti-CD64 antibodies such as MDX-33, anti-CD80 antibodies such as IDEC-114, anti-CD147 antibodies such as ABX-CBL, anti-E-selectin antibodies such as CDP850, anti-gpIIb/IIIa antibodies such as ReoPro/Abcixima, anti-ICAM-3 antibodies such as ICM3, anti-ICE antibodies such as VX-740, anti-FcR1 antibodies such as MDX-33, anti-IgE antibodies such as rhuMab-E25, anti-IL-4 antibodies such as SB-240683, anti-IL-5 antibodies such as SB-240563, SCH55700, anti-IL-8 antibodies such as ABX-IL8, anti-interferon gamma antibodies, anti-TNF (TNF, TNFa, TNFa, TNF-alpha) antibodies such as CDP571, CDP870, D2E7, Infliximab, MAK-195F, and anti-VLA-4 antibodies such as Antegren.

Fc variants of the present invention such as those with increased binding to FcRn may be utilized in TNF inhibitor molecules to provide enhanced properties. Useful TNF inhibitor molecules include any molecule that inhibits the action of TNF-alpha in a mammal. Suitable examples include the Fc fusion Enbrel® (etanercept) and the antibodies Humira® (adalimumab) and Remicade® (infliximab). Monoclonal antibodies (such as Remicade and Humira) engineered using the Fc variants of the present invention to increase FcFn binding, may translate to better efficacy through an increased half-life.

In some embodiments, antibodies against infectious diseases are used. Antibodies against eukaryotic cells include antibodies targeting yeast cells, including but not limited to *Saccharomyces cerevisiae, Hansenula polymorpha, Kluyveromyces fragilis* and *K. lactis, Pichia guillerimondii* and *P. pastoris, Schizosaccharomyces pombe, plasmodium falciparium*, and *Yarrowia lipolytica*.

Antibodies against additional fungal cells are also useful, including target antigens associated with *Candida* strains including *Candida glabrata, Candida albicans, C. krusei, C. lusitaniae* and *C. maltosa*, as well as species of *Aspergillus, Cryptococcus, Histoplasma, Coccidioides, Blastomyces*, and *Penicillium*, among others Antibodies directed against target antigens associated with protozoa include, but are not limited to, antibodies associated with *Trypanosoma, Leishmania* species including *Leishmania donovanii; Plasmodium* spp., *Pneumocystis carinii, Cryptosporidium parvum, Giardia lamblia, Entamoeba histolytica*, and *Cyclospora cayetanensis*.

Antibodies against prokaryotic antigens are also useful, including antibodies against suitable bacteria such as pathogenic and non-pathogenic prokaryotes including but not limited to *Bacillus*, including *Bacillus anthracis; Vibrio*, e.g. *V. cholerae; Escherchia*, e.g. Enterotoxigenic *E. coli, Shigella*, e.g. *S. dysenteriae; Salmonella*, e.g. *S. typhi; Mycobacterium* e.g. *M. tuberculosis, M. leprae; Clostridium*, e.g. *C. botulinum, C. tetani, C. difficile, C. pefringens; Cornyebacterium*, e.g. *C. diphtheriae; Streptococcus, S. pyogenes, S. pneumoniae; Staphylococcus*, e.g. *S. aureus; Haemophilus*, e.g. *H. influenzae; Neisseria*, e.g. *N. meningitidis, N. gonorrhoeae; Yersinia*, e.g. *Y. lamblia, Y. pestis, Pseudomonas*, e.g. *P. aeruginosa, P. putida; Chlamydia*, e.g. *C. trachomatis; Bordetella*, e.g. *B. pertussis; Treponema*, e.g. *T. palladium; B. anthracis, Y. pestis, Brucella* spp., *F. tularensis, B. mallei, B. pseudomallei, B. mallei, B. pseudomallei, C. botulinum, Salmonella* spp., SEB *V. cholerae* toxin B, *E. coli* O157:H7, *Listeria* spp., *Trichosporon beigelii, Rhodotorula* species, *Hansenula anomala, Enterobacter* sp., *Klebsiella* sp., *Listeria* sp., *Mycoplasma* sp. and the like.

In some aspects, the antibodies are directed against viral infections; these viruses include, but are not limited to, including orthomyxoviruses, (e.g. influenza virus), paramyxoviruses (e.g respiratory syncytial virus, mumps virus, measles virus), adenoviruses, rhinoviruses, coronaviruses, reoviruses, togaviruses (e.g. rubella virus), parvoviruses, poxviruses (e.g. variola virus, vaccinia virus), enteroviruses (e.g. poliovirus, coxsackievirus), hepatitis viruses (including A, B and C), herpesviruses (e.g. Herpes simplex virus, varicella-zoster virus, cytomegalovirus, Epstein-Barr virus), rotaviruses, Norwalk viruses, hantavirus, arenavirus, rhabdovirus (e.g. rabies virus), retroviruses (including HIV, HTLV-I and -II), papovaviruses (e.g. papillomavirus), polyomaviruses, and picornaviruses, and the like.

Optimized IgG Variant Properties

The present application also provides IgG variants that are optimized for a variety of therapeutically relevant properties. An IgG variant that is engineered or predicted to display one or more optimized properties is herein referred to as an "optimized IgG variant". The most preferred properties that may be optimized include but are not limited to enhanced or reduced affinity for a FcRn and increased or decreased in vivo half-life. Suitable embodiments include antibodies that exhibit increased binding affinity to FcRn at lowered pH, such as the pH associated with endosomes, e.g. pH 6.0, while not displaying corresponding increased binding affinity at higher pH, such as 7.4, to allow increased uptake into endosomes but normal release rates. Similarly, these antibodies with modulated FcRn binding may optionally have other desirable properties, such as modulated FcγR binding, such as outlined in U.S. Ser. Nos. 11/174,287, 11/124,640, 10/822,231, 10/672,280, 10/379,392, and the patent application entitled IgG Immunoglobulin variants with optimized effector function filed on Oct. 21, 2005 having application Ser. No. 11/256,060. That is, optimized properties also include but are not limited to enhanced or reduced affinity for an FcγR. In one optional embodiment, the IgG variants are optimized to possess enhanced affinity for a human activating FcγR, preferably FcγRIIIa in addition to the FcRn binding profile. In yet another optional alternate embodiment, the IgG variants are optimized to possess reduced affinity for the human inhibitory receptor FcγRIIb. That is, particular embodiments embrace the use of antibodies that show increased binding to FcRn, and increased binding to FcγRIIa. Other embodiments utilize use of antibodies that show increased binding to FcRn, and increased binding to FcγRIIIa. These embodiments are anticipated to provide IgG polypeptides with enhanced therapeutic properties in humans, for example enhanced effector function and greater anti-cancer potency. In an alternate embodiment, the IgG variants are optimized to have increased or reduced affinity for FcRn and increased or decreased affinity for a human FcγR, including but not limited to FcγRI, FcγRIIa, FcγRII b, FcγRIIc, FcγRIIIa, and FcγRIIIb including their allelic variations. These embodiments are anticipated to provide IgG polypeptides with enhanced therapeutic properties in humans, for example increased serum half-life and reduced effector function. In other embodiments, IgG variants provide enhanced affinity for FcRn and enhanced affinity for one or more FcγRs, yet reduced affinity for one or more other FcγRs. For example, an IgG variant may have enhanced binding to FcRn and FcγRIIIa, yet reduced binding to FcγRIIb. Alternately, an IgG variant may have reduced binding to FcRn and to FcγR's. In another embodiment, an IgG variant may have reduced affinity for FcRn and enhanced affinity for FcγRII b, yet reduced affinity to one or more activating FcγRs. In yet another embodiment, an IgG variant may have increased serum half-life and reduced effector functions.

Preferred embodiments comprise optimization of binding to a human FcRn and FcγR, however in alternate embodiments the IgG variants possess enhanced or reduced affinity for FcRn and FcγR from nonhuman organisms, including but not limited to rodents and non-human primates. IgG variants that are optimized for binding to a nonhuman FcRn may find use in experimentation. For example, mouse models are available for a variety of diseases that enable testing of properties such as efficacy, toxicity, and pharmacokinetics for a given drug candidate. As is known in the art, cancer cells can be grafted or injected into mice to mimic a human cancer, a process referred to as xenografting. Testing of IgG variants that comprise IgG variants that are optimized for FcRn may provide valuable information with regard to the clearance characteristics of the protein, its mechanism of clearance, and the like. The IgG variants may also be optimized for enhanced functionality and/or solution properties in aglycosylated form. The Fc ligands include but are not limited to FcRn, FcγRs, C1q, and proteins A and G, and may be from any source including but not limited to human, mouse, rat, rabbit, or monkey, preferably human. In an alternately preferred embodiment, the IgG variants are optimized to be more stable and/or more soluble than the aglycosylated form of the parent IgG variant.

IgG variants can include modifications that modulate interaction with Fc ligands other than FcRn and FcγRs, including but not limited to complement proteins, and Fc receptor homologs (FcRHs). FcRHs include but are not limited to FcRH1, FcRH2, FcRH3, FcRH4, FcRH5, and FcRH6 (Davis et al., 2002, Immunol. Reviews 190:123-136, entirely incorporated by reference).

Preferably, the Fc ligand specificity of the IgG variant will determine its therapeutic utility. The utility of a given IgG variant for therapeutic purposes will depend on the epitope or form of the target antigen and the disease or indication being treated. For most targets and indications, enhanced FcRn binding may be preferable as the enhanced FcRn binding may result in an increase in serum half-life. Longer serum half-lives allow less frequent dosing or lower dosing of the therapeutic. This is particularly preferable when the therapeutic agent is given in response to an indication that requires repeated administration. For some targets and indications, decreased FcRn affinity may be preferable. This may be particularly preferable when a variant Fc with increased clearance or decreased serum half-life is desired, for example in Fc polypeptides used as imaging agents or radio-therapeutics.

IgG variants may be used that comprise IgG variants that provide enhanced affinity for FcRn with enhanced activating FcγRs and/or reduced affinity for inhibitory FcγRs. For some targets and indications, it may be further beneficial to utilize IgG variants that provide differential selectivity for different activating FcγRs; for example, in some cases enhanced binding to FcγRII a and FcγRIIIa may be desired, but not FcγRI, whereas in other cases, enhanced binding only to FcγRII a may be preferred. For certain targets and indications, it may be preferable to utilize IgG variants that alter FcRn binding and enhance both FcγR-mediated and complement-mediated effector functions, whereas for other cases it may be advantageous to utilize IgG variants that enhance FcRn binding, or serum half-life, and either FcγR-mediated or complement-mediated effector functions. For some targets or cancer indications, it may be advantageous to reduce or ablate one or more effector functions, for example by knocking out binding to C1q, one or more FcγR's, FcRn, or one or more other Fc ligands. For other targets and indications, it may be preferable to utilize IgG variants that provide enhanced binding to the inhibitory FcγRIIb, yet WT level, reduced, or ablated binding to activating FcγRs. This may be particularly useful, for example, when the goal of an IgG variant is to inhibit inflammation or auto-immune disease, or modulate the immune system in some way. Because auto-immune diseases are generally long-lasting and treatment is given in repeated dosing, their treatment with Fc variants with increased half-life from increased FcRn is particularly preferred.

Modification may be made to improve the IgG stability, solubility, function, or clinical use. In a preferred embodiment, the IgG variants can include modifications to reduce immunogenicity in humans. In a most preferred embodiment, the immunogenicity of an IgG variant is reduced using a method described in U.S. Ser. No. 11/004,590, entirely incorporated by reference. In alternate embodiments, the IgG variants are humanized (Clark, 2000, Immunol Today 21:397-402, entirely incorporated by reference).

The IgG variants can include modifications that reduce immunogenicity. Modifications to reduce immunogenicity can include modifications that reduce binding of processed peptides derived from the parent sequence to MHC proteins. For example, amino acid modifications would be engineered such that there are no or a minimal number of immune epitopes that are predicted to bind, with high affinity, to any prevalent MHC alleles. Several methods of identifying MHC-binding epitopes in protein sequences are known in the art and may be used to score epitopes in an IgG variant. See for example WO 98/52976; WO 02/079232; WO 00/3317; U.S. Ser. No. 09/903,378; U.S. Ser. No. 10/039,170; U.S. Ser. No. 60/222,697; U.S. Ser. No. 10/754,296; PCT WO 01/21823; and PCT WO 02/00165; Mallios, 1999, Bioinformatics 15: 432-439; Mallios, 2001, Bioinformatics 17: 942-948; Sturniolo et al., 1999, Nature Biotech. 17: 555-561; WO 98/59244; WO 02/069232; WO 02/77187; Marshall et al., 1995, J. Immunol. 154: 5927-5933; and Hammer et al., 1994, J. Exp. Med. 180: 2353-2358, all entirely incorporated by reference. Sequence-based information can be used to determine a binding score for a given peptide—MHC interaction (see for example Mallios, 1999, Bioinformatics 15: 432-439; Mallios, 2001, Bioinformatics 17: p942-948; Sturniolo et. al., 1999, Nature Biotech. 17: 555-561, all entirely incorporated by reference).

Engineering IgG Variants

Variants of the present invention may be designed by various means. The variants, as described herein, may be insertions, deletions, substitutions, other modifications, or combinations of these and other changes. A particularly novel embodiment of the present invention is the design of insertions and deletions that either improve or reduce the binding of an Fc polypeptide to an Fc ligand. As disclosed herein, insertions or deletions may be made that increase or decrease the affinity of the Fc polypeptide for FcRn. Insertions and deletions may be designed by rational approaches or by approaches that include the use or random components, such as random or semi-random library creation or screening. In an alternative embodiment, substitutions are disclosed that increase or decrease the affinity of the Fc polypeptide for FcRn.

Insertions and Deletions

Variant Fc polypeptides may be created by substituting a variant amino acid in place of the parent amino acid at a position in the Fc polypeptide. By substituting one or more amino acids for variant amino acids in the Fc polypeptide, the side chains at those positions are altered. Most useful substitutions modify the Fc properties by altering the Fc side chains. The substituted side chains may interact directly or indirectly with an Fc binding partner that is associated with an Fc function or property. The at least one substitution alters the covalent structure of one or more side chains of the parent Fc polypeptide.

Alternatively, variant Fc polypeptides may be created that change the covalent structure of the backbone of the parent Fc polypeptide. The backbone atoms in proteins are the peptide nitrogen, the alpha carbon, the carbonyl or peptide carbon and the carbonyl oxygen. Changing the covalent structure of the backbone provides additional methods of altering the properties of the Fc polypeptides. The covalent structure of the Fc backbone may be altered by the addition of atoms into the backbone, e.g. by inserting one or more amino acids, or the subtraction of atoms from the backbone, e.g. by deleting one or more amino acids. The covalent structure of the backbone may also be altered by changing individual atoms of the backbone to other atoms (Deechongkit et al., J Am Chem Soc. 2004. 126(51):16762-71, entirely incorporated by reference). As is known in the art and is illustrated herein, insertions or deletions of amino acids in Fc polypeptides may be done by inserting or deleting the corresponding nucleotides in the DNA encoding the Fc polypeptide. Alternatively, as is known in the art, insertions or deletions of amino acids may be done during synthesis of Fc polypeptides.

The design of insertions or deletions of amino acids that alter the interaction of the Fc polypeptide with one or more binding partners (e.g. FcgammaR's, FcRn, C1q) may be done by considering the structure of the complex of the Fc polypeptide and its binding partner. In a less preferred embodiment, the design may be done by considering the structure of the Fc polypeptide and information about the Fc region involved in binding the binding partner. This information may be obtained by mutagenesis experiments, phage display experiments, homology comparisons, computer modeling or other means.

Preferred positions in the amino acid sequence for insertions or deletions that affect the Fc binding interactions, but do not affect the overall structure, stability, expression or use of the Fc polypeptide, are in loops that are involved in the Fc/Fc-binding partner interactions. To alter FcRn binding to the Fc polypeptide, positions 244-257, 279-284, 307-317, 383-390, and 428-435 are preferred loop locations for insertions or deletions (numbering from EU index of Kabat et al., Burmeister et al., 1994, Nature, 372:379-383; Martin et al., 2001, Mol Cell 7:867-877, all entirely incorporated by reference). To alter the Fcgamma receptor binding to the Fc polypeptide, positions 229-239, 266-273, 294-299, and 324-331 are preferred loop locations for insertions or deletions (numbering from EU index of Kabat et al., PDB code 1 E4K.pdb Sondermann et al. Nature. 2000 406:267, all entirely incorporated by reference). Loops are regions of the polypeptide not involved in alpha helical or beta sheet structure. Loops positions are positions that are not in either alpha helical or beta sheet structures (van Holde, Johnson and Ho. Principles of Physical Biochemistry. Prentice Hall, N.J. 1998, Chapter 1 pp2-67, entirely incorporated by reference). Loop positions are preferred because the backbone atoms are typically more flexible and less likely involved in hydrogen bonds compared to the backbone atoms of alpha helices and beta sheets. Therefore, the lengthening or shortening of a loop due to an insertion or deletion of one or more amino acids is less likely to lead to large, disruptive changes to the Fc polypeptide, including stability, expression or other problems.

Insertions and deletions may be used to alter the length of the polypeptide. For example, in loop regions, altering the loop length results in altered flexibility and conformational entropy of the loop. Insertions in a loop will generally increase the conformational entropy of the loop, which may be defined as Boltzman's constant multiplied by the natural logarithm of the number of possible conformations (van Holde, Johnson and Ho. Principles of Physical Biochemistry. Prentice Hall, N.J. 1998, pp78, entirely incorporated by reference). By inserting at least one amino acid into a polypeptide, the total number of conformations available to the polypeptide increases. These additional conformations may be beneficial for forming favorable Fc/Fc-binding partner interactions because the Fc polypeptide may use one of the additional conformations in binding the Fc-binding protein. In this case, the insertion may lead to stronger Fc/Fc-binding partner interactions. If the additional conformations are not used in the binding interface, then the insertion may lead to weaker Fc/Fc-binding partner interactions, because the additional conformations would compete with the binding-competent conformation. Similarly, deletion of a polypeptide segment may also lead to either stronger or weaker Fc/Fc binding-partner interactions. If deletion of a segment, which reduces the possible number of backbone conformations, removes the binding-competent conformation, then the deletion may lead to weaker Fc/Fc-binding partner interactions. If the deletion does not remove the binding-competent conformation, then the deletion may lead to stronger Fc/Fc-binding partner interactions because the deletion may remove conformations that compete with the binding-competent conformation.

Figure 7:
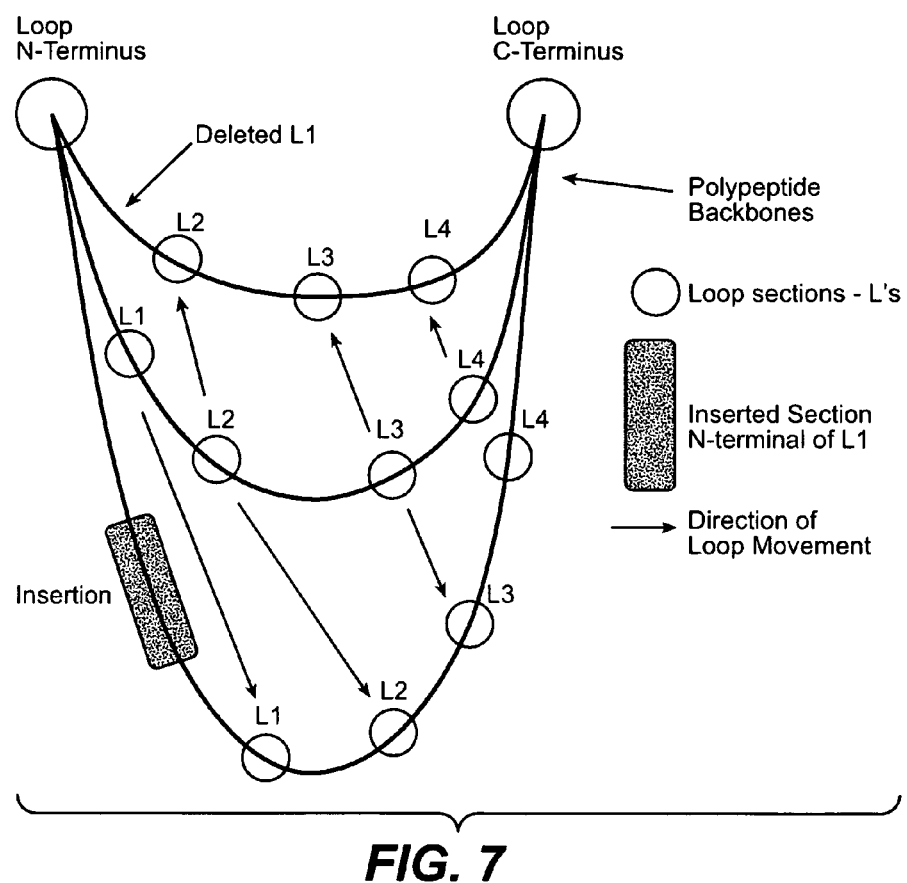
FIG. 7. Illustration of some concepts used in the design of variants comprising insertions or deletions.

Insertions and deletions may be used to alter the positions and orientations of the amino acids in the Fc polypeptide. Because insertions and deletions cause a change in the covalent structure of the backbone, they necessarily cause a change in the positions of the backbone atoms. FIG. 7 compares the backbone positions at some loop segments, marked L1 to L4, in three different backbones. The reference backbone structure contains four loop segments, whereas the deletion backbone lacks segment L1 and the insertion segment comprises an additional segment before, ie, N-terminal to, segment L1. Deletions and insertions cause the largest change in the backbone structure near the site of the insertion or deletion. By deleting a segment near the N-terminal end of the loop, e.g. segment L1, the loop shortens and the remaining segments shift their position closer to the loop N-terminus. This has the effect of moving the L2 segment toward the prior location of the L1 segment and toward the loop N-terminus. This change in position of the L2 segment toward the L1 segment may strengthen the binding of the Fc/Fc-binding partner complex and is preferred when there is prior information suggesting that the amino acid or amino acids located in L2 make favorable interactions with the Fc-binding partner, when located in L1. For example, if L2 contains alanine and tyrosine and substitution of two L1 amino acids for alanine and tyrosine previously lead to an Fc variant with increased binding, then deletion of L1 may create an Fc variant with increased affinity for the Fc-binding partner.

Similarly, an insertion of a polypeptide segment into an Fc polypeptide at the N-terminal side of a loop causes the positions of the loop segments to be shifted toward the C-terminal side of the loop. In FIG. 7, an insertion of one or more amino acids before, i.e. N-terminally to, segment L1 alters the backbone conformation including a shift of the L1 segment toward the C-terminal end of the loop. This type of insertion is preferred when the amino acids located in segment L1 are known to make favorable interactions when located in the L2 positions, as the insertion may lead to stronger Fc/Fc-binding partner interactions. If weaker Fc/Fc-binding partner interactions are desired, then the insertion may be used to shift unfavorable amino acid into a new position. The inserted, deleted and reference segments (L1 to L4 in FIG. 7) may be one or more than one amino acid in the Fc polypeptide.

Alternatively, insertions or deletions may be used at the C-terminal end of loops in a manner analogous to the insertions or deletions at the N-terminal end of loops. Insertions at the loop C-terminus may lead to a movement of the positions N-terminal of the insertion toward the loop N-terminus. Deletions at the loop C-terminus may lead to a movement of the positions N-terminal of the deletion toward the loop C-terminus. The choice of using an insertion or deletion at the N-terminal or C-terminal end of the loop is based on the amino acids located in the loop, the desire for increased or decreased Fc/Fc-binding partner affinity, and the positional shift desired.

Insertions or deletions may be used in any region of an Fc polypeptide, including the loops, the alpha helical, and the beta sheet regions. Preferred locations for insertions and deletions include loop regions, which are those that are not alpha helical or beta sheet regions. Loops are preferred because they generally accept alterations in the backbone better than alpha helixes or beta sheets. The particularly preferred locations for insertions or deletions that result in stronger protein/protein interactions are at the N-terminal or C-terminal edges of a loop. If the loop side chains are involve in the Fc/Fc-binding partner interactions, then insertions or deletion at the edges are less likely to lead to strongly detrimental changes in the binding interactions. Deletions within the exact center of the loop are more likely to remove important residues in the Fc/Fc-binding partner interface and insertions within the exact center of the loop are more likely to create unfavorable interactions in the Fc/Fc-binding partner interface. The number of residues deleted or inserted may be determined by the size of the backbone change desired with insertions or deletions of 15 or less residues being preferred, insertions or deletions of 10 or less residues being more preferred, and insertions or deletions of 5 or less residues being most preferred.

Once the position and size of an Fc deletion variant is designed, the entire polypeptide sequence is completely determined and the polypeptide may be constructed by methods known in the art.

Fc insertion variants, however, have the additional step of designing the sequence of the at least one amino acid to be inserted. Insertions of polar residues, including Ser, Thr, Asn, Gkn, Ala, Gly, His, are preferred at positions expected to be exposed in the Fc polypeptide. The smaller amino acids, including Ser, Thr, and Ala, are particularly preferred as the small size is less likely to sterically interfere with the Fc/Fc-binding partner interactions. Ser and Thr also have the capability to hydrogen bond with atoms on the Fc-binding partner.

Insertions also have the added flexibility that the inserted polypeptide may be designed to make favorable interactions with the Fc-binding partner as would be desire when stronger Fc/Fc-binding partner binding is desired. The length of the backbone insertion may be determined by modeling the variant backbone with a simple, generic sequence to be inserted. For example, polyserine, polyglycine or polyalanine insertions of different lengths may be constructed and modeled. Modeling may be done by a variety of methods, including homology modeling based on known three-dimensional structures of homologues comprising the insertion, and by computer modeling including MODELLER (M. A. Marti-Renom et al. Annu. Rev. Biophys. Biomol. Struct. 29, 291-325, 2000) and ROSETTA (Kuhlman et al. (2003). Science 302, 1364-8), both entirely incorporated by reference. Typically, various backbone conformations are initially generated and the final backbone structure may be determined after the identities of the side chain are established. The side chains may be designed by PDA® algorithms (U.S. Pat. Nos. 6,188,965; 6,269,312; 6,403,312; 6,801,861; 6,804,611; 6,792,356, 6,950,754, and U.S. Ser. No. 09/782,004; 09/927,790; 10/101,499; 10/666,307; 10/666,311; 10/218,102, all entirely incorporated by reference).

Insertions and deletion may be designed in any polypeptide besides Fc polypeptides by the methods described herein. For example, insertions or deletions in the TNF superfamily member, APRIL, may be designed with the aid of its three-dimensional structure (PDB code 1XU1.pdb, Hymowitz, et al. (2005) J. Biol. Chem. 280:7218, entirely incorporated by reference). Insertions or deletions may be designed to increase APRIL binding to its receptor, TACI. The loop residues preferred as insertion or deletion sites are residues Ser 18-Val124, Asp164-Phe167, Pro192-Ala198, Pro221-Lys226. These loops interact with TACI in the APRIL/TACI complex and mediate binding.

Polypeptides Incorporating Variants

The IgG variants can be based on human IgG sequences, and thus human IgG sequences are used as the "base" sequences against which other sequences are compared, including but not limited to sequences from other organisms, for example rodent and primate sequences. IgG variants may also comprise sequences from other immunoglobulin classes such as IgA, IgE, IgD, IgM, and the like. It is contemplated that, although the IgG variants are engineered in the context of one parent IgG, the variants may be engineered in or "transferred" to the context of another, second parent IgG. This is done by determining the "equivalent" or "corresponding" residues and substitutions between the first and second IgG, typically based on sequence or structural homology between the sequences of the IgGs. In order to establish homology, the amino acid sequence of a first IgG outlined herein is directly compared to the sequence of a second IgG. After aligning the sequences, using one or more of the homology alignment programs known in the art (for example using conserved residues as between species), allowing for necessary insertions and deletions in order to maintain alignment (i.e., avoiding the elimination of conserved residues through arbitrary deletion and insertion), the residues equivalent to particular amino acids in the primary sequence of the first IgG variant are defined. Alignment of conserved residues preferably should conserve 100% of such residues. However, alignment of greater than 75% or as little as 50% of conserved residues is also adequate to define equivalent residues. Equivalent residues may also be defined by determining structural homology between a first and second IgG that is at the level of tertiary structure for IgGs whose structures have been determined. In this case, equivalent residues are defined as those for which the atomic coordinates of two or more of the main chain atoms of a particular amino acid residue of the parent or precursor (N on N, CA on CA, C on C and O on O) are within 0.13 nm and preferably 0.1 nm after alignment. Alignment is achieved after the best model has been oriented and positioned to give the maximum overlap of atomic coordinates of non-hydrogen protein atoms of the proteins. Regardless of how equivalent or corresponding residues are determined, and regardless of the identity of the parent IgG in which the IgGs are made, what is meant to be conveyed is that the IgG variants discovered by can be engineered into any second parent IgG that has significant sequence or structural homology with the IgG variant. Thus for example, if a variant antibody is generated wherein the parent antibody is human IgG1, by using the methods described above or other methods for determining equivalent residues, the variant antibody may be engineered in another IgG1 parent antibody that binds a different antigen, a human IgG2 parent antibody, a human IgA parent antibody, a mouse IgG2a or IgG2b parent antibody, and the like. Again, as described above, the context of the parent IgG variant does not affect the ability to transfer the IgG variants to other parent IgGs.

Methods for engineering, producing, and screening IgG variants are provided. The described methods are not meant to constrain to any particular application or theory of operation. Rather, the provided methods are meant to illustrate generally that one or more IgG variants may be engineered, produced, and screened experimentally to obtain IgG variants with optimized effector function. A variety of methods are described for designing, producing, and testing antibody and protein variants in U.S. Ser. No. 10/754,296, and U.S. Ser. No. 10/672,280, both entirely incorporated by reference.

A variety of protein engineering methods may be used to design IgG variants with optimized effector function. In one embodiment, a structure-based engineering method may be used, wherein available structural information is used to guide substitutions, insertions or deletions. In a preferred embodiment, a computational screening method may be used, wherein substitutions are designed based on their energetic fitness in computational calculations. See for example U.S. Ser. No. 10/754,296 and U.S. Ser. No. 10/672,280, and references cited therein, all entirely incorporated by reference.

An alignment of sequences may be used to guide substitutions at the identified positions. One skilled in the art will appreciate that the use of sequence information may curb the introduction of substitutions that are potentially deleterious to protein structure. The source of the sequences may vary widely, and include one or more of the known databases, including but not limited to the Kabat database (Northwestern University); Johnson & Wu, 2001, *Nucleic Acids Res.* 29:205-206; Johnson & Wu, 2000, *Nucleic Acids Res.* 28:214-218), the IMGT database (IMGT, the international ImMunoGeneTics information System®; ; Lefranc et al., 1999, *Nucleic Acids Res.* 27:209-212; Ruiz et al., 2000 *Nucleic Acids Res.* 28:219-221; Lefranc et al., 2001, *Nucleic Acids Res.* 29:207-209; Lefranc et al., 2003, *Nucleic Acids Res.* 31:307-310), and VBASE, all entirely incorporated by reference. Antibody sequence information can be obtained, compiled, and/or generated from sequence alignments of germline sequences or sequences of naturally occurring antibodies from any organism, including but not limited to mammals. One skilled in the art will appreciate that the use of sequences that are human or substantially human may further have the advantage of being less immunogenic when administered to a human. Other databases which are more general nucleic acid or protein databases, i.e. not particular to antibodies, include but are not limited to SwissProt, GenBank Entrez, and EMBL Nucleotide Sequence Database. Aligned sequences can include VH, VL, CH, and/or CL sequences. There are numerous sequence-based alignment programs and methods known in the art, and all of these find use in the generation of sequence alignments.

Alternatively, random or semi-random mutagenesis methods may be used to make amino acid modifications at the desired positions. In these cases positions are chosen randomly, or amino acid changes are made using simplistic rules. For example all residues may be mutated to alanine, referred to as alanine scanning. Such methods may be coupled with more sophisticated engineering approaches that employ selection methods to screen higher levels of sequence diversity. As is well known in the art, there are a variety of selection technologies that may be used for such approaches, including, for example, display technologies such as phage display, ribosome display, cell surface display, and the like, as described below.

Methods for production and screening of IgG variants are well known in the art. General methods for antibody molecular biology, expression, purification, and screening are described in Antibody Engineering, edited by Duebel & Kontermann, Springer-Verlag, Heidelberg, 2001; and Hayhurst & Georgiou, 2001, *Curr Opin Chem Biol* 5:683-689; Maynard & Georgiou, 2000, *Annu Rev Biomed Eng* 2:339-76. Also see the methods described in U.S. Ser. No. 10/754,296; U.S. Ser. No. 10/672,280; and U.S. Ser. Nos. 10/822,231; and 11/124,620, all entirely incorporated by reference.

Preferred variants of the present invention include those found in FIG. 8. Alternatively preferred variants of the present invention include those found in FIG. 9. Additionally alternatively preferred variants of the present invention include those found in FIG. 10. Particularly preferred variants of the present invention include G385H and N434Y. Most preferred variants of the present invention include 257C, 257M, 257L, 257N, 257Y, 279Q, 279Y, 308F, and 308Y.

Making IgG Variants

The IgG variants can be made by any method known in the art. In one embodiment, the IgG variant sequences are used to create nucleic acids that encode the member sequences, and that may then be cloned into host cells, expressed and assayed, if desired. These practices are carried out using well-known procedures, and a variety of methods that may find use in are described in Molecular Cloning—A Laboratory Manual, 3$^{rd}$ Ed. (Maniatis, Cold Spring Harbor Laboratory Press, New York, 2001), and Current Protocols in Molecular Biology (John Wiley & Sons), both entirely incorporated by reference. The nucleic acids that encode the IgG variants may be incorporated into an expression vector in order to express the protein. Expression vectors typically include a protein operably linked, that is, placed in a functional relationship, with control or regulatory sequences, selectable markers, any fusion partners, and/or additional elements. The IgG variants may be produced by culturing a host cell transformed with nucleic acid, preferably an expression vector, containing nucleic acid encoding the IgG variants, under the appropriate conditions to induce or cause expression of the protein. A wide variety of appropriate host cells may be used, including but not limited to mammalian cells, bacteria, insect cells, and yeast. For example, a variety of cell lines that may find use are described in the ATCC cell line catalog, available from the American Type Culture Collection, entirely incorporated by reference. The methods of introducing exogenous nucleic acid into host cells are well known in the art, and will vary with the host cell used.

In a preferred embodiment, IgG variants are purified or isolated after expression. Antibodies may be isolated or purified in a variety of ways known to those skilled in the art. Standard purification methods include chromatographic techniques, electrophoretic, immunological, precipitation, dialysis, filtration, concentration, and chromatofocusing techniques. As is well known in the art, a variety of natural proteins bind antibodies, for example bacterial proteins A, G, and L, and these proteins may find use in purification. Often, purification may be enabled by a particular fusion partner. For example, proteins may be purified using glutathione resin if a GST fusion is employed, $Ni^{+2}$ affinity chromatography if a His-tag is employed, or immobilized anti-flag antibody if a flag-tag is used. For general guidance in suitable purification techniques, see Antibody Purification: Principles and Practice, $3^{rd}$ Ed., Scopes, Springer-Verlag, NY, 1994, entirely incorporated by reference.

Screening IgG Variants

IgG variants may be screened using a variety of methods, including but not limited to those that use in vitro assays, in vivo and cell-based assays, and selection technologies. Automation and high-throughput screening technologies may be utilized in the screening procedures. Screening may employ the use of a fusion partner or label, for example an immune label, isotopic label, or small molecule label such as a fluorescent or colorimetric dye.

In a preferred embodiment, the functional and/or biophysical properties of IgG variants are screened in an in vitro assay. In a preferred embodiment, the protein is screened for functionality, for example its ability to catalyze a reaction or its binding affinity to its target. Binding assays can be carried out using a variety of methods known in the art, including but not limited to FRET (Fluorescence Resonance Energy Transfer) and BRET (Bioluminescence Resonance Energy Transfer)-based assays, AlphaScreen™ (Amplified Luminescent Proximity Homogeneous Assay), Scintillation Proximity Assay, ELISA (Enzyme-Linked Immunosorbent Assay), SPR (Surface Plasmon Resonance, also known as BIACORE®), isothermal titration calorimetry, differential scanning calorimetry, gel electrophoresis, and chromatography including gel filtration. These and other methods may take advantage of some fusion partner or label. Assays may employ a variety of detection methods including but not limited to chromogenic, fluorescent, luminescent, or isotopic labels. The biophysical properties of proteins, for example stability and solubility, may be screened using a variety of methods known in the art. Protein stability may be determined by measuring the thermodynamic equilibrium between folded and unfolded states. For example, IgG variants may be unfolded using chemical denaturant, heat, or pH, and this transition may be monitored using methods including but not limited to circular dichroism spectroscopy, fluorescence spectroscopy, absorbance spectroscopy, NMR spectroscopy, calorimetry, and proteolysis. As will be appreciated by those skilled in the art, the kinetic parameters of the folding and unfolding transitions may also be monitored using these and other techniques. The solubility and overall structural integrity of a IgG variant may be quantitatively or qualitatively determined using a wide range of methods that are known in the art. Methods which may find use in for characterizing the biophysical properties of IgG variants include gel electrophoresis, chromatography such as size exclusion chromatography and reversed-phase high performance liquid chromatography, mass spectrometry, ultraviolet absorbance spectroscopy, fluorescence spectroscopy, circular dichroism spectroscopy, isothermal titration calorimetry, differential scanning calorimetry, analytical ultra-centrifugation, dynamic light scattering, proteolysis, and cross-linking, turbidity measurement, filter retardation assays, immunological assays, fluorescent dye binding assays, protein-staining assays, microscopy, and detection of aggregates via ELISA or other binding assay. Structural analysis employing X-ray crystallographic techniques and NMR spectroscopy may also find use.

As is known in the art, a subset of screening methods comprises those that select for favorable members of a library. The methods are herein referred to as "selection methods", and these methods find use in screening IgG variants. When protein libraries are screened using a selection method, only those members of a library that are favorable, that is which meet some selection criteria, are propagated, isolated, and/or observed. As will be appreciated, because only the most fit variants are observed, such methods enable the screening of libraries that are larger than those screenable by methods that assay the fitness of library members individually. Selection is enabled by any method, technique, or fusion partner that links, covalently or noncovalently, the phenotype of a protein with its genotype, that is, the function of a protein with the nucleic acid that encodes it. For example the use of phage display as a selection method is enabled by the fusion of library members to the gene III protein. In this way, selection or isolation of IgG variants that meet some criteria, for example binding affinity to the protein's target, also selects for or isolates the nucleic acid that encodes it. Once isolated, the gene or genes encoding Fc variants may then be amplified. This process of isolation and amplification, referred to as panning, may be repeated, allowing favorable IgG variants in the library to be enriched. Nucleic acid sequencing of the attached nucleic acid ultimately allows for gene identification.

A variety of selection methods are known in the art that may find use in screening protein libraries. These include but are not limited to phage display (Phage display of peptides and proteins: a laboratory manual, Kay et al., 1996, Academic Press, San Diego, Calif., 1996; Lowman et al., 1991, *Biochemistry* 30:10832-10838; Smith, 1985, *Science* 228:1315-1317) and its derivatives such as selective phage infection (Malmborg et al., 1997, J Mol Biol 273:544-551), selectively infective phage (Krebber et al., 1997, *J Mol Biol* 268:619-630), and delayed infectivity panning (Benhar et al., 2000, *J Mol Biol* 301:893-904), cell surface display (Witrrup, 2001, *Curr Opin Biotechnol,* 12:395-399) such as display on bacteria (Georgiou et al., 1997, *Nat Biotechnol* 15:29-34; Georgiou et al., 1993, *Trends Biotechnol* 11:6-10; Lee et al., 2000, *Nat Biotechnol* 18:645-648; Jun et al., 1998, *Nat Biotechnol* 16:576-80), yeast (Boder & Wittrup, 2000, *Methods Enzymol* 328:430-44; Boder & Wittrup, 1997, *Nat Biotechnol* 15:553-557), and mammalian cells (Whitehorn et al., 1995, *Bio/technology* 13:1215-1219), as well as in vitro display technologies (Amstutz et al., 2001, *Curr Opin Biotechnol* 12:400-405) such as polysome display (Mattheakis et al., 1994, *Proc Natl Acad Sci USA* 91:9022-9026), ribosome display (Hanes et al., 1997, *Proc Natl Acad Sci USA* 94:4937-4942), mRNA display (Roberts & Szostak, 1997, *Proc Natl Acad Sci USA* 94:12297-12302; Nemoto et al., 1997, *FEBS Lett* 414:405-408), and ribosome-inactivation display system (Zhou et al., 2002, *J Am Chem Soc* 124,538-543). All references entirely incorporated by reference in this paragraph.

Other selection methods that may find use include methods that do not rely on display, such as in vivo methods including but not limited to periplasmic expression and cytometric screening (Chen et al., 2001, Nat Biotechnol 19:537-542, entirely incorporated by reference), the protein fragment complementation assay (Johnsson & Varshavsky, 1994, *Proc Natl Acad Sci USA* 91:10340-10344; Pelletier et al., 1998, Proc *Natl Acad Sci USA* 95:12141-12146, all entirely incorporated by reference), and the yeast two hybrid screen (Fields & Song, 1989, *Nature* 340:245-246, entirely incorporated by reference) used in selection mode (Visintin et al., 1999, *Proc Natl Acad Sci USA* 96:11723-11728, entirely incorporated by reference). In an alternate embodiment, selection is enabled by a fusion partner that binds to a specific sequence on the expression vector, thus linking covalently or noncovalently the fusion partner and associated Fc variant library member with the nucleic acid that encodes them. For example, U.S. Ser. No. 09/642,574; U.S. Ser. No. 10/080,376; U.S. Ser. No. 09/792,630; U.S. Ser. No. 10/023,208; U.S. Ser. No. 09/792,626; U.S. Ser. No. 10/082,671; U.S. Ser. No. 09/953,351; U.S. Ser. No. 10/097,100; U.S. Ser. No. 60/366, 658; PCT WO 00/22906; PCT WO 01/49058; PCT WO 02/04852; PCT WO 02/04853; PCT WO 02/08023; PCT WO 01/28702; and PCT WO 02/07466, all entirely incorporated by reference, describe such a fusion partner and technique that may find use. In an alternative embodiment, in vivo selection can occur if expression of the protein imparts some growth, reproduction, or survival advantage to the cell.

A subset of selection methods referred to as "directed evolution" methods are those that include the mating or breading of favorable sequences during selection, sometimes with the incorporation of new mutations. As will be appreciated by those skilled in the art, directed evolution methods can facilitate identification of the most favorable sequences in a library, and can increase the diversity of sequences that are screened. A variety of directed evolution methods are known in the art that may find use in for screening IgG variants, including but not limited to DNA shuffling (PCT WO 00/42561 A3; PCT WO 01/70947 A3), exon shuffling (U.S. Pat. No. 6,365,377; Kolkman & Stemmer, 2001, *Nat Biotechnol* 19:423-428), family shuffling (Crameri et al., 1998, *Nature* 391:288-291; U.S. Pat. No. 6,376,246), RACHITT™ (Coco et al., 2001, *Nat Biotechnol* 19:354-359; PCT WO 02/06469), STEP and random priming of in vitro recombination (Zhao et al., 1998, *Nat Biotechnol* 16:258-261; Shao et al., 1998, *Nucleic Acids Res* 26:681-683), exonuclease mediated gene assembly (U.S. Pat. No. 6,352,842; U.S. Pat. No. 6,361,974), Gene Site Saturation Mutagenesis™ (U.S. Pat. No. 6,358,709), Gene Reassembly™ (U.S. Pat. No. 6,358, 709), SCRATCHY (Lutz et al., 2001, *Proc Natl Acad Sci USA* 98:11248-11253), DNA fragmentation methods (Kikuchi et al., *Gene* 236:159-167), single-stranded DNA shuffling (Kikuchi et al., 2000, *Gene* 243:133-137), and AMEsystem™ directed evolution protein engineering technology (Applied Molecular Evolution) (U.S. Pat. No. 5,824,514; U.S. Pat. No. 5,817,483; U.S. Pat. No. 5,814,476; U.S. Pat. No. 5,763,192; U.S. Pat. No. 5,723,323). All references cited in the paragraph are entirely incorporated by reference.

In a preferred embodiment, IgG variants are screened using one or more cell-based or in vivo assays. For such assays, purified or unpurified proteins are typically added exogenously such that cells are exposed to individual variants or pools of variants belonging to a library. These assays are typically, but not always, based on the function of the IgG; that is, the ability of the IgG to bind to its target and mediate some biochemical event, for example effector function, ligand/receptor binding inhibition, apoptosis, and the like. Such assays often involve monitoring the response of cells to the IgG, for example cell survival, cell death, change in cellular morphology, or transcriptional activation such as cellular expression of a natural gene or reporter gene. For example, such assays may measure the ability of IgG variants to elicit ADCC, ADCP, or CDC. For some assays additional cells or components, that is in addition to the target cells, may need to be added, for example example serum complement, or effector cells such as peripheral blood monocytes (PBMCs), NK cells, macrophages, and the like. Such additional cells may be from any organism, preferably humans, mice, rat, rabbit, and monkey. Antibodies may cause apoptosis of certain cell lines expressing the target, or they may mediate attack on target cells by immune cells, which have been added to the assay. Methods for monitoring cell death or viability are known in the art, and include the use of dyes, immunochemical, cytochemical, and radioactive reagents. For example, caspase staining assays may enable apoptosis to be measured, and uptake or release of radioactive substrates or fluorescent dyes such as alamar blue may enable cell growth or activation to be monitored. In a preferred embodiment, the DELFIA® EuTDA-based cytotoxicity assay (Perkin Elmer, Mass.) is used. Alternatively, dead or damaged target cells may be monitored by measuring the release of one or more natural intracellular proteins, for example lactate dehydrogenase. Transcriptional activation may also serve as a method for assaying function in cell-based assays. In this case, response may be monitored by assaying for natural genes or proteins which may be upregulated, for example the release of certain interleukins may be measured, or alternatively readout may be via a reporter construct. Cell-based assays may also involve the measure of morphological changes of cells as a response to the presence of a protein. Cell types for such assays may be prokaryotic or eukaryotic, and a variety of cell lines that are known in the art may be employed. Alternatively, cell-based screens are performed using cells that have been transformed or transfected with nucleic acids encoding the variants. That is, IgG variants are not added exogenously to the cells. For example, in one embodiment, the cell-based screen utilizes cell surface display. A fusion partner can be employed that enables display of IgG variants on the surface of cells (Witrrup, 2001, *Curr Opin Biotechnol*, 12:395-399, entirely incorporated by reference).

In a preferred embodiment, the immunogenicity of the IgG variants is determined experimentally using one or more cell-based assays. Several methods can be used for experimental confirmation of epitopes. In a preferred embodiment, ex vivo T-cell activation assays are used to experimentally quantitate immunogenicity. In this method, antigen presenting cells and naïve T cells from matched donors are challenged with a peptide or whole protein of interest one or more times. Then, T cell activation can be detected using a number of methods, for example by monitoring production of cytokines or measuring uptake of tritiated thymidine. In the most preferred embodiment, interferon gamma production is monitored using Elispot assays (Schmittel et. al., 2000, *J. Immunol. Meth.* 24: 17-24, entirely incorporated by reference).

The biological properties of the IgG variants may be characterized in cell, tissue, and whole organism experiments. As is known in the art, drugs are often tested in animals, including but not limited to mice, rats, rabbits, dogs, cats, pigs, and monkeys, in order to measure a drug's efficacy for treatment against a disease or disease model, or to measure a drug's pharmacokinetics, toxicity, and other properties. The animals may be referred to as disease models. Therapeutics are often tested in mice, including but not limited to nude mice, SCID mice, xenograft mice, and transgenic mice (including knock-ins and knockouts). Such experimentation may provide meaningful data for determination of the potential of the protein to be used as a therapeutic. Any organism, preferably mammals, may be used for testing. For example because of their genetic similarity to humans, monkeys can be suitable therapeutic models, and thus may be used to test the efficacy, toxicity, pharmacokinetics, or other property of the IgGs. Tests of the in humans are ultimately required for approval as drugs, and thus of course these experiments are contemplated. Thus the IgGs may be tested in humans to determine their therapeutic efficacy, toxicity, immunogenicity, pharmacokinetics, and/or other clinical properties.

Methods of Using IgG Variants

The IgG variants may find use in a wide range of products. In one embodiment the IgG variant is a therapeutic, a diagnostic, or a research reagent, preferably a therapeutic. The IgG variant may find use in an antibody composition that is monoclonal or polyclonal. In a preferred embodiment, the IgG variants are used to kill target cells that bear the target antigen, for example cancer cells. In an alternate embodiment, the IgG variants are used to block, antagonize or agonize the target antigen, for example for antagonizing a cytokine or cytokine receptor. In an alternately preferred embodiment, the IgG variants are used to block, antagonize or agonize the target antigen and kill the target cells that bear the target antigen.

The IgG variants may be used for various therapeutic purposes. In a preferred embodiment, an antibody comprising the IgG variant is administered to a patient to treat an antibody-related disorder. A "patient" for the purposes includes humans and other animals, preferably mammals and most preferably humans. By "antibody related disorder" or "antibody responsive disorder" or "condition" or "disease" herein are meant a disorder that may be ameliorated by the administration of a pharmaceutical composition comprising an IgG variant. Antibody related disorders include but are not limited to autoimmune diseases, immunological diseases, infectious diseases, inflammatory diseases, neurological diseases, and oncological and neoplastic diseases including cancer. By "cancer" and "cancerous" herein refer to or describe the physiological condition in mammals that is typically characterized by unregulated cell growth. Examples of cancer include but are not limited to carcinoma, lymphoma, blastoma, sarcoma (including liposarcoma), neuroendocrine tumors, mesothelioma, schwanoma, meningioma, adenocarcinoma, melanoma, and leukemia and lymphoid malignancies.

In one embodiment, an IgG variant is the only therapeutically active agent administered to a patient. Alternatively, the IgG variant is administered in combination with one or more other therapeutic agents, including but not limited to cytotoxic agents, chemotherapeutic agents, cytokines, growth inhibitory agents, anti-hormonal agents, kinase inhibitors, anti-angiogenic agents, cardioprotectants, or other therapeutic agents. The IgG vararians may be administered concomitantly with one or more other therapeutic regimens. For example, an IgG variant may be administered to the patient along with chemotherapy, radiation therapy, or both chemotherapy and radiation therapy. In one embodiment, the IgG variant may be administered in conjunction with one or more antibodies, which may or may not be an IgG variant. In accordance with another embodiment, the IgG variant and one or more other anti-cancer therapies are employed to treat cancer cells ex vivo. It is contemplated that such ex vivo treatment may be useful in bone marrow transplantation and particularly, autologous bone marrow transplantation. It is of course contemplated that the IgG variants can be employed in combination with still other therapeutic techniques such as surgery.

A variety of other therapeutic agents may find use for administration with the IgG variants. In one embodiment, the IgG is administered with an anti-angiogenic agent. By "anti-angiogenic agent" as used herein is meant a compound that blocks, or interferes to some degree, the development of blood vessels. The anti-angiogenic factor may, for instance, be a small molecule or a protein, for example an antibody, Fc fusion, or cytokine, that binds to a growth factor or growth factor receptor involved in promoting angiogenesis. The preferred anti-angiogenic factor herein is an antibody that binds to Vascular Endothelial Growth Factor (VEGF). In an alternate embodiment, the IgG is administered with a therapeutic agent that induces or enhances adaptive immune response, for example an antibody that targets CTLA-4. In an alternate embodiment, the IgG is administered with a tyrosine kinase inhibitor. By "tyrosine kinase inhibitor" as used herein is meant a molecule that inhibits to some extent tyrosine kinase activity of a tyrosine kinase. In an alternate embodiment, the IgG variants are administered with a cytokine.

Pharmaceutical compositions are contemplated wherein an IgG variant and one or more therapeutically active agents are formulated. Formulations of the IgG variants are prepared for storage by mixing the IgG having the desired degree of purity with optional pharmaceutically acceptable carriers, excipients or stabilizers (Remington's Pharmaceutical Sciences 16th edition, Osol, A. Ed., 1980, entirely incorporated by reference), in the form of lyophilized formulations or aqueous solutions. The formulations to be used for in vivo administration are preferably sterile. This is readily accomplished by filtration through sterile filtration membranes or other methods. The IgG variants and other therapeutically active agents disclosed herein may also be formulated as immunoliposomes, and/or entrapped in microcapsules.

The concentration of the therapeutically active IgG variant in the formulation may vary from about 0.1 to 100% by weight. In a preferred embodiment, the concentration of the IgG is in the range of 0.003 to 1.0 molar. In order to treat a patient, a therapeutically effective dose of the IgG variant may be administered. By "therapeutically effective dose" herein is meant a dose that produces the effects for which it is administered. The exact dose will depend on the purpose of the treatment, and will be ascertainable by one skilled in the art using known techniques. Dosages may range from 0.01 to 100 mg/kg of body weight or greater, for example 0.01, 0.1, 1.0, 10, or 50 mg/kg of body weight, with 1 to 10 mg/kg being preferred. As is known in the art, adjustments for protein degradation, systemic versus localized delivery, and rate of new protease synthesis, as well as the age, body weight, general health, sex, diet, time of administration, drug interaction and the severity of the condition may be necessary, and will be ascertainable with routine experimentation by those skilled in the art.

Administration of the pharmaceutical composition comprising an IgG variant, preferably in the form of a sterile aqueous solution, may be done in a variety of ways, including, but not limited to, orally, subcutaneously, intravenously, parenterally, intranasally, intraotically, intraocularly, rectally, vaginally, transdermally, topically (e.g., gels, salves, lotions, creams, etc.), intraperitoneally, intramuscularly, intrapulmonary (e.g., AERx® inhalable technology commercially available from Aradigm, or Inhance® pulmonary delivery system commercially available from Nektar Therapeutics, etc. Therapeutic described herein may be administered with other therapeutics concomitantly, i.e., the therapeutics described herein may be co-administered with other therapies or therapeutics, including for example, small molecules, other biologicals, radiation therapy, surgery, etc.

EXAMPLES

Examples are provided below to illustrate the present invention. These examples are not meant to constrain the present invention to any particular application or theory of operation. For all positions discussed in the present invention, numbering is according to the EU index as in Kabat (Kabat et al., 1991, *Sequences of Proteins of Immunological Interest*, 5th Ed., United States Public Health Service, National Institutes of Health, Bethesda, entirely incorporated by reference). Those skilled in the art of antibodies will appreciate that this convention consists of nonsequential numbering in specific regions of an immunoglobulin sequence, enabling a normalized reference to conserved positions in immunoglobulin families. Accordingly, the positions of any given immunoglobulin as defined by the EU index will not necessarily correspond to its sequential sequence.

Example 1

DNA Construction, Expression, and Purification of Fc Variants

Figure 11:
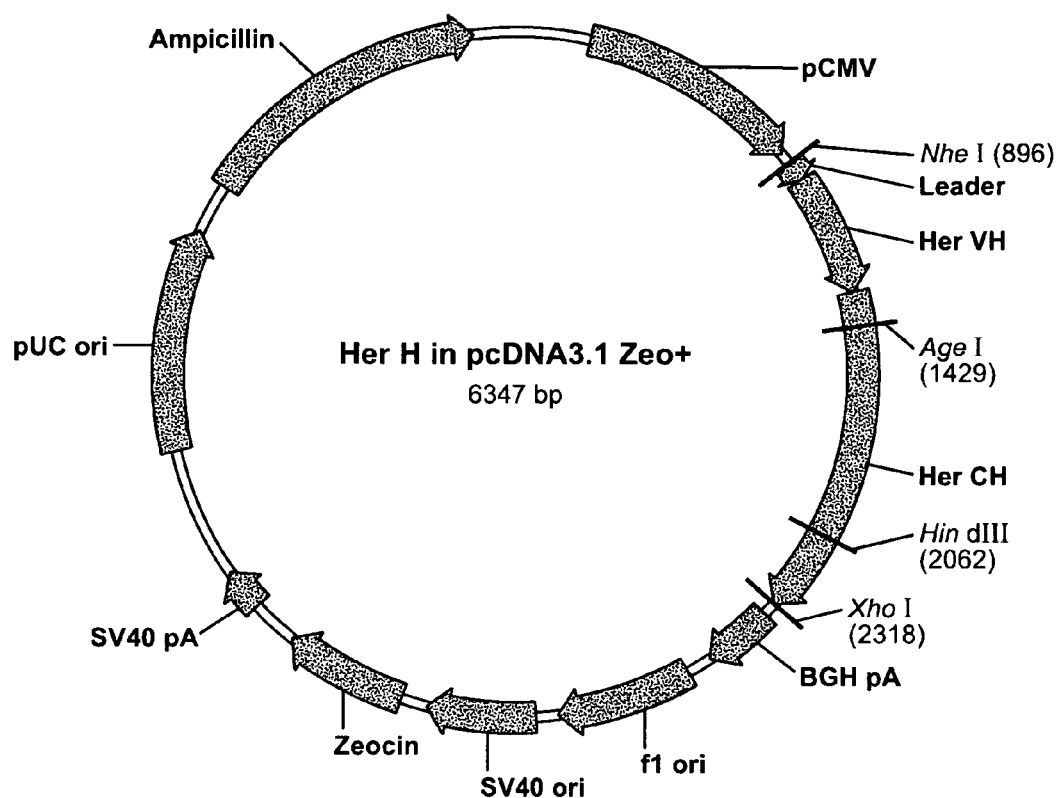
FIG. 11. Diagram of the vector pcDNA3.1 Zeo+, which may be used in the construct of Fc variants.

Fc variants were constructed using the human IgG1 Fc domain and the variable domain of trastuzumab (Herceptin®), Genentech). The Fc polypeptides were part of Alemtuzumab, Trastuzumab or AC10. Alemtuzumab (Campath®, a registered trademark of Millenium) is a humanized monoclonal antibody currently approved for treatment of B-cell chronic lymphocytic leukemia (Hale et al., 1990, *Tissue Antigens* 35:118-127, entirely incorporated by reference). Trastuzumab (Herceptin®), a registered trademark of Genentech) is an anti-HER2/neu antibody for treatment of metastatic breast cancer. AC10 is a anti-CD30 monoclonal antibody. The Herceptin variable region was assembled using recursive PCR. This variable region was then cloned with human IgG1 into the pcDNA3.1/Zeo(+) vector (Invitrogen), shown in FIG. 11. Plasmids were propagated in One Shot TOP10 *E. coli* cells (Invitrogen) and purified using the Hi-Speed Plasmid Maxi Kit (Qiagen). Plasmids were sequenced to verify the presence of the cloned inserts.

Site-directed mutagenesis was done using the Quikchange™ method (Stratagene). Plasmids containing the desired substitutions, insertions, and deletions were propagated in One Shot TOP10 *E. coli* cells (Invitrogen) and purified using the Hi-Speed Plasmid Maxi Kit (Qiagen). DNA was sequenced to confirm the fidelity of the sequences.

Plasmids containing heavy chain gene (VH-Cγ1-Cγ2-Cγ3) (wild-type or variants) were co-transfected with plasmid containing light chain gene (VL-Cκ) into 293T cells. Media were harvested 5 days after transfection, and antibodies were purified from the supernatant using protein A affinity chromatography (Pierce). Antibody concentrations were determined by bicinchoninic acid (BCA) assay (Pierce).

Example 2

Binding Affinity Measurements

Binding of Fc polypeptides to Fc ligands was assayed with surface plasmon resonance measurements. Surface plasmon resonance (SPR) measurements were performed using a BIAcore 3000 instrument (BIAcore AB). Wild-type or variant antibody was captured using immobilized protein L (Pierce Biotechnology, Rockford, Ill.), and binding to receptor analyte was measured. Protein L was covalently coupled to a CM5 sensor chip at a concentration of 1 uM in 10 mM sodium acetate, pH 4.5 on a CM5 sensor chip using N-hydroxysuccinimide/N-ethyl-N'-(−3-dimethylamino-propyl) carbodiimide (NHS/EDC) at a flow rate of 5 ul/min. Flow cell 1 of every sensor chip was mocked with NHS/EDC as a negative control of binding. Running buffer was 0.01 M HEPES pH 7.4, 0.15 M NaCl, 3 mM EDTA, 0.005% v/v Surfactant P20 (HBS-EP, Biacore, Uppsala, Sweden), and chip regeneration buffer was 10 mM glycine-HCl pH 1.5. 125 nM Wild-type or variant trastuzumab antibody was bound to the protein L CM5 chip in HBS-EP at 1 ul/min for 5 minutes. FcRn-His-GST analyte, a FcRn fused to a His-tag and glutathione S transferase, in serial dilutions between 1 and 250 nM, were injected for 20 minutes association, 10 minutes dissociation, in HBS-EP at 10 ul/min. Response, measured in resonance units (RU), was acquired at 1200 seconds after receptor injection, reflecting near steady state binding. A cycle with antibody and buffer only provided baseline response. RU versus 1/log concentration plots were generated and fit to a sigmoidal dose response using nonlinear regression with GraphPad Prism.

Binding of Fc polypeptides to Fc ligands was also done with AlphaScreen™ (Amplified Luminescent Proximity Homogeneous Assay). AlphaScreen™ is a bead-based non-radioactive luminescent proximity assay. Laser excitation of a donor bead excites oxygen, which if sufficiently close to the acceptor bead will generate a cascade of chemiluminescent events, ultimately leading to fluorescence emission at 520-620 nm. The principal advantage of the AlphaScreen™ is its sensitivity. Because one donor bead emits up to 60,000 excited oxygen molecules per second, signal amplification is extremely high, allowing detection down to attomolar ($10^{-18}$) levels. Wild-type antibody was biotinylated by standard methods for attachment to streptavidin donor beads, and tagged Fc ligand, for example FcRn, was bound to glutathione chelate acceptor beads. The AlphaScreen™ was applied as a direct binding assay in which the Fc/Fc ligand interactions bring together the donor and acceptor beads. Addtionally, the AlphaScreen™ was applied as a competition assay for screening designed Fc polypeptides. In the absence of competing Fc polypeptides, wild-type antibody and FcRn interact and produce a signal at 520-620 nm. Untagged Fc domains compete with wild-type Fc/FcRn interaction, reducing fluorescence quantitatively to enable determination of relative binding affinities.

Example 3

FcRn-Binding Properties of Fc Variants

Binding affinity of IgG1 Fc to FcRn was measured with variant antibodies using AlphaScreen™. The Fc polypeptides were part of Alemtuzumab or Trastuzumab. Alemtuzumab (Campath®, Ilex) is a humanized monoclonal antibody currently approved for treatment of B-cell chronic lymphocytic leukemia (Hale et al., 1990, *Tissue Antigens* 35:118-127, entirely incorporated by reference). Trastuzumab (Herceptin®, Genentech) is an anti-HER2/neu antibody for treatment of metastatic breast cancer.

Figure 12A:
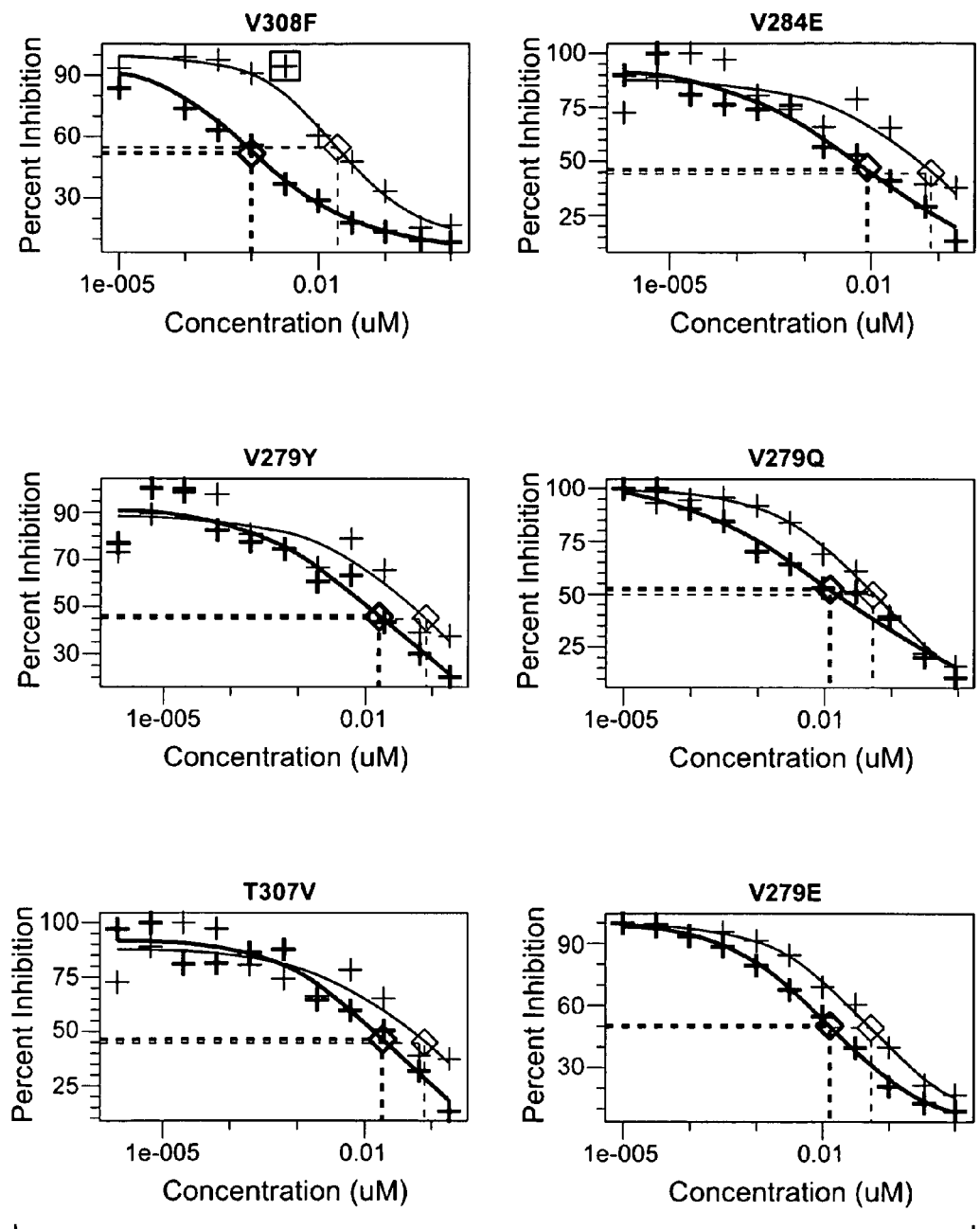
FIG. 12. Competition FcRn binding data of wild-type Fc and Fc variants of the present invention. In each panel, the Fc variants of the present invention are shown as the left (red or dark grey) curve and the wild-type trastuzumab is shown as the right (blue or light grey) curve.
Figure 12B:
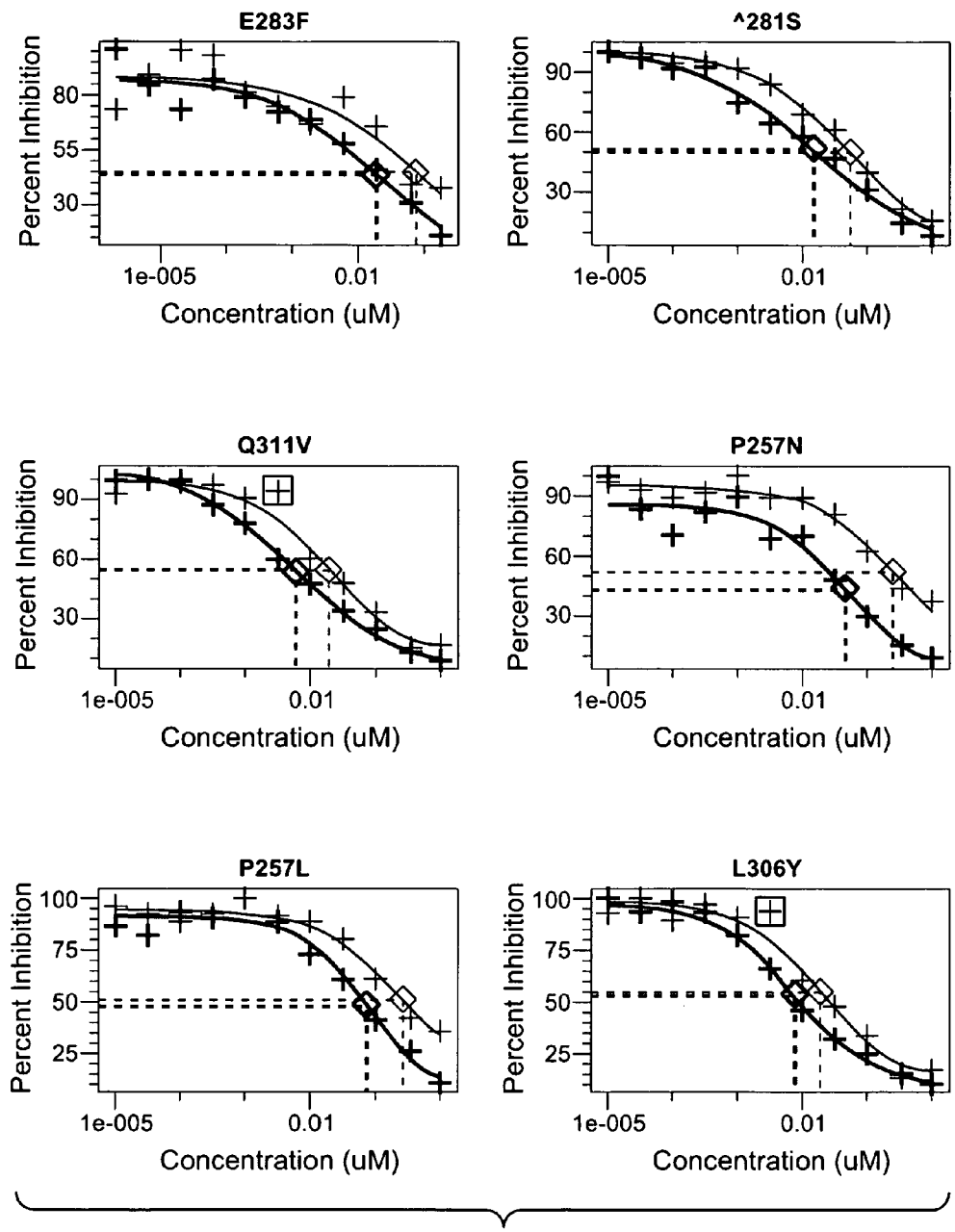

Competitive AlphaScreen™ data were collected to measure the relative binding of the Fc variants compared to the wild-type antibody at pH6.0. Examples of the AlphaScreen™ signal as a function of competitor antibody are shown in FIG. 12. The 12 variant curves shown, those of P257L, P257N, V279E, V279Q, V279Y, ^281S, E283F, V284E, L306Y, T307V, V308F, and Q311V, demonstrate increased affinity as each variant curve is shifted to the left of the wild-type curve in their box. Competition AlphaScreen™ data for Fc variants of the present invention are summarized in FIGS. 13 and 14. The relative FcRn binding of the variant compared to wild type are listed. Values greater than one demonstrate improved binding of the Fc variant to FcRn compared to the wild type. For example, the variant E283L and V284E have 9.5-fold and 26-fold stronger binding than the wild type, respectively.

Figure 15:
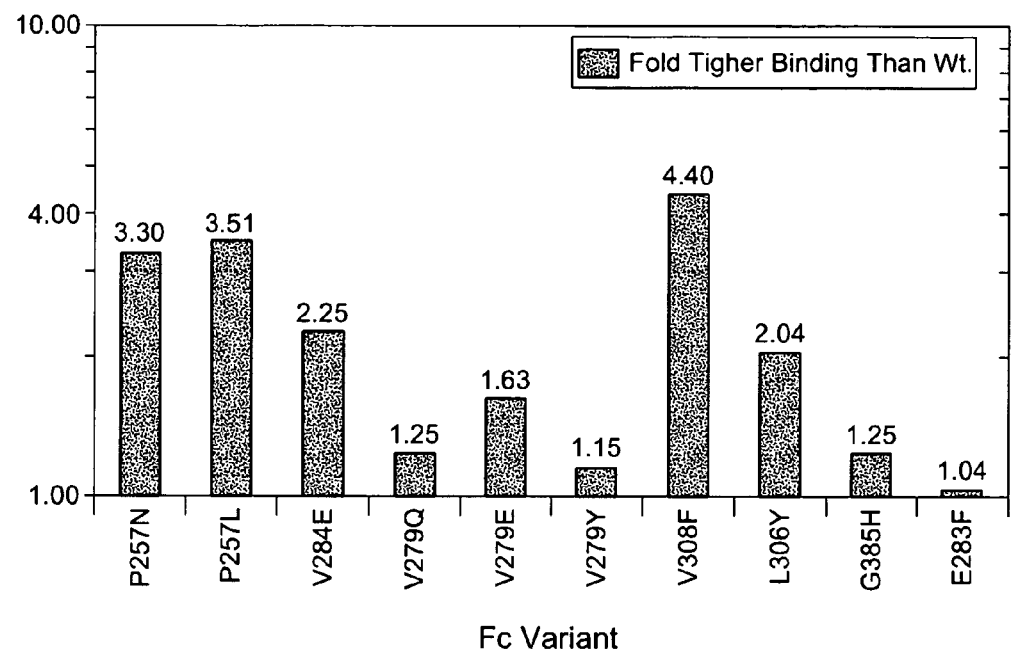
FIG. 15. Summary of surface plasmon resonance experiments of Fc variants with improved binding to FcRn. The bar graph shows the fold-increase in FcRn binding affinity of each variant relative to wild-type Fc domain.
Figures 1, 16A:
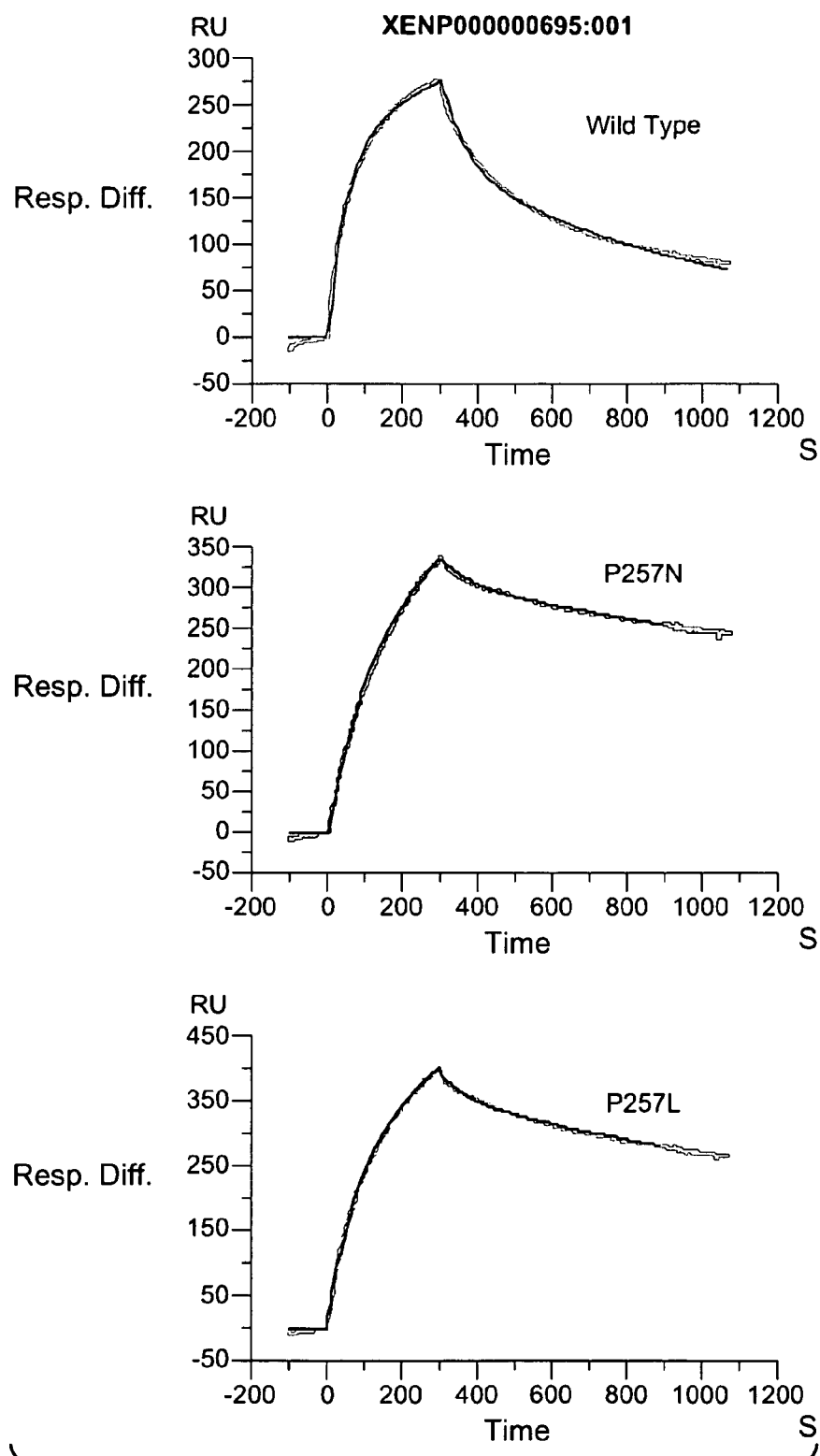
Figures 2, 16A:
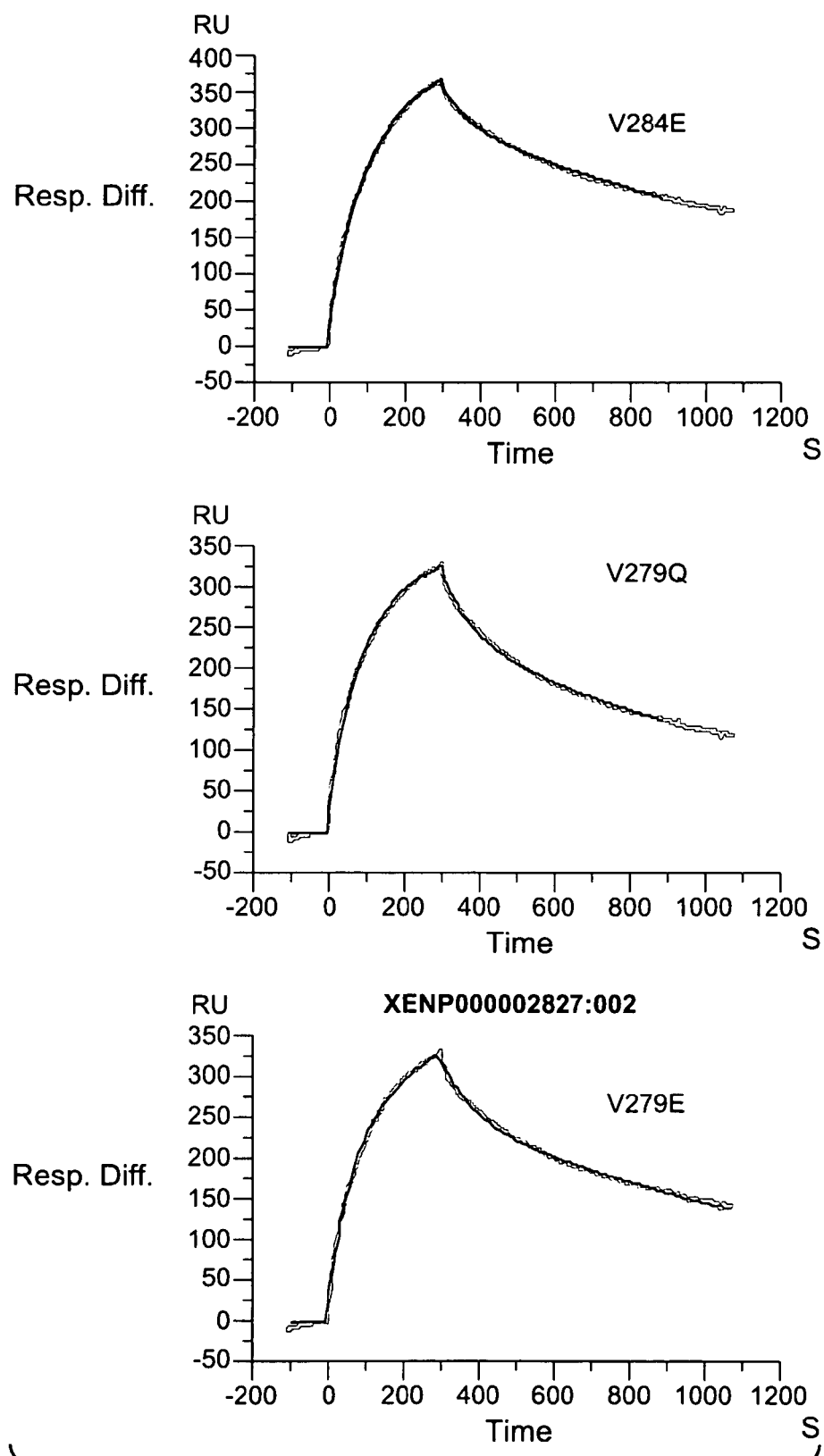
FIG. 2. Human IgG sequences used in the present invention with the EU numbering as in Kabat et al.
Figures 1, 16B:
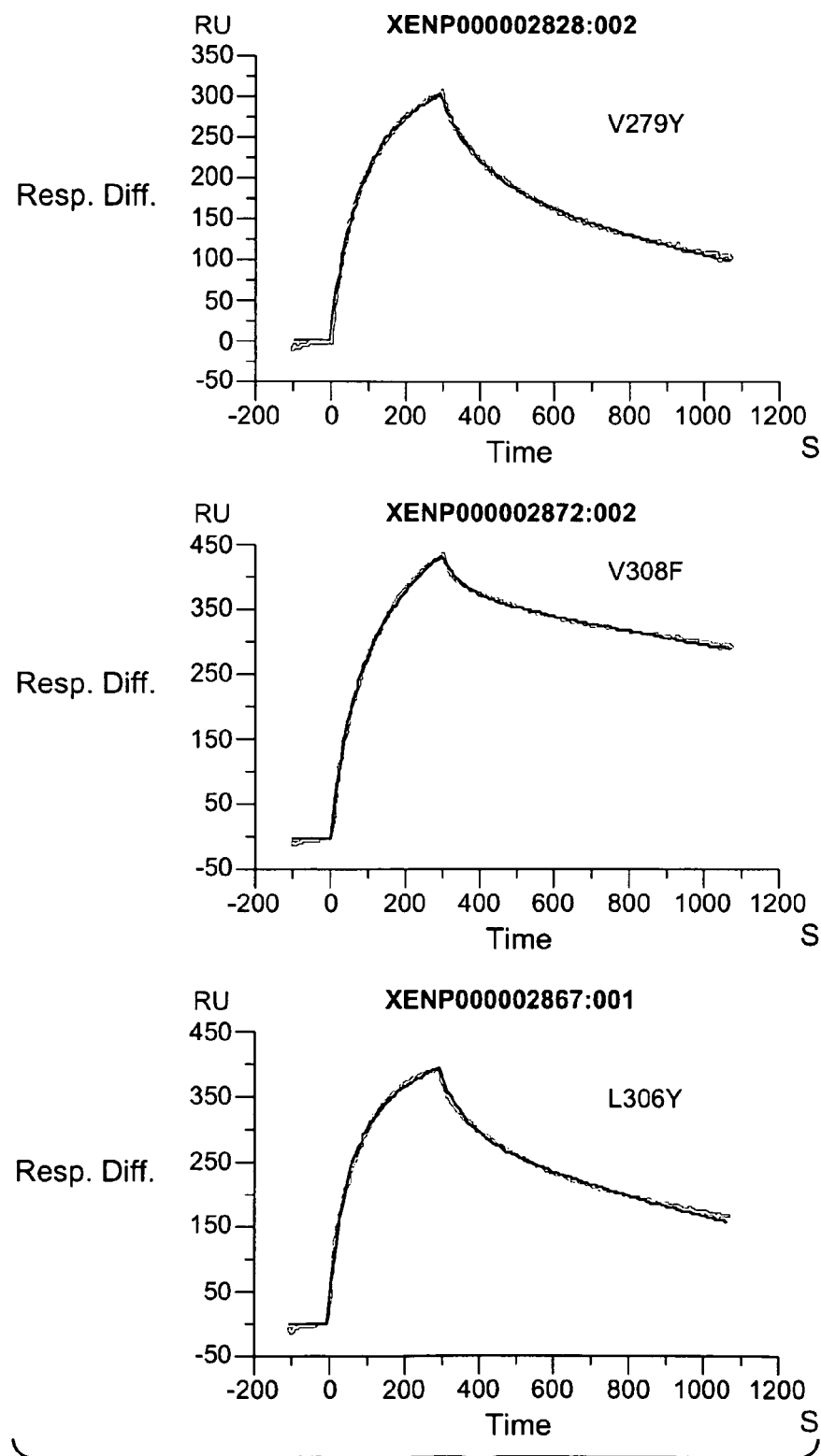
Figures 2, 16B:
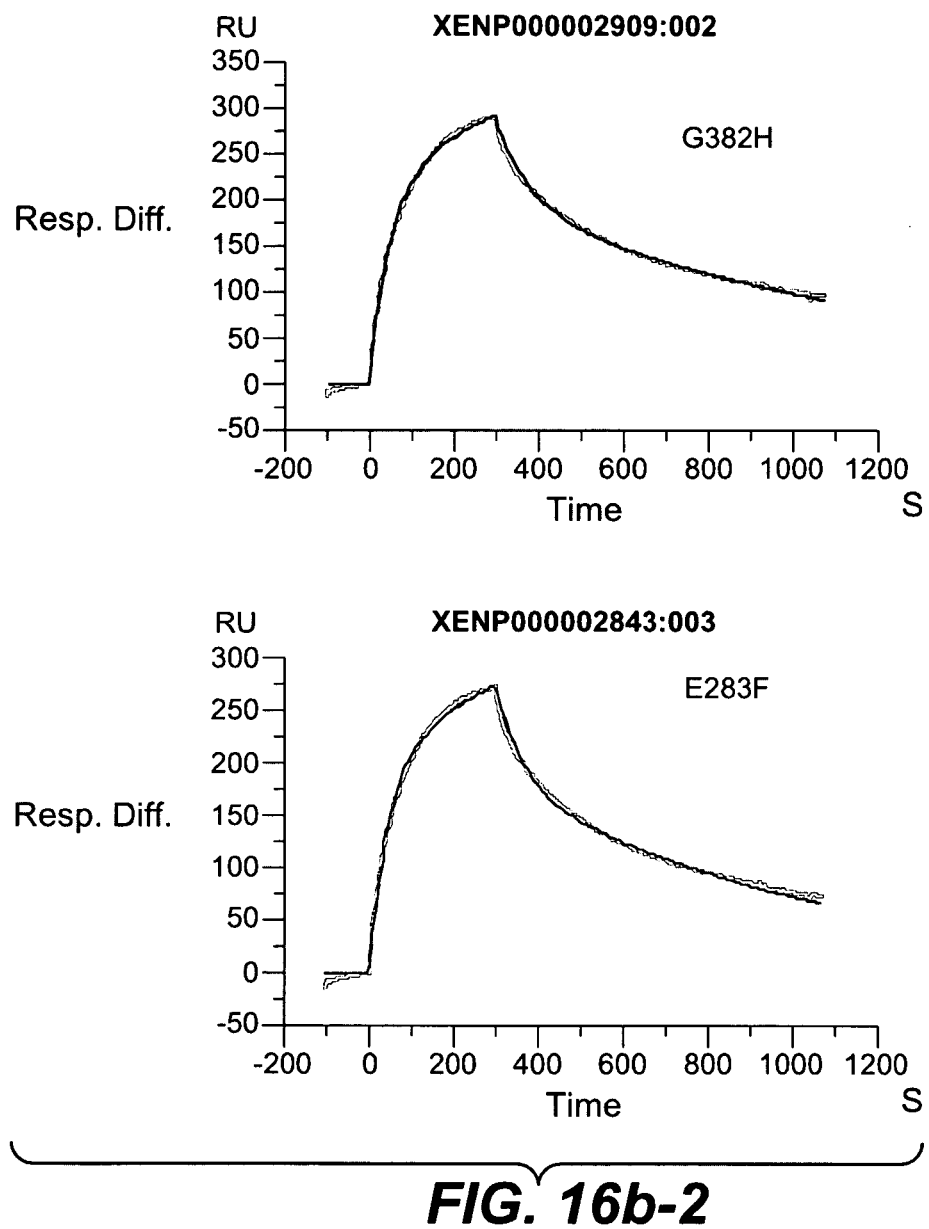

Surface plasmon resonance measurements of many variants also show increased binding to FcRn as shown in FIGS. 15 and 16.

At position 257, all variants that remove the imino acid, proline, and substitute an amino acid without the backbone N to side chain covalent bond, allow the backbone more flexibility which allows more freedom for the Fc domain to better bind FcRn. In particular, variants at position 257 to L and N have strong FcRn binding at pH 6, demonstrating that the four atom side chain and gamma branching pattern of the side chain helps the Fc domain make productive, ie strong, FcRn interactions. Position 308 interacts with position 257. Both of these positions in turn interact with H310, which is directly involved in the Fc/FcRn interactions (Table 2, Burmeister et al (1994) Nature 372:379-383, entirely incorporated by reference). The Fc variants V308F and V08Y have a 2.9-fold and 4.3-fold increase in FcRn affinity over wild type (FIG. 13). Positions 279 and 385 interact with FcRn as variants V279E, V279Q and V279Y and G385H and G385N all have stronger FcRn interactions. These variants all are to amino acids that are capable of hydrogen bonding.

The Fc variant N434Y has particularly strong binding to FcRn at pH 6.0 as shown in FIG. 13. The single variant N434Y has 16-fold increased binding. Combinations of this variant with other modifications led to even stronger binding. For example, P257L/N434Y, A281S/N434Y, and V308F/N434Y show 830-fold, 180-fold, and 350-fold increases in FcRn binding.

Example 4

Variants Incorporating Insertions and Deletions

Insertions and deletions that alter the strength of Fc/FcRn interactions were constructed and their binding properties to various Fc ligands were measured. An Fc variant with an inserted Ser residue between residues 281 and 282, using the EU numbering of Kabat et al, was designed to increase the FcRn binding properties of the Fc domain. This variant is referred to as ^281S with "^" meaning an insertion following the position given. The inserted sequence, which may be more than one residue, is given following the position number. This Fc variant was constructed in the kappa, IgG1 anitbody trastuzumab (Herceptin®, Genetech) using methods disclosed herein. An insertion at the site between residues 281 and 282 shifts the Fc loop residues C-terminal of residue 281 toward the C-terminus of the loop and alters the side chain positioning. Fc variants comprising substitutions at positions 282, 283, and 284 suggested that the C-terminal shift of this loop was beneficial (See FIG. 14). Another variant, a deletion of N286, sometimes referred to as N286#, was also constructed to shift the position of this FcRn-binding loop. Both of these variants show an increased binding affinity for FcRn at pH 6.0.

Figure 17A:
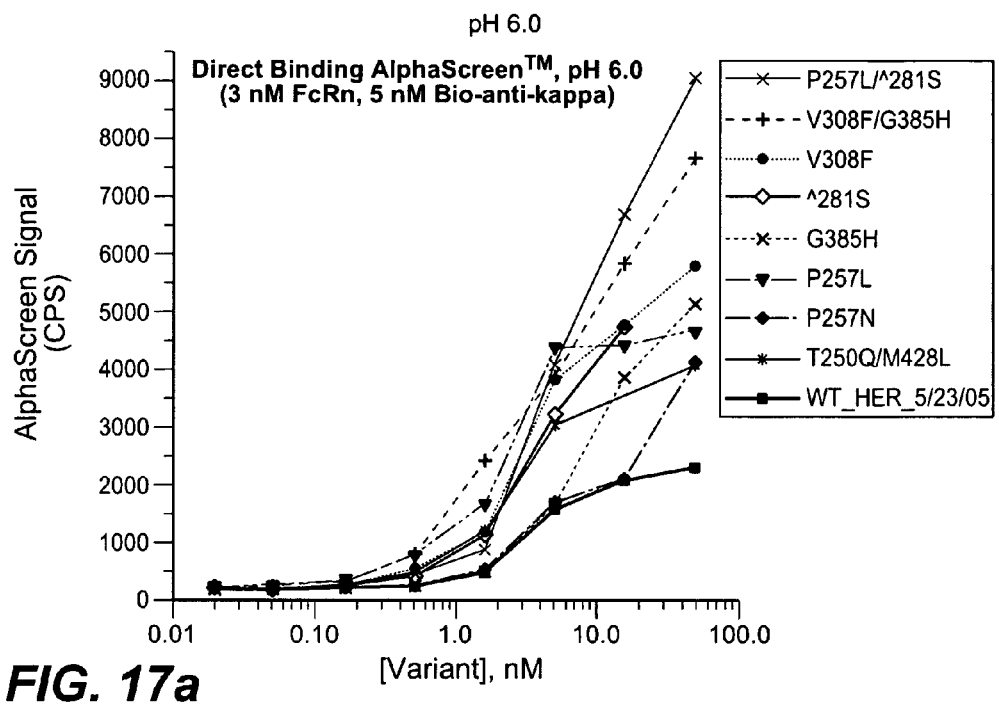
FIG. 17. Binding assays of Fc variants of the present invention to FcRn. Shown are direct binding assays measured by AlphaScreen™ at pH 6.0 (a and b) and pH 7.0 (c).
Figure 17B:
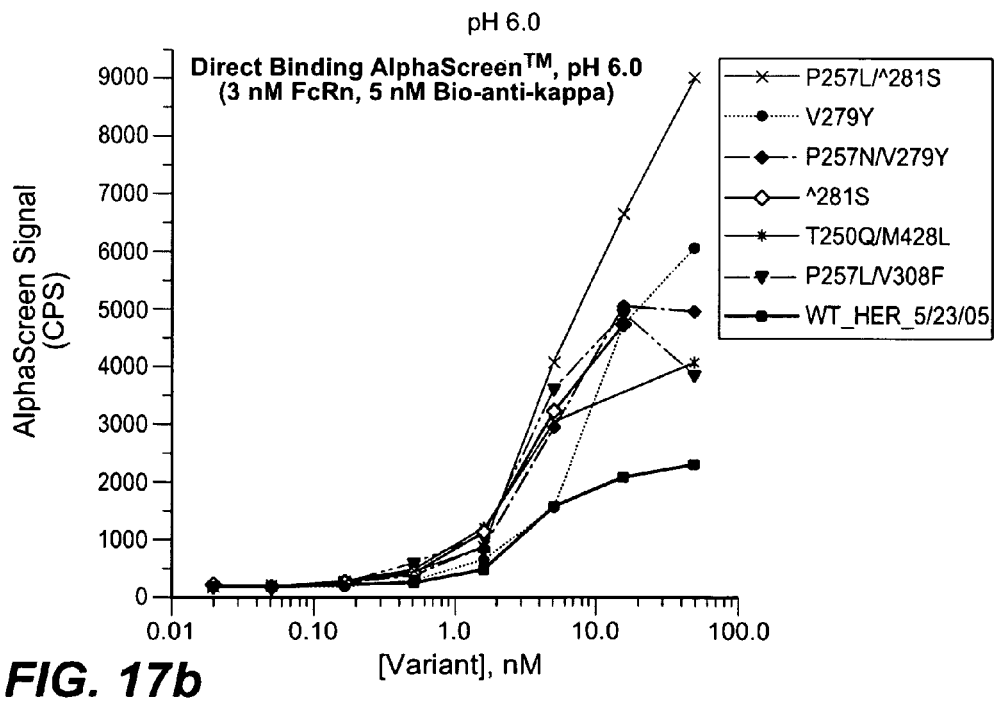
Figure 17C:
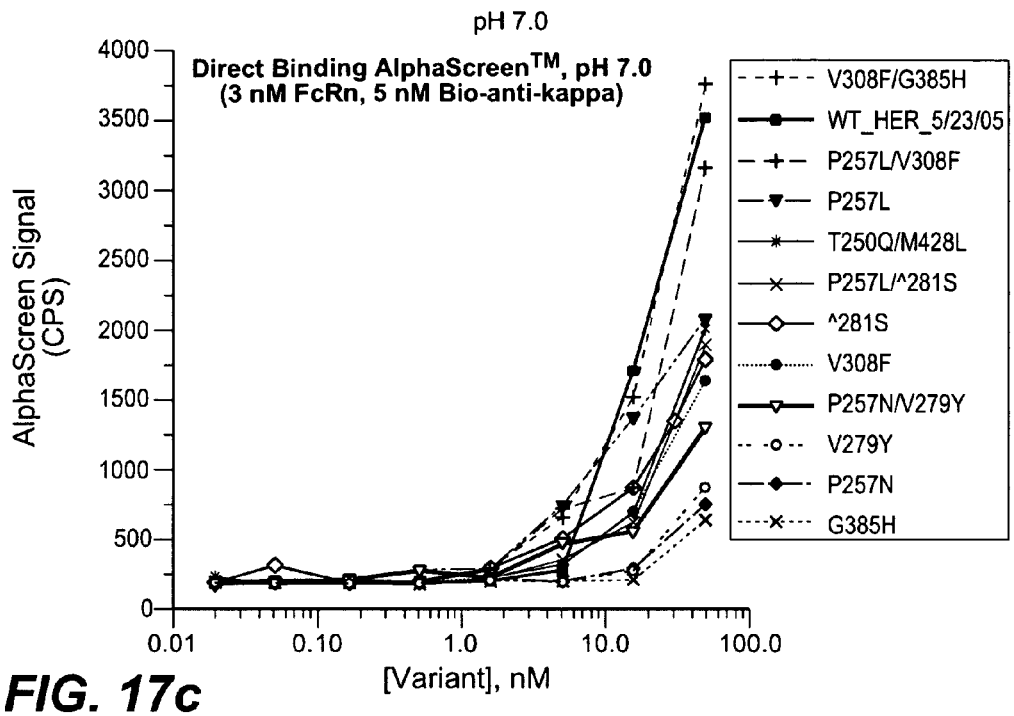

The AlphaScreen™ data shows the binding of the ^281S variant and other variants to FcRn. This AlphaScreen™ data was collected as a direct binding assay. Higher levels of chemiluminescent signals demonstrate stronger binding. As the concentrations of the variants are raised in the assay, stronger signals are created. These data at pH 6.0, in FIGS. 17a and 17b, demonstrate the increased affinity of ^281S, P257L, P257L/^281S (a combination substitution/insertion variant) and other variants over the wild-type Fc. Also shown is a double substitution, T250Q/M428L, shown previously to have an increased serum half in monkeys (Hinton et al., 2004, J. Biol. Chem. 279(8): 6213-6216, entirely incorporated by reference). The insertion, ^281S, alone increases the Fc/FcRn binding. Additionally, ^281S further increases the binding of P257L when the two modifications are combined in the variant P257L/^281S as shown in the ~40 nM data points. The data in FIG. 17c demonstrate that these variants do not show increased FcRn binding at pH 7.0. The reduced affinity at pH 7.0 is desired for increased half-life in vivo, because it allows the release of Fc polypeptides from FcRn into the extracellular space, an important step in Fc recycling.

Figure 18:
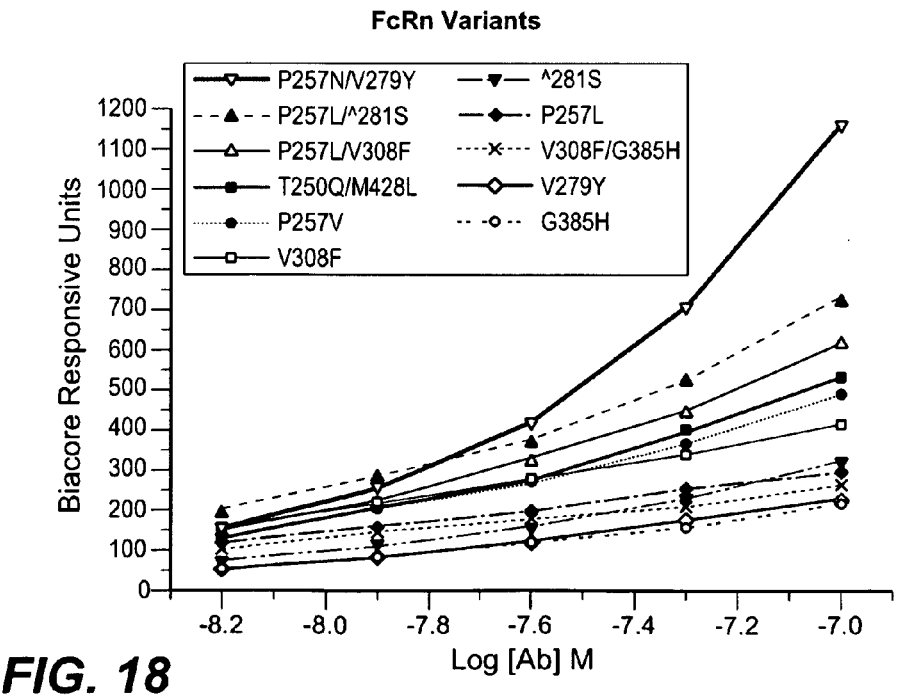
FIG. 18. Binding assays of Fc variants of the present invention to FcRn. Shown are the surface plasmon resonance units created upon binding of the variant Fc to surface-bound FcRn.

Surface plasmon resonance experiments also demonstrate the improved binding of ^281S to FcRn. FIG. 18 shows the response units created as various Fc variant binding to FcRn on the chip surface. After allowing the variant to fully bind to the chip, the response units are recorded and shown on the ordinate. The insertion, ^281S shows binding properties comparable to other variants shown herein to have increased affinity for FcRn over the wild type (See FIGS. 13, 14 and 15, for examples).

The deletion variant comprising a deletion of N286, N286#, also shows increased affinity for FcRn over wild type. This variant has a 2.0-fold increase in FcRn affinity as shown in FIG. 13. The data therein are also AlphaScreen™ data collected as a competition experiment at pH 6.0. The variants are used to inhibit the binding of wild-type Fc, linked to the donor bead, with FcRn, linked to the acceptor beads. Two-fold less free N286# was needed than free wild-type Fc to inhibit the binding of the donor/acceptor beads through the Fc/FcRn complex. This demonstrates the 2-fold tighter binding of N286# over the wild type.

Other Fc variants comprising insertions or deletions have decreased affinity for FcRn. The insertion variant, A254N has greatly decreased FcRn binding as would be expected from the nature and positioning of the variant. This variant places the insertion, an Asn, in the middle of an FcRn binding loop. This insertion has only 1.1% of the binding of the binding affinity of the wild type (FIG. 13).

Whereas particular embodiments of the invention have been described above for purposes of illustration, it will be appreciated by those skilled in the art that numerous variations of the details may be made without departing from the invention as described in the appended claims. All references cited herein are incorporated in their entirety.

We claim:

1. A polypeptide comprising a variant Fc region as compared to a parent Fc polypeptide, said variant Fc region comprising an amino acid substitution at position 308, wherein said amino acid substitution is selected from the group consisting of a phenylalanine, a cysteine, a tyrosine and a tryptophan, wherein said polypeptide has increased in vivo half-life as compared to a polypeptide comprising said parent Fc polypeptide, wherein said polypeptide is selected from the group consisting of an antibody and an immunoadhesin and wherein numbering is according to the EU Index in Kabat et al.

2. A polypeptide according to claim 1 which is an antibody.

3. An antibody according to claim 2 wherein said antibody is selected from the group consisting of a chimeric antibody, a humanized antibody, or a human antibody.

4. An antibody according to claim 2 wherein said antibody has specificity for an antigen selected from the group consisting of vascular endothelial growth factor (VEGF), tumor necrosis factor-α (TNF-α), CD25, nerve growth factor (NGF), IgE and epidermal growth factor receptor (EGFR).

5. A composition comprising the polypeptide of claim 1 and a carrier.

\* \* \* \* \*